United States Patent [19]

Osbourne et al.

[11] Patent Number: 5,872,215
[45] Date of Patent: Feb. 16, 1999

[54] SPECIFIC BINDING MEMBERS, MATERIALS AND METHODS

[75] Inventors: Jane Katharine Osbourne, Cambridge; Deborah Julie Allen, London; John Gerald McCafferty, Babraham, all of United Kingdom

[73] Assignees: Medical Research Council, London; Cambridge Antibody Technology Ltd., Cambridgeshire, both of England

[21] Appl. No.: 652,816

[22] Filed: May 23, 1996

Related U.S. Application Data

[63] Continuation-in-part of Ser. No. 244,597, filed as PCT/GB92/02240 Dec. 2, 1992..

[30] Foreign Application Priority Data

| Dec. 2, 1991 | [GB] | United Kingdom | 9125582 |
| Dec. 4, 1991 | [GB] | United Kingdom | 9125579 |
| Mar. 24, 1992 | [GB] | United Kingdom | 9206318 |
| Sep. 23, 1992 | [GB] | United Kingdom | 9206372 |
| Dec. 7, 1995 | [GB] | United Kingdom | 9525004 |
| May 23, 1996 | [GB] | United Kingdom | 9610824 |

[51] Int. Cl.$^6$ ............ C12P 21/08; C07K 16/32; G01N 33/574
[52] U.S. Cl. ............ 530/387.3; 530/387.5; 530/387.7; 530/388.15; 530/388.85; 530/389.7; 530/391.3; 435/7.23
[58] Field of Search ............ 530/387.3, 387.5, 530/387.7, 388.15, 388.85, 389.7, 391.3; 435/7.23

[56] References Cited

FOREIGN PATENT DOCUMENTS

| WO 88/06630 | 9/1988 | WIPO . |
| WO 90/14424 | 11/1990 | WIPO . |
| WO 90/14430 | 11/1990 | WIPO . |

(List continued on next page.)

FOREIGN PATENT DOCUMENTS

| WO 90/14443 | 11/1990 | WIPO . |
| WO 91/01990 | 2/1991 | WIPO . |
| WO 92/01047 | 1/1992 | WIPO . |
| WO 92/20791 | 11/1992 | WIPO . |
| WO 93/11236 | 6/1993 | WIPO . |
| WO 95/06067 | 3/1995 | WIPO . |
| WO 95/15341 | 6/1995 | WIPO . |

OTHER PUBLICATIONS

Bouanani, M. et al., "Autoimmunity to Human Thyroglobulin," *Arthritis and Rheumatism*, 34(12):1585–1593 (Dec., 1991).

James, K. and Bell, G.T., "Human monoclonal antibody production: Current status and future prospects," *Journal of Immunological Methods*, 100:5–40 (1987).

Kim, J.G. and Abeyounis, C.J., "Isolation and Characterization of Rat Carcinoembryonic Antigen," *Int. Arch. Allergy Appl. Immunol.*, 92:43–49 (1990).

Kim, J.G. and Abeyounis, C.J., "Monoclonal Rat Antibodies to Rat Carcinoembryonic Antigen," *Immunological Investigations*, 17(1):41–48 (1988).

Portolano, S. et al., "A Human Fab Fragment Specific for Thyroid Peroxidase Generated by Cloning Thyroid Lymphocyte–Derived Immunoglobulin Genes in a Bacteriophage Lambda Library," *Biochemical and Biophysical Research Communications*, 179(1):372–377 (Aug. 30, 1991).

Huse et al., "Generation of a Large Combinatorial Library of the Immunoglobulin Repertoire in Phage Lambda," *Science*, 246:1275–1281 (Dec. 8, 1989).

Kang et al., "Linkage of Recombination and Replication Functions by Assembling Cominatorial Antibody Fab Libraries Along Phage Surfaces," *Proc. Nat'l Acad. Sci., USA*, 88:4363–4366 (May, 1991).

Marks et al., "By–Passing Immunization: Building High Affinity Human Antibodies by Chain Shuffling," *Bio/Technology*, 10:779–783 (Jul., 1992).

Winter and Milstein, "Man–made Antibodies," *Nature*, 349:293–299 (Jan. 24, 1991).

Epstein et al., "Production of Carcinoembryonic Antigen From a Human Colon Adenocarcinoma Cell Line II. Use of Monoclonal Antibodies to Carcinoembryonic Antigen For Antigen Purification and Characterization," *Developments in Biological Standardization*, 66:429–437 (1987).

Griffiths et al., "Human anti–self antibodies with high specificity from phage display libraries," *The EMBO J.*, 12(2):725–734 (1993).

Griffiths et al., "Isolation and high affinity human antibodies directly from large synthetic repertoires," *The EMBO J.*, 13:3245–3260 (1994).

Hu et al., "Minibody: A Novel Engineered Anti–Carcinoembryonic Antigen Antibody Fragment (Single–Chain Fv–$H_H$3) Which Exhibits Rapid, High–Level Targeting of Xenografts," *Cancer Research*, 56(13):3055–3061 (Jul. 1, 1996).

Nap et al., "Specificity and Affinity of Monoclonal Antibodies against Carcinoembryonic Antigen," *Cancer Research*, 52:2329–2339 (Apr. 15, 1992).

(List continued on next page.)

*Primary Examiner*—David Saunders
*Assistant Examiner*—F. Pierre VanderVegt
*Attorney, Agent, or Firm*—Marshall, O'Toole, Gerstein, Murray & Borun

[57] ABSTRACT

Specific binding members for human carcinoembryonic antigen (CEA) comprise a human antibody antigen binding domain. The specific binding members may have a dissociation constant less than $1.0 \times 10^{-8}$M and may be substantially non-crossreactive with human liver and/or other normal tissues. They may be specific for the A3-B3 extracellular domain of CEA. They may be specific for a carbohydrate epitope of CEA. They may be produced by recombinant expression from encoding nucleic acid and modified and manipulated in various manners in accordance with known techniques. CEA is a tumour antigen and the specific binding members have proven ability to bind and target CEA both in vitro and in vivo.

32 Claims, 44 Drawing Sheets

OTHER PUBLICATIONS

Oikawa et al., "The Carcinoembryonic Antigen (CEA) Contains Multiple Immunoglobulin–Like Domains," *Biochemical and Biophysical Research Communication*, 144(2):534–542 (Apr. 29, 1987).

Osbourn et al., "Generation of a panel of related human scFv antibodies with high affinities for human CEA," *Immunotechnology (Amsterdam)* 2(3):181–196 (1996).

Wellerson et al., "Enhanced Binding Activity Observed Between Anti–Carcinoembryonic Monoclonal Antibodies," *Hybridoma*, 5(3):199–213 (1986).

CDR1

| | | | |
|---|---|---|---|
| CEA1 | QVQLQQSGPGLVKPSETLSLTCTVSGDSIS | SYYWS | WIRQPPGKGLEWIG (CONT.) |
| CEA2 | QVQLVQSGGGLVQPGGSLRLSCAASGFSVS | SNYMS | WVRQSPGKGLEYVS (CONT.) |
| CEA3 | EVHLVESGRALVQPGGSLRLSCAASGFTFS | SYAMS | WVRQAPGKGLEWVS (CONT.) |
| CEA4 | QVQLQQSGPGRVKPSETLSLTCTVSGYSVS | VSYYW | GWIRQSPGTGLEWI (CONT.) |
| CEA5 | EVQLVESGGGVVRPGGSLRLSCAASGFTFD | DYGMS | WVRQAPGKGLEWVS (CONT.) |
| CEA6 | QVQLVQSGAEVKKPGSSVKVSCKASGGTFS | NSPIN | WLRQAPGQGLEWMG (CONT.) |
| CEA7 | QVTLQQSGAEVKKPGPSVKVSCKASGYTFT | AYGFN | WVRQAPGQGLEWMW (CONT.) |

CDR2

| | | |
|---|---|---|
| CEA1 | YIHYSGSTNSNPSLKS | RVTISGDTSKKRFSLKLSSVTAADTAVYYCAA (CONT.) |
| CEA2 | AISSNGGSTYYADSVKG | RFTISRDNSKNTLYLQMSSSPRAEDTAVYYCAR (CONT.) |
| CEA3 | AISGSGGSTYYADSVKG | RFTISRDNSKNTLYLQMNSLRAEDTAVYYCAR (CONT.) |
| CEA4 | GSISHSGSTYYNPSLKS | RVTISGDASKNQFFLRLTSVTAADTAVYYCAR (CONT.) |
| CEA5 | GINWNGGSTGYADSVKG | RFTISRDNAKNSLYLQMNSLRAEDTAVYYCAR (CONT.) |
| CEA6 | SIIPSFGTANYAQKFQG | RLTITADESTSTAYMELSSSLRSEDTAVYYCAG (CONT.) |
| CEA7 | ISAYSGNTKYAQKFQG | RVTMTDTSTSTAYMELRSLRSEDTAVYYCAG (CONT.) |

| | CDR3 | | |
|---|---|---|---|
| CEA1 | SGAYDNYGIDV | WGKGTLVTVSS | (SEQ ID NO: 10) |
| CEA2 | FINPYGMDV | WGQGTLVTVSS | (SEQ ID NO: 11) |
| CEA3 | ALVRGVIKD | WGQGTLVTVSS | (SEQ ID NO: 12) |
| CEA4 | SEPTANFDS | WGRGTLVTVSS | (SEQ ID NO: 13) |
| CEA5 | RRYALDY | WGQGTLVTVSR | (SEQ ID NO: 14) |
| CEA6 | RSHNYELYYYYMDV | WGQGTMVTVSS | (SEQ ID NO: 1) |
| CEA7 | RRGGFRFRPMDV | WGQGTMVTVSS | (SEQ ID NO: 19) |

FIG. 1(A) (B)

| | | | | | | |
|---|---|---|---|---|---|---|
| CEA1 | CAGGTACAGC | TGCAGCAGTC | AGGCCCAGGA | CTGGTGAAGC | CTTCGGAGAC | (CONT.) |
| CEA2 | CAGGTTCAGC | TGGTGCAGTC | TGGGGAGGC | TTGGTCCAGC | CTGGGGGGTC | (CONT.) |
| CEA3 | GAGGTACACC | TGGTGGAGTC | TGGGAGAGCC | TTGGTACAGC | CTGGGGGGTC | (CONT.) |
| CEA4 | CAGGTACAGC | TGCAGCAGTC | AGGCCCAGGA | CGGGTGAAGC | CTTCGGAGAC | (CONT.) |
| CEA5 | GAGGTGCAGC | TGGTGGAGTC | TGGGGAGGT | GTGGTACGGC | CTGGGGGGTC | (CONT.) |
| CEA6 | CAGGTTCAGC | TGGTTCAGTC | TGGGGCTGAG | GTGAAGAAGC | CTGGGTCCTC | (CONT.) |
| CEA7 | CAGGTTACCC | TGCAGCAGTC | TGGGGCTGAG | GTGAAGAAGC | CTGGGCCCTC | (CONT.) |
| | | | | | | |
| CEA1 | CCTGTCCCTC | ACCTGCACTG | TCTCTGGTGA | CTCCATCAGT | AG | (SEQ ID NO: 20) |
| CEA2 | CCTGAGACTC | TCCTGTGCAG | CCTCTGGATT | CAGGCGTCAGT | AG | (SEQ ID NO: 21) |
| CEA3 | CCTGAGACTC | TCCTGTGCAG | CCTCTGGATT | CACCTTTAGC | AG | (SEQ ID NO: 22) |
| CEA4 | GCTGTCCCTC | ACCTGCACTG | TCTCTGGTTA | CTCCGTCAGT | GT | (SEQ ID NO: 23) |
| CEA5 | CCTGAGGCTC | TCCTGTGCAG | CCTCTGGATT | CACCTTTGAT | GA | (SEQ ID NO: 24) |
| CEA6 | GGTGAAGGTC | TCCTGCAAGG | CTTCTGGAGG | CACCTTCAGC | AA | (SEQ ID NO: 25) |
| CEA7 | GGTGAAGGTC | TCCTGCAAGG | CTTCTGGATA | TACCTTCACC | GC | (SEQ ID NO: 26) |

FIG. 1(A)(c)

| | | | | | |
|---|---|---|---|---|---|
| CEA1 | TTACTACTGG | AGCTGGATCC | GGCAACCCCC | AGGGAAGGGA | CTGGAGTGGA (CONT.) |
| CEA2 | CAATTACATG | AGCTGGGTCC | GCCAGTCTCC | AGGGAAGGGA | CTGGAATATG (CONT.) |
| CEA3 | CTATGCCATG | AGCTGGGTCC | GCCAGGCTCC | AGGGAAGGGG | CTGGAGTGGG (CONT.) |
| CEA4 | GAGTTACTAC | TGGGGCTGGA | TCCGGCAGTC | CCCAGGGACG | GGGCTGGAGT (CONT.) |
| CEA5 | TTATGGCATG | AGCTGGGTCC | GCCAAGCTCC | AGGGAAGGGG | CTGGAGTGGG (CONT.) |
| CEA6 | CTCTCCTATC | AACTGGGCTGC | GACAGGCCCC | CGGACAAGGG | CTTGAGTGGA (CONT.) |
| CEA7 | CTATGGTTTC | AACTGGGTGC | GACAGGCCCC | CGGACAAGGG | CTTGAGTGGA (CONT.) |
| | | | | | |
| CEA1 | TTGGGTATAT | CCATTACAGT | GGGAG | (SEQ ID NO: 20) | |
| CEA2 | TTTCAGCTAT | TAGTAGTAAT | GGGGG | (SEQ ID NO: 21) | |
| CEA3 | TCTCAGCTAT | TAGTGGTAGT | GGTGG | (SEQ ID NO: 22) | |
| CEA4 | GGATTGGGAG | TATCTCTCAT | AGTGG | (SEQ ID NO: 23) | |
| CEA5 | TCTCTGGTAT | TAATTGGAAT | GGTGG | (SEQ ID NO: 24) | |
| CEA6 | TGGGAAGTAT | CATCCCTTCC | TTTGG | (SEQ ID NO: 25) | |
| CEA7 | TGTGGATCAG | CGCTTACAGT | GGTAA | (SEQ ID NO: 26) | |

FIG. 1(A) (D)

| | | | | | |
|---|---|---|---|---|---|
| CEA1 | CACCAACTCC | AACCCCTCCC | TCAAGAGTCG | AGTCACCATA | TCAGGAGACA (CONT.) |
| CEA2 | TAGCACATAC | TACGCAGACT | CCGTGAAGGG | CAGATTCACC | ATCTCCAGAG (CONT.) |
| CEA3 | TAGCACATAC | TACGCAGACT | CCGTGAAGGG | CCGGTTCACC | ATCTCCAGAG (CONT.) |
| CEA4 | GAGCACCTAC | TACAACCCGT | CCCTCAAGAG | TCGAGTCACC | ATATCAGGAG (CONT.) |
| CEA5 | TAGCACAGGT | TATGCAGACT | CTGTGAAGGG | CCGATTCACC | ATCTCCAGAG (CONT.) |
| CEA6 | TACAGCAAAC | TACGCTCAGA | AGTTCCAGGG | CAGACTCACG | ATTACCGCGG (CONT.) |
| CEA7 | CACAAAGTAC | GCTCAGAAGT | TCCAGGGCAG | AGTCACGATG | ACCACAGACA (CONT.) |

| | | | | |
|---|---|---|---|---|
| CEA1 | CGTCCAAGAA | GCGGTTCTCC | CTGAA | (SEQ ID NO: 20) |
| CEA2 | ACAATTCCAA | GAACACGCTG | TATCT | (SEQ ID NO: 21) |
| CEA3 | ACAATTCCAA | GAACACGCTG | TATCT | (SEQ ID NO: 22) |
| CEA4 | ACGCATCCAA | GAACCAGTTT | TTCCT | (SEQ ID NO: 23) |
| CEA5 | ACAACGCCAA | GAACTCCCTG | TATCT | (SEQ ID NO: 24) |
| CEA6 | ACGAATCCAC | GAGCACAGCC | TACAT | (SEQ ID NO: 25) |
| CEA7 | CATCCACGAG | CACAGCCTAC | ATGGA | (SEQ ID NO: 26) |

FIG. 1(A) (E)

| | | | | | | |
|---|---|---|---|---|---|---|
| CEA1 | GCTGAGCTCT | GTGACCGCCG | CGGACACGGC | CGTGTATTAC | TGTGCGGCGT | (CONT.) |
| CEA2 | TCAAATGAGC | AGTCCGAGAG | CTGAGGACAC | GGCTGTGTAT | TACTGTGCGA | (CONT.) |
| CEA3 | GCAAATGAAC | AGCCTGAGAG | CCGAGGACAC | GGCTGTGTAT | TACTGTGCGA | (CONT.) |
| CEA4 | GAGGCTGACT | TCTGTGACCG | CCGCGGACAC | GGCCGTTTAT | TACTGTGCGA | (CONT.) |
| CEA5 | TCAAATGAAC | AGTCTGAGAG | CCGAGGACAC | AGCCGTGTAT | TACTGTGCGA | (CONT.) |
| CEA6 | GGAGCTGAGC | AGCCTGAGAT | CTGAGGACAC | GGCCGTGTAT | TACTGTGCAA | (CONT.) |
| CEA7 | GCTGAGGAGC | CTGAGATCTG | AGGACACGGC | CGTGTATTAC | TGTGCGGGAC | (CONT.) |

| | | | | | |
|---|---|---|---|---|---|
| CEA1 | CGGGTGCCTA | CGATAATTAC | GGTATAGACG | TCTGGGGCAA | AG (SEQ ID NO: 20) |
| CEA2 | GATTTATAAA | TCCCTACGGT | ATGGACGTCT | GGGGCCAGGG | CA (SEQ ID NO: 21) |
| CEA3 | GAGCTTTGGT | TCGGGGAGTT | ATAAAGGACT | GGGGCCAGGG | AA (SEQ ID NO: 22) |
| CEA4 | GATCTGAGCC | TACCGCCAAC | TTTGATTCTT | GGGGCAGGGG | CA (SEQ ID NO: 23) |
| CEA5 | GAAGGCGGTA | TGCGTTGGAT | TATTGGGGCC | AAGGTACCCT | GG (SEQ ID NO: 24) |
| CEA6 | GACGGAGCCA | CAACTACGAA | CTCTACTACT | ACTACATGGA | CG (SEQ ID NO: 25) |
| CEA7 | GGAGAGGCGG | CTTCCGATTC | CGACCGATGG | ACGTCTGGGG | CC (SEQ ID NO: 26) |

FIG. 1(A) (F)

| | | |
|---|---|---|
| CEA1 | GCACCCTGGTCACCGTCTCGAGT | (SEQ ID NO: 20) |
| CEA2 | CCCTGGTCACCGTCTCCTCA | (SEQ ID NO: 21) |
| CEA3 | CCCTGGTCACCGTCTCCTCA | (SEQ ID NO: 22) |
| CEA4 | CCCTGGTCACCGTCTCGAGT | (SEQ ID NO: 23) |
| CEA5 | TCACCGTGTCGAGA | (SEQ ID NO: 24) |
| CEA6 | TCTGGGGCCAGGGGACAATGGTCACCGTCTCGAGT | (SEQ ID NO: 25) |
| CEA7 | AGGGGACAATGGTCACCGTCTCGAGC | (SEQ ID NO: 26) |

FIG. 1(A)(G)

```
                                                CDR1
CEA1  QSVLTQPPSVSAPPGQKVTISC  SGSTPNIGNNYVS  WYQQHPGKAPKLMIY  (CONT.)
CEA2  ......................  .............  ...............  (CONT.)
CEA3  ......................  .............  ...............  (CONT.)

CEA4  SSELTQDPAVSVPLGQTVRITC  QGDSLRSYYAS    WYQQKPGQPPVLVIY  (CONT.)
CEA5  ......................  ...........    ...............  (CONT.)

CEA6  DIQMTQSPSSLSASIGDRVTITC RASEGIYHWLA    WYQQKPGKAPKLLIY  (CONT.)
CEA7  ...................... ...........    ...............  (CONT.)
```

FIG. 1(B)

| FIG. 1(B)(A)–1(B)(G) |
|---|

|      | CDR2     |                              | CDR3        |         |
|------|----------|------------------------------|-------------|---------|
| CEA1 | DVSKRPS  | GVPDRFSGSKSGNSASLDISGLQSEDEADYYC | AAWDDSLSEFL | (CONT.) |
| CEA2 | ........ | ................................ | ........... | (CONT.) |
| CEA3 | ........ | ................................ | ........... | (CONT.) |
| CEA4 | GKNNRPS  | GIPDRFSGSSSGNTASLTITGAQAEDEADYYC | NSRDSSGNHVV | (CONT.) |
| CEA5 | ........ | ................................ | ........... | (CONT.) |
| CEA6 | KASSLAS  | GAPSRFSGSGSGTDFTLTISSLQPDDFATYYC | QQYSNYPLT   | (CONT.) |
| CEA7 | ........ | ................................ | ........... | (CONT.) |

FIG. 1(B) (B)

CEA1 FGTGTKLEIKR (SEQ ID No. 15)
CEA2 ........... (SEQ ID No. 15)
CEA3 ........... (SEQ ID No. 15)

CEA4 FGGGTKLEIKR (SEQ ID No. 16)
CEA5 ........... (SEQ ID No. 16)

CEA6 FGGGTKLEIKR (SEQ ID No. 2)
CEA7 ........... (SEQ ID No. 2)

FIG. 1(B) (C)

```
CEA1  CAGTCTGTGT TGACGCAGCC GCCCTCAGTG TCTGCGCCCC CAGGACAGAA    (CONT.)
CEA2  .......... .......... .......... .......... ..........    (CONT.)
CEA3  .......... .......... .......... .......... ..........    (CONT.)

CEA4  TCGTCTGAGC TGACTCAGGA CCCTGCTGTG TCTGTGCCCT TGGGACAGAC    (CONT.)
CEA5  .......... .......... .......... .......... ..........    (CONT.)

CEA6  GACATCCAGA TGACCCAGTC TCCTTCCACT CTGTCTGCAT CTATTGGAGA    (CONT.)
CEA7  .......... .......... .......... .......... ..........    (CONT.)

CEA1  GGTCACCATT TCCTGCTCTG GAAGCACC  (SEQ ID No. 27)
CEA2  .......... .......... ........
CEA3  .......... .......... ........

CEA4  AGTCAGGATC ACATGCCAAG GAGACAGC  (SEQ ID No. 28)
CEA5  .......... .......... ........

CEA6  CAGAGTCACC ATCACCTGCC GGGCCAGT  (SEQ ID No. 29)
CEA7  .......... .......... ........
```

FIG. 1(B) (D)

```
CEA1  CCCAACATTG GGAATAATTA TGTCTCCTGG TACCAACAGC ACCCAGGCAA  (CONT.)
CEA2  .......... .......... .......... .......... ..........  (CONT.)
CEA3  .......... .......... .......... .......... ..........  (CONT.)

CEA4  CTCAGAAGCT ATTATGCAAG CTGGTACCAG CAGAAGCCAG GACAGCCCCC  (CONT.)
CEA5  .......... .......... .......... .......... ..........  (CONT.)

CEA6  GAGGGTATTT ATCACTGGTT GGCCTGGTAT CAGCAGAAGC CAGGGAAAGC  (CONT.)
CEA7  .......... .......... .......... .......... ..........  (CONT.)

CEA1  AGCCCCCAAA CTCATGATTT ATGATGTCAG TAAGCGGCC (SEQ ID No. 27)
CEA2  .......... .......... .......... .........
CEA3  .......... .......... .......... .........

CEA4  TGTACTTGTC ATCTATGGTA AAAACAACCG GCCCTCAGG (SEQ ID No. 28)
CEA5  .......... .......... .......... .........

CEA6  CCCTAAACTC CTGATCTATA AGGCCTCTAG TTTAGCCAG (SEQ ID No. 29)
CEA7  .......... .......... .......... .........
```

FIG. 1(B) (E)

```
CEA1   CTCAGGGGTC  CCTGACCGAT  TCTCTGGCTC  CAAGTCTGGC  AACTCAGCCT   (CONT.)
CEA2   ..........  ..........  ..........  ..........  ..........   (CONT.)
CEA3   ..........  ..........  ..........  ..........  ..........   (CONT.)
CEA4   GATCCCAGAC  CGATTCTCTG  GCTCCAGCTC  AGGAAACACA  GCTTCCTTGA   (CONT.)
CEA5   ..........  ..........  ..........  ..........  ..........   (CONT.)
CEA6   TGGGGCCCCA  TCAAGGTTCA  GCGGCAGTGG  ATCTGGGACA  GATTTCACTC   (CONT.)
CEA7   ..........  ..........  ..........  ..........  ..........   (CONT.)

CEA1   CCCTGGACAT  CAGTGGGCTC  CAGTCTGA  (SEQ ID No. 27)
CEA2   ..........  ..........  ........
CEA3   ..........  ..........  ........
CEA4   CCATCACTGG  GGCTCAGGCG  GAAGATGA  (SEQ ID No. 28)
CEA5   ..........  ..........  ........
CEA6   TCACCATCAG  CAGCCTGCAG  CCTGATGA  (SEQ ID No. 29)
CEA7   ..........  ..........  ........
```

FIG. 1(B) (F)

```
CEA1  GGATGAGGCT GATTATTACT GTGCAGCATG GGATGACAGC CTGAGTGAAT  (CONT.)
CEA2  .......... .......... .......... .......... ..........  (CONT.)
CEA3  .......... .......... .......... .......... ..........  (CONT.)

CEA4  GGCTGACTAT TACTGTAACT CCCGGGACAG CAGTGGTAAC CATGTGGTAT  (CONT.)
CEA5  .......... .......... .......... .......... ..........  (CONT.)

CEA6  TTTTGCAACT TATTACTGCC AACAATATAG TAATTATCCG CTCACTTTCG  (CONT.)
CEA7  .......... .......... .......... .......... ..........  (CONT.)

CEA1  TTCTCTTCGG AACTGGGACC AAGCTGGAGA TCAAACGT (SEQ ID No. 27)
CEA2  .......... .......... .......... ........
CEA3  .......... .......... .......... ........

CEA4  TCGGCGGAGG GACCAAGCTG GAGATCAAAC GT       (SEQ ID No. 28)
CEA5  .......... .......... .......... ..

CEA6  GCGGAGGGAC CAAGCTGGAG ATCAAACGT           (SEQ ID No. 29)
CEA7  .......... .......... .........
```

FIG. 1(B)(G)

|               |                                      | CDR1  |         |
|---------------|--------------------------------------|-------|---------|
| (SEQ ID NO:1) CEA6    | QVQLVQSGAEVKKPGSSVKVSCKASGGTFS | NSPIN | (CONT.) |
| (SEQ ID NO:6) T06D10  | .............................. | ..... | (CONT.) |
| (SEQ ID NO:7) HBA11   | .............................. | ..... | (CONT.) |
| (SEQ ID NO:8) HBB11   | .............................. | ..... | (CONT.) |
| (SEQ ID NO:9) HBB6    | .............................. | ..... | (CONT.) |

|               |                    | CDR2              |         |
|---------------|--------------------|-------------------|---------|
| (SEQ ID NO:1) CEA6    | WLRQAPGQGLEWMG | SIIPSFGTANYAQKFQG | (CONT.) |
| (SEQ ID NO:6) T06D10  | .............. | ................. | (CONT.) |
| (SEQ ID NO:7) HBA11   | .............. | ................. | (CONT.) |
| (SEQ ID NO:8) HBB11   | .............. | ................. | (CONT.) |
| (SEQ ID NO:9) HBB6    | .............. | ................. | (CONT.) |

|               |                                     |         |
|---------------|-------------------------------------|---------|
| (SEQ ID NO:1) CEA6    | RLTITADESTSTAYMELSSLRSEDTAVYYCAG | (CONT.) |
| (SEQ ID NO:6) T06D10  | ................................ | (CONT.) |
| (SEQ ID NO:7) HBA11   | ................................ | (CONT.) |
| (SEQ ID NO:8) HBB11   | .........................R...... | (CONT.) |
| (SEQ ID NO:9) HBB6    | ................................ | (CONT.) |

|  | CDR3 |
| --- | --- |
|  | RSHNYELYYYYMDV WGQGTMVTVSS |
| (SEQ ID NO:1) CEA6 | .............. ........... |
| (SEQ ID NO:6) T06D10 | C............. ........... |
| (SEQ ID NO:7) HBA11 | ANSCNRS....... R.......... |
| (SEQ ID NO:8) HBB11 | HN............ ........... |
| (SEQ ID NO:9) HBB6 | ...T.......... ........... |

```
              CDR1
        DIQMTQSPSTLSASIGDRVTITC RASEGIYHWLA WYQQKPGKAPKLLIY    (CONT.)
CEA6'
LOB1C   ......................  ..........  ...............  (CONT.)
LOE17   ......................  ..........  ...............  (CONT.)
LOSC2   ......................  ..........  ...............  (CONT.)

CDR2                                        CDR3
        KASSLASGAP  SRFSGSGSGTDFTLTISSLQPDDFATYYC  QQYSNYPLT  (CONT.)
CEA6'
LOB1C   ..........  ............................  ..SYST...  (CONT.)
LOE17   ..........  ............................  ..YDNG...  (CONT.)
LOSC2   ..........  ............................  ..SYST...  (CONT.)

CEA6'   FGGGTKLEIKR  (SEQ ID No. 53)
LOB1C   ...........  (SEQ ID No. 17)
LOE17   ...........  (SEQ ID No. 18)
LOSC2   ...........  (SEQ ID No. 17)
```

FIG. 4

|  | DIQMTQSPSTLSASIGDRVTITC | CDR1<br>RASEGIYHWLA | WYQQKPGKAPKLLIY |  |
|---|---|---|---|---|
| CEA6' | | | | (CONT.) |
| T06D4 | ..V................... | ...Q..SS... | ......R...V... | (CONT.) |
| T06D8 | ..V................... | ...Q..SS... | ......R...V... | (CONT.) |
| T06D12 | ..V................... | ...Q..SS... | ............. | (CONT.) |

|  | CDR2<br>KASSLASGAP | SRFSGSGSGTDFTLTISSLQPDDFATYYC | CDR3<br>QQYSNYPLT |  |
|---|---|---|---|---|
| CEA6' | | | | (CONT.) |
| T06D4 | ..T.EV.V. | ...............E............ | ..SYST.W. | (CONT.) |
| T06D8 | ..T.E..V. | ...............E............ | ..SYST.W. | (CONT.) |
| T06D12 | ..........  | ............................ | ......... | (CONT.) |

|  | FGGGTKLEIKR |  |
|---|---|---|
| CEA6' | ........... | (SEQ ID NO: 53) |
| T06D4 | ..Q........ | (SEQ ID NO: 3) |
| T06D8 | ..Q........ | (SEQ ID NO: 4) |
| T06D12 | ........... | (SEQ ID NO: 8) |

Fig.5.
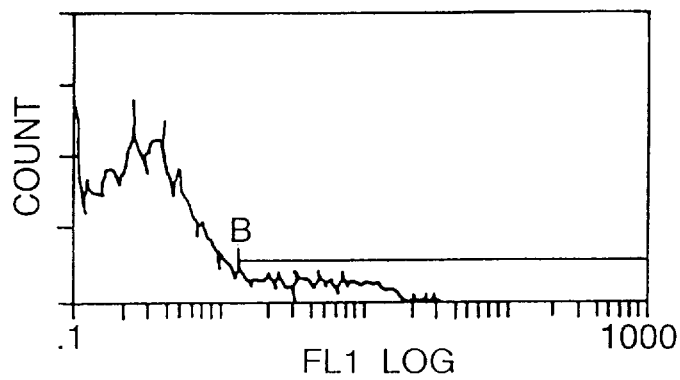
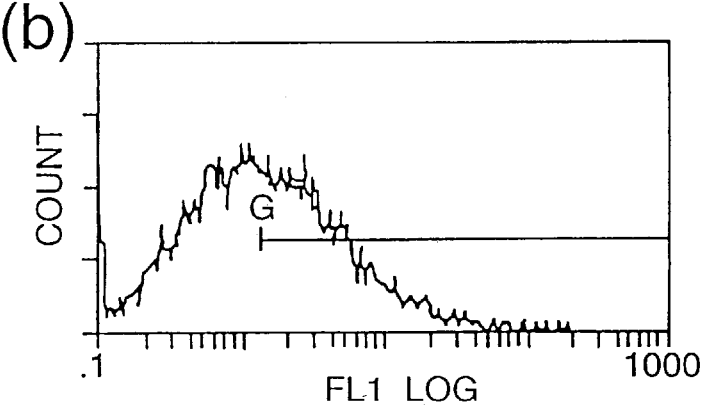
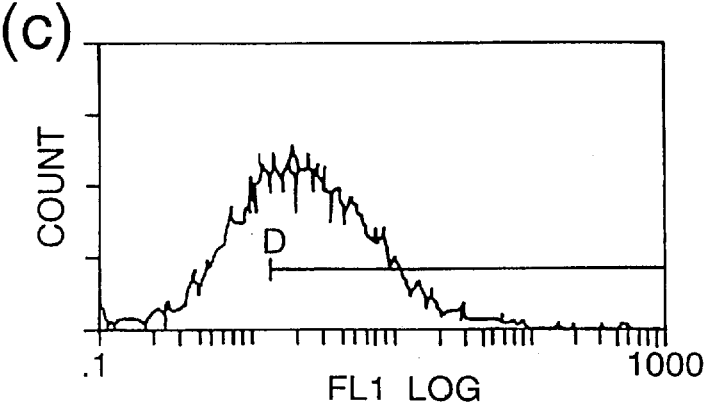

Fig.5 (Cont).
(d)
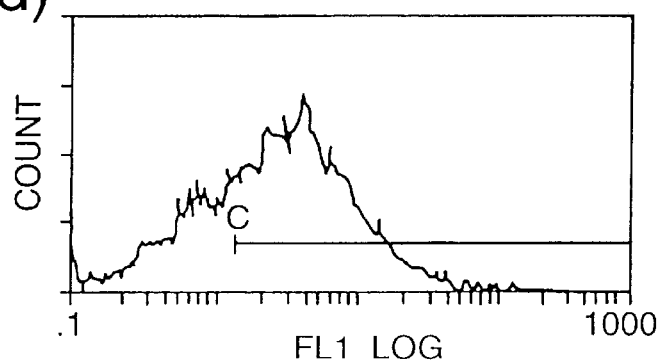
(e)
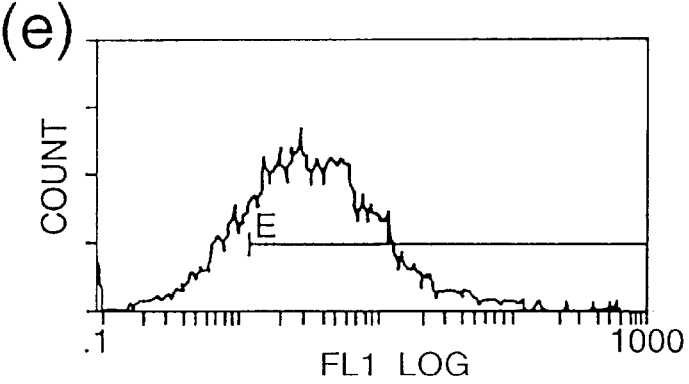
(f)
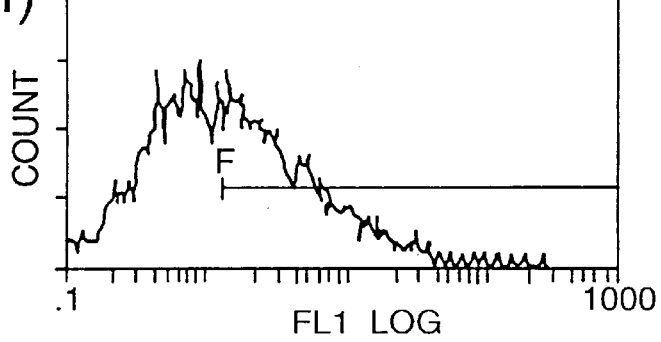
(g)
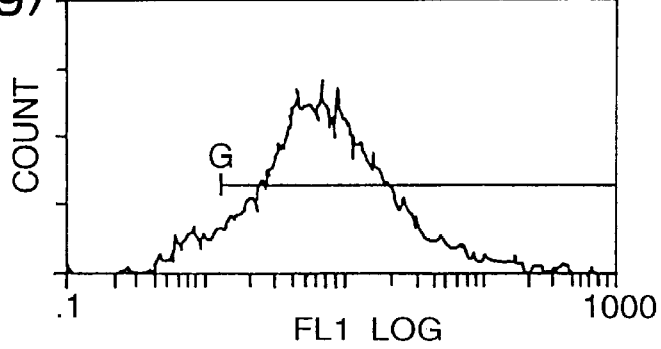

Fig. 7.
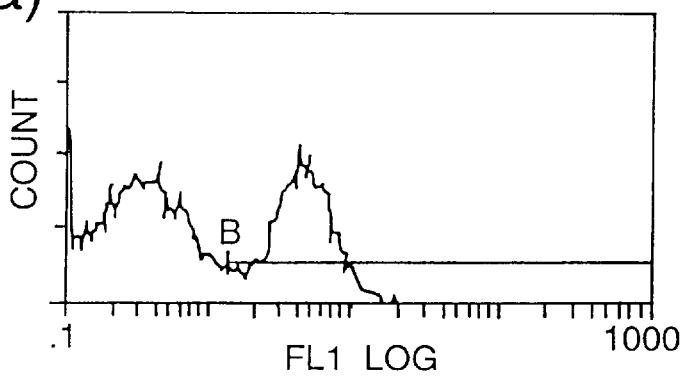
(a)
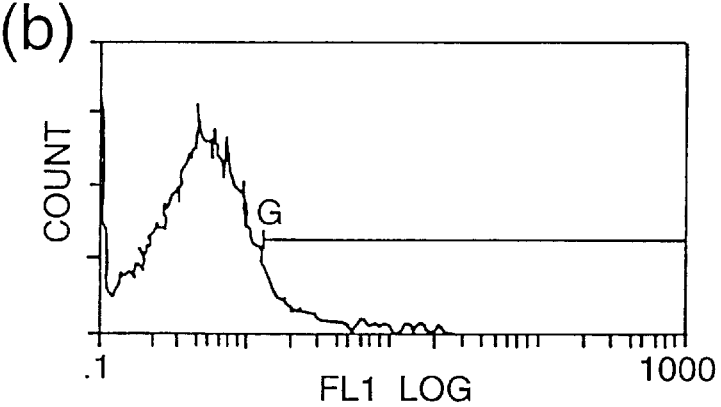
(b)
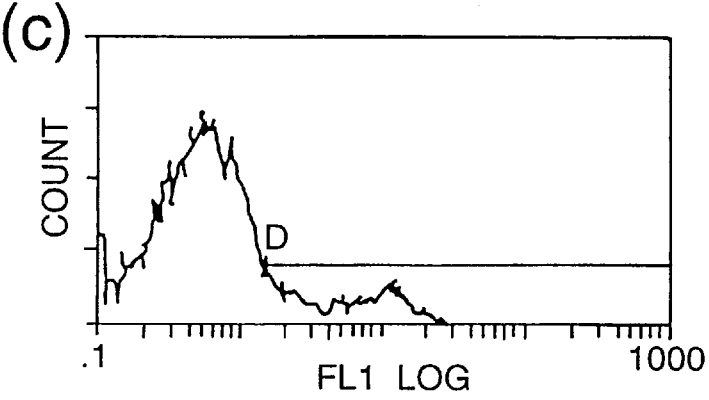
(c)

Fig.7 (Cont).
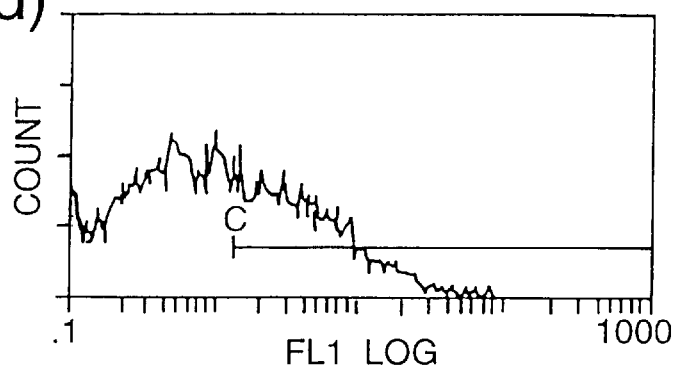
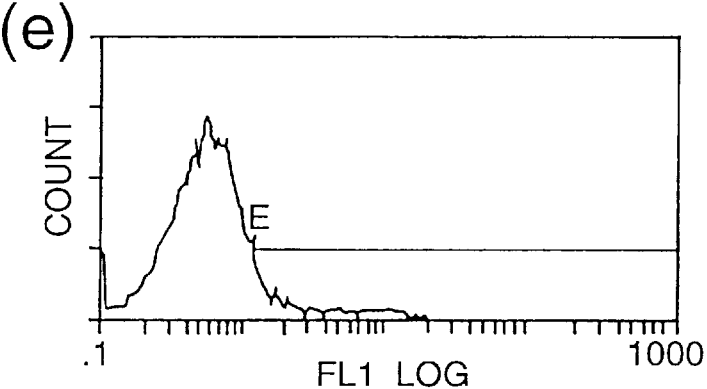
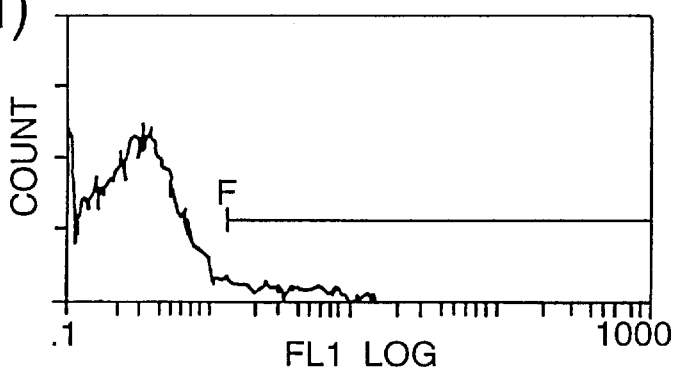
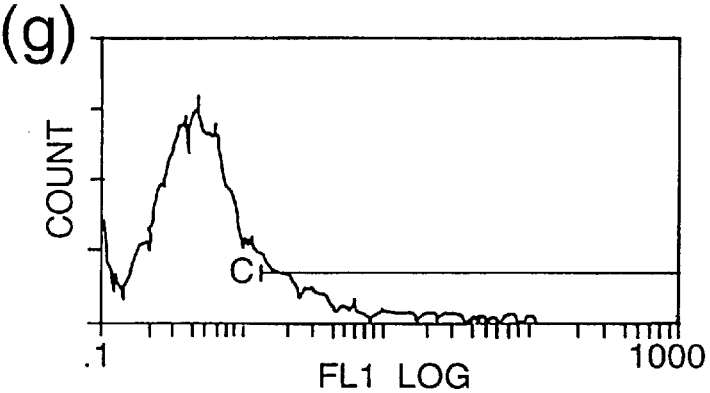

Figure 8

```
ATG CTT CTA GAC AAT TGT GAG GAG GTT TAT CTT GTG AAA AAA TTA
                                             V   K   K   L
    XbaI
                        _____ CAT LEADER _____
TTA TTC GCA ATT CCT TTA GTT GTT CCT TTC TAT GCG GCC CAG CCG
 L   F   A   I   P   L   V   V   P   F   Y   A   A   Q   P
                                                      SfiI

GCC ATG GCC CAG GTG CAG CTG CAG GTC GGC CTC GAG ATC AAA CGG
 A   M   A   Q   V   Q   L   Q   V   G   L   E   I   K   R
                         PstI                XhoI

_____ myc tag _____
GCG GCC GCA GAA CAA AAA CTC ATC TCA GAA GAG GAT CTG AAT GGG
 A   A   A   E   Q   K   L   I   S   E   E   D   L   N   G
 NotI _____ his tag _____
GCC TGT CAT CAC CAT CAT CAC CAT TAA TAA GAA TTC
 A   C   H   H   H   H   H   H   *   *
                                         EcoRI
```

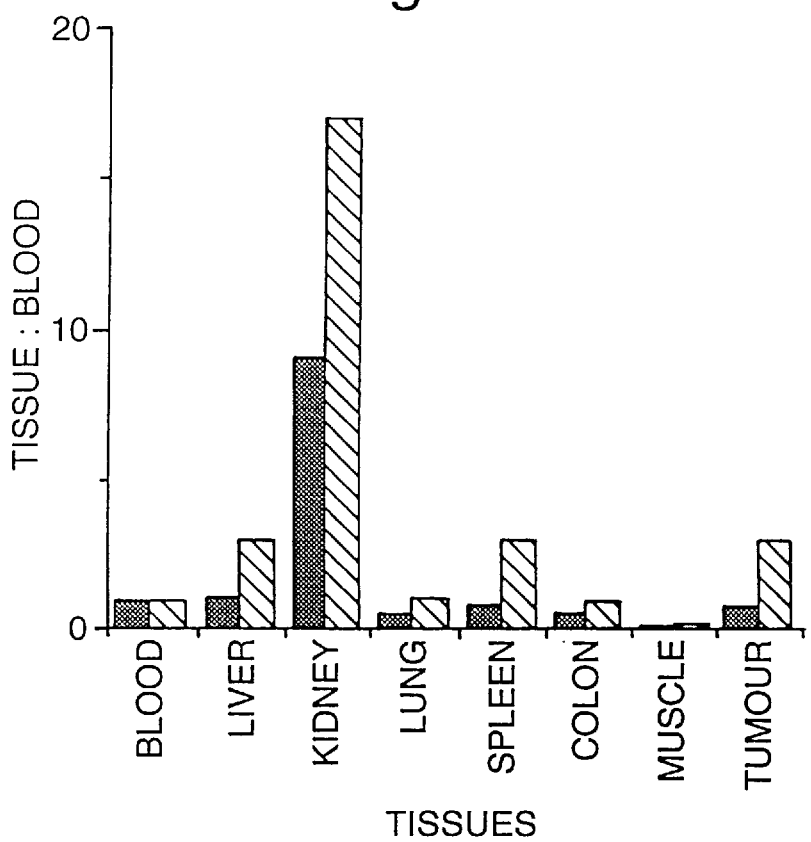

Figure 11

```
GCG GCC CAG CCG GCC ATG GCC CAG GTG CAG CTG CAG GTC
 A   A   Q   P   A   M   A   Q   V   Q   L   Q   V
        SfiI                            PstI

GGC CTC GAG ATC AAA CGG GCG GCC GCA GGT GCG CCG GTG
 G   L   E   I   K   R   A   A   A   G   A   P   V
    XhoI                    NotI

E tag
CCG TAT CCG GAT CCG CTG GAA CCG CGT GCC GCA CAT CAC
 P   Y   P   D   P   L   E   P   R   A   A   H   H his tag
CAT CAT CAC CAT TAA TAA GAA TTC
 H   H   H   H   O   O
                        EcoRI
```

```
(SEQ ID NO:25)  CEA6     CAGGTTCAGCTGGTTCAGTCTCTGGGGCTGAGGTGAAGAAGCCTGGGTCCTC
(SEQ ID NO:44)  T06D10   ---------------------------------------------------
(SEQ ID NO:44)  T06D11   ---------------------------------------------------
(SEQ ID NO:45)  HBA11    ---------------------------------------------------
(SEQ ID NO:46)  HBB11    ---------------------------------------------------
(SEQ ID NO:47)  HBB6     ---------------------------------------------------
(SEQ ID NO:25)  T06D4    ---------------------------------------------------
(SEQ ID NO:25)  T06D8    ---------------------------------------------------
(SEQ ID NO:25)  T06D12   ---------------------------------------------------
(SEQ ID NO:25)  L0B1C    ---------------------------------------------------
(SEQ ID NO:25)  L0E17    ---------------------------------------------------
(SEQ ID NO:25)  L0SC2    ---------------------------------------------------
```

| | | |
|---|---|---|
| (SEQ ID NO: 25) | CEA6 | GGTGAAGGTCTCCTGCAAGGCTTCTGGAGGCACCTTCAGCAACTCTCCTA |
| (SEQ ID NO: 44) | T06D10 | ------------------------------------------------- |
| (SEQ ID NO: 44) | T06D11 | ------------------------------------------------- |
| (SEQ ID NO: 45) | HBA11 | ------------------------------------------------- |
| (SEQ ID NO: 46) | HBB11 | ------------------------------------------------- |
| (SEQ ID NO: 47) | HBB6 | ------------------------------------------------- |
| (SEQ ID NO: 25) | T06D4 | ------------------------------------------------- |
| (SEQ ID NO: 25) | T06D8 | ------------------------------------------------- |
| (SEQ ID NO: 25) | T06D12 | ------------------------------------------------- |
| (SEQ ID NO: 25) | L0B1C | ------------------------------------------------- |
| (SEQ ID NO: 25) | L0E17 | ------------------------------------------------- |
| (SEQ ID NO: 25) | L0SC2 | ------------------------------------------------- |

FIG. 12(A) (B)

```
(SEQ ID NO:25) CEA6      TCAACTGGCTGCGACAGGCCCCGGACAAGGGCTTGAGTGGGATGGGAAGT
(SEQ ID NO:44) T06D10    --------------------------------------------------
(SEQ ID NO:44) T06D11    --------------------------------------------------
(SEQ ID NO:45) HBA11     --------------------------------------------------
(SEQ ID NO:46) HBB11     --------------------------------------------------
(SEQ ID NO:47) HBB6      --------------------------------------------------
(SEQ ID NO:25) T06D4     --------------------------------------------------
(SEQ ID NO:25) T06D8     --------------------------------------------------
(SEQ ID NO:25) T06D12    --------------------------------------------------
(SEQ ID NO:25) L0B1C     --------------------------------------------------
(SEQ ID NO:25) L0E17     --------------------------------------------------
(SEQ ID NO:25) L0SC2     --------------------------------------------------
```

FIG. 12(A)(c)

```
(SEQ ID NO:25) CEA6      ATCATCCCTTCCTTTGGTACAGCAAACTACGCTCAGAAGTTCCAGGGCAG
(SEQ ID NO:44) T06D10    --------------------------------------------------
(SEQ ID NO:44) T06D11    --------------------------------------------------
(SEQ ID NO:45) HBA11     --------------------------------------------------
(SEQ ID NO:46) HBB11     --------------------------------------------------
(SEQ ID NO:47) HBB6      --------------------------------------------------
(SEQ ID NO:25) T06D4     --------------------------------------------------
(SEQ ID NO:25) T06D8     --------------------------------------------------
(SEQ ID NO:25) T06D12    --------------------------------------------------
(SEQ ID NO:25) L0B1C     --------------------------------------------------
(SEQ ID NO:25) L0E17     --------------------------------------------------
(SEQ ID NO:25) L0SC2     --------------------------------------------------
```

FIG. 12(A) (b)

| | | |
|---|---|---|
| (SEQ ID NO:25) | CEA6 | ACTCACGATTACCGCGGACGAATCCACGAGCACAGCCTACATGGAGCTGA |
| (SEQ ID NO:44) | T06D10 | ------------------------------------------------- |
| (SEQ ID NO:44) | T06D11 | ------------------------------------------------- |
| (SEQ ID NO:45) | HBA11 | ------------------------------------------------- |
| (SEQ ID NO:46) | HBB11 | ------------------------------------------------- |
| (SEQ ID NO:47) | HBB6 | ------------------------------------------------- |
| (SEQ ID NO:25) | T06D4 | ------------------------------------------------- |
| (SEQ ID NO:25) | T06D8 | ------------------------------------------------- |
| (SEQ ID NO:25) | T06D12 | ------------------------------------------------- |
| (SEQ ID NO:25) | L0B1C | ------------------------------------------------- |
| (SEQ ID NO:25) | L0E17 | ------------------------------------------------- |
| (SEQ ID NO:25) | L0SC2 | ------------------------------------------------- |

FIG. 12(A)(E)

| | | |
|---|---|---|
| (SEQ ID NO: 25) | CEA6 | GCAGCCTGAGATCTGAGGACACGGGCCCGTGTATTACTGTGCGGGACGGAGC |
| (SEQ ID NO: 44) | R06D10 | ---------------------------------------------T-TTCT |
| (SEQ ID NO: 44) | T06D11 | ---------------------------------------------T-TTCT |
| (SEQ ID NO: 45) | HBA11 | ---------------------------------------------GCT-AT |
| (SEQ ID NO: 46) | HBB11 | ----------------------------------------A---AT-AT |
| (SEQ ID NO: 47) | HBB6 | ---------------------------------------------T--T |
| (SEQ ID NO: 25) | T06D4 | ---------------------------------------------- |
| (SEQ ID NO: 25) | T06D8 | ---------------------------------------------- |
| (SEQ ID NO: 25) | T06D12 | ---------------------------------------------- |
| (SEQ ID NO: 25) | L0B1C | ---------------------------------------------- |
| (SEQ ID NO: 25) | L0E17 | ---------------------------------------------- |
| (SEQ ID NO: 25) | L0SC2 | ---------------------------------------------- |

FIG. 12(A)(F)

```
(SEQ ID NO:25) CEA6     CACAACTACGAACTCTACTACTACTACATGGACGTCTGGGGCCAGGGGAC
(SEQ ID NO:44) R06D10   --T--T--T--G--T-----------------------------------
(SEQ ID NO:44) T06D11   --T--T--T--G--T-----------------------------------
(SEQ ID NO:45) HBA11    TCTTGTA-TAGGTCT-----------------------------------
(SEQ ID NO:46) HBB11    --T--T--T--G--T----------------------C------------
(SEQ ID NO:47) HBB6     --T-CT--T--G--T-----------------------------------
(SEQ ID NO:25) T06D4    --------------------------------------------------
(SEQ ID NO:25) T06D8    --------------------------------------------------
(SEQ ID NO:25) T06D12   --------------------------------------------------
(SEQ ID NO:25) L0B1C    --------------------------------------------------
(SEQ ID NO:25) L0E17    --------------------------------------------------
(SEQ ID NO:25) L0SC2    --------------------------------------------------
```

```
(SEQ ID NO:25) CEA6    AATGGTCACCGTCTCGAGT
(SEQ ID NO:44) T06D10  -------------------
(SEQ ID NO:44) T06D11  -------------------
(SEQ ID NO:45) HBA11   -------------------
(SEQ ID NO:46) HBB11   -------------------
(SEQ ID NO:47) HBB6    -------------------
(SEQ ID NO:25) T06D4   -------------------
(SEQ ID NO:25) T06D8   -------------------
(SEQ ID NO:25) T06D12  -------------------
(SEQ ID NO:25) L0B1C   -------------------
(SEQ ID NO:25) L0E17   -------------------
(SEQ ID NO:25) L0SC2   -------------------
```

| | | |
|---|---|---|
| (SEQ ID NO.29) | CEA6 | GACATCCAGATGACCCAGTCTCCTTCCACCCTGTCTGCATCTATTGGAGA |
| (SEQ ID NO.29) | T06D10 | -------------------------------------------------- |
| (SEQ ID NO.48) | T06D11 | -------GTG--------------------------------GTA----- |
| (SEQ ID NO.29) | HBA11 | -------------------------------------------------- |
| (SEQ ID NO.29) | HBB11 | -------------------------------------------------- |
| (SEQ ID NO.29) | HBB6 | -------------------------------------------------- |
| (SEQ ID NO.49) | T06D4 | -------GTG--------------------------------GTA----- |
| (SEQ ID NO.50) | T06D8 | -------GTG----------------------------------------- |
| (SEQ ID NO.48) | T06D12 | -------GTG--------------------------------GTA----- |
| (SEQ ID NO.51) | L0B1C | --------------------------------------------GTA--- |
| (SEQ ID NO.52) | L0B17 | -------------------------------------------------- |
| (SEQ ID NO.51) | L0SC2 | -------------------------------------------------- |

| | | CAGAGTCACCATCACCTGCCGGGCCAGTGAGGGTATTTATCACTGGTTGG |
|---|---|---|
| (SEQ ID NO.29) | CEA6 | ------------------------------------------------- |
| (SEQ ID NO.29) | T06D10 | ------------------------------------------------- |
| (SEQ ID NO.48) | T06D11 | -----------------------C------------AG-AG--------- |
| (SEQ ID NO.29) | HBA11 | ------------------------------------------------- |
| (SEQ ID NO.29) | HBB11 | ------------------------------------------------- |
| (SEQ ID NO.29) | HBB6 | ------------------------------------------------- |
| (SEQ ID NO.49) | T06D4 | -----------------------C------------AG-AG--------- |
| (SEQ ID NO.50) | T06D8 | -----------------------C------------AG-AG--------- |
| (SEQ ID NO.48) | T06D12 | -----------------------C------------AG-AG--------- |
| (SEQ ID NO.51) | L0B1C | ------------------------------------------------- |
| (SEQ ID NO.52) | L0B17 | ------------------------------------------------- |
| (SEQ ID NO.51) | L0SC2 | ------------------------------------------------- |

FIG. 12(B) (B)

| | | CCTGGTATCAGCAGAAGCCAGGGAAAGCCCCTAAACTCCTGATCTATAAG |
|---|---|---|
| (SEQ ID NO.29) | CEA6 | |
| (SEQ ID NO.29) | T06D10 | ------------------------------------------------- |
| (SEQ ID NO.48) | T06D11 | ------------------------------------------------- |
| (SEQ ID NO.29) | HBA11 | ------------------------------------------------- |
| (SEQ ID NO.29) | HBB11 | ------------------------------------------------- |
| (SEQ ID NO.29) | HBB6 | ------------------------------------------------- |
| (SEQ ID NO.49) | T06D4 | ------------------------G-------------GG--------- |
| (SEQ ID NO.50) | T06D8 | ------------------------G-------------GG--------- |
| (SEQ ID NO.48) | T06D12 | ------------------------------------------------- |
| (SEQ ID NO.51) | LOB1C | ------------------------------------------------- |
| (SEQ ID NO.52) | LOB17 | ------------------------------------------------- |
| (SEQ ID NO.51) | LOSC2 | ------------------------------------------------- |

FIG. 12(B) (C)

| | | |
|---|---|---|
| (SEQ ID NO.29) CEA6 | GCCTCTAGTTTAGCCAGTGGGGCCCCATCAAGGTTCAGCGGGCAGTGGATC | |
| (SEQ ID NO.29) T06D10 | ------------------------------------------------- | |
| (SEQ ID NO.48) T06D11 | ------------------------------------------------- | |
| (SEQ ID NO.29) HBA11 | ------------------------------------------------- | |
| (SEQ ID NO.29) HB11 | ------------------------------------------------- | |
| (SEQ ID NO.29) HBB6 | ------------------------------------------------- | |
| (SEQ ID NO.49) T06D4 | ------C-----AAGTC----T--------------------------- | |
| (SEQ ID NO.50) T06D8 | ------C-----AA---C---T--------------------------- | |
| (SEQ ID NO.48) T06D12 | ------------------------------------------------- | |
| (SEQ ID NO.51) L0B1C | ------------------------------------------------- | |
| (SEQ ID NO.52) L0B17 | ------------------------------------------------- | |
| (SEQ ID NO.51) L0SC2 | ------------------------------------------------- | |

FIG. 12(B)(D)

| | | |
|---|---|---|
| (SEQ ID NO.29) | CEA6 | TGGGACAGATTTCACTCTCTCACCATCAGCAGCCTGCAGCCTGATGATTTG |
| (SEQ ID NO.29) | T06D10 | ------------------------------------------------- |
| (SEQ ID NO.48) | T06D11 | ------------------------------------------------- |
| (SEQ ID NO.29) | HBA11 | ------------------------------------------------- |
| (SEQ ID NO.29) | HBB11 | ------------------------------------------------- |
| (SEQ ID NO.29) | HBB6 | ------------------------------------------------- |
| (SEQ ID NO.49) | T06D4 | ----------------------------A-------A------------ |
| (SEQ ID NO.50) | T06D8 | ----------------------------A-------A------------ |
| (SEQ ID NO.48) | T06D12 | ------------------------------------------------- |
| (SEQ ID NO.51) | L0B1C | ------------------------------------------------- |
| (SEQ ID NO.52) | L0E17 | ------------------------------------------------- |
| (SEQ ID NO.51) | L0SC2 | ------------------------------------------------- |

FIG. 12(B)(E)

| | | |
|---|---|---|
| (SEQ ID NO.29) | CEA6 | CAACTTATTACTGCCAACAATATAGTAATTATCCGCTCACTTTCGGCGGA |
| (SEQ ID NO.29) | T06D10 | -------------------------------------------------- |
| (SEQ ID NO.48) | T06D11 | -------------------------------------------------- |
| (SEQ ID NO.29) | HBA11 | -------------------------------------------------- |
| (SEQ ID NO.29) | HBB11 | -------------------------------------------------- |
| (SEQ ID NO.29) | HBB6 | -------------------------------------------------- |
| (SEQ ID NO.49) | T06D4 | ------------C-----------------AG--TAC-G-ACC---TGG---------CA- |
| (SEQ ID NO.50) | T06D8 | ------------C-----------------AG--TAC-G-ACC---TGG---------CA- |
| (SEQ ID NO.48) | T06D12 | -------------------------------------------------- |
| (SEQ ID NO.51) | L0B1C | ------------------------------AG--TAC-G-ACT------------------ |
| (SEQ ID NO.52) | L0E17 | ------------------------------GA--A---GCT-------------------- |
| (SEQ ID NO.51) | L0SC2 | ------------------------------AG--TAC-G-ACT------------------ |

FIG. 12(B)(F)

```
(SEQ ID NO.29) CEA6      GGGACCAAGCTGGAGATCAAACGT
(SEQ ID NO.29) T06D10    ------------------------
(SEQ ID NO.48) T06D11    ------------------------
(SEQ ID NO.29) HBA11     ------------------------
(SEQ ID NO.29) HBB11     ------------------------
(SEQ ID NO.29) HBB6      ------------------------
(SEQ ID NO.49) T06D4     ------------------------
(SEQ ID NO.50) T06D8     ------------------------
(SEQ ID NO.48) T06p12    ------------------------
(SEQ ID NO.51) L0B1C     ------------------------
(SEQ ID NO.52) L0E17     ------------------------
(SEQ ID NO.51) L0SC2     ------------------------
```

FIG. 12(B) (G)

SPECIFIC BINDING MEMBERS, MATERIALS AND METHODS

CROSS-REFERENCE TO RELATED APPLICATION

This application is a continuation-in-part of U.S. patent application Ser. No. 08/244,597, still pending, filed on Jun. 1, 1994, which is the U.S. National Phase of PCT/GB92/02240.

BACKGROUND OF THE INVENTION

This invention relates to specific binding members for human carcinoembryonic antigen (CEA) and materials and methods relating thereto.

CEA is a tumour-associated glycoprotein, the expression of which is increased in a number of human carcinomas. CEA is a widely used clinical tumour marker, and antibodies raised against it have been used for imaging (Goldenberg, D. M. Int. J. of Biol. Markers 1992, 7; 183–188) and therapy (e.g. Ledermann et al., Int. J. Cancer 1991, 47; 659–664). CEA is a member of the immunoglobulin superfamily and has homology with a number of other antigens, such as normal cross-reacting antigen (NCA), found on normal tissues (Buchegger, F. et al., 1984, Int. J. Cancer 33; 643–649.).

A number of mouse anti-CEA antibodies exist binding to a range of epitopes on CEA (Hammarstrom et al., 1989, Cancer Res. 49, 4852–4858) and human anti-CEA antibodies have been isolated from human phage display libraries (A.D. Griffiths et al. EMBO J. 12, 1993; 725–734; A. D. Griffiths et al. EMBO J. 13 3245–3260, 1994; WO93/11236) The present invention results from the inventors having obtained the first example of human anti-CEA antibodies with a dissociation constant of less than 10 nM for CEA ($1\times10^{-8}$M) and the first which do not cross-react with cell types which express NCA or with a normal human liver cell line.

Herein it is shown that large universal phage display libraries may be used as a source of human antibodies specific for human CEA. Human antibodies to human CEA with improved properties can then be engineered in a number of ways. In Example 1 it is demonstrated how the affinity of the human anti-CEA antibody can be improved by oligonucleotide directed mutagenesis of the complementarity determining regions (CDR's) of the VH and VL domains of the antibodies. The use of antibody chain shuffling is also demonstrated, for instance combining the VH domains of antibodies derived from one library with the VL domains of another library, thus expanding the pool of VL partners tested for each VH domain. Example 1 also demonstrates the use of this procedure, or a combination of oligonucleotide mutagenesis and VL chain shuffling, to generate new antibodies which have an altered specificity on a range of normal tissues compared to the parental antibody. The antibodies also have an improved affinity for human CEA compared with the parental antibody. It is demonstrated that this procedure is capable of changing the specificity of the original antibody in such a way as to improve its potential performance as a specific tumour targeting agent. Cross-reactivity to a human cell line of normal liver cells is greatly reduced with certain combinations of VH and VL.

The use of anti-CEA antibodies in the treatment and diagnosis of cancer has been the subject of a number of patents (e.g. Matsuoka and Kuroki (1989) Patent no. 4871834; Buchegger and Mach (1991) JP Patent no. 5047507; Chester et al 1995, WO 95/15341). The human antibodies disclosed herein should be valuable for similar applications with the advantage that they will enable the use of repeat treatments due to the absence of the human anti-mouse antibody (HAMA) response (Schroff et al (1985) Cancer Res 45: 879–885; DeJager et al (1988) Proc. Am. Assoc. Cancer Res. 29:377). HAMA responses have a range of effects, from neutralisation of the administered antibody leading to a reduced therapeutic dose, through to allergic responses, serum sickness and renal impairment.

It is shown herein that the human antibodies against human CEA can be effective in tumour localisation in a mouse xenograft model of human adenocarcinoma.

TERMINOLOGY

Specific binding member

This describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. This application is concerned with antigen-antibody type reactions.

Antibody

This describes an immunoglobulin whether natural or partly or wholly synthetically produced. The term also covers any polypeptide or protein having a binding domain which is, or is homologous to, an antibody binding domain. These can be derived from natural sources, or they may be partly or wholly synthetically produced. Examples of antibodies are the immunoglobulin isotypes and their isotypic subclasses; fragments which comprise an antigen binding domain such as Fab, scFv, Fv, dAb, Fd; and diabodies.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CHI domains; (iii) the Fv fragment consisting of the VL and VH domains of a single antibody; (iv) the dAb fragment (Ward, E. S. et al., Nature 341, 544–546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423–426, 1988; Huston et al, PNAS USA, 85, 5879–5883, 1988); (viii) bispecific single chain Fv dimers (PCT/US92/09965) and (ix) "diabodies", multivalent or multispecific fragments constructed by gene fusion (WO94/13804; P. Holliger et al Proc. Natl. Acad. Sci. USA 90 6444–6448, 1993).

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways (Holliger, P. and Winter G. Current Opinion Biotechnol. 4, 446–449 (1993)), eg prepared chemically or from hybrid hybridomas, or may be any of the bispecific antibody fragments mentioned above. It may be preferable to use scFv dimers or diabodies rather than whole antibodies. Diabodies and scFv can be constructed without an Fc region, using only variable domains, potentially reducing the effects of anti-idiotypic reaction. Other forms of bispecific antibodies include the single chain "Janusins" described in Traunecker et al, Embo Journal, 10, 3655–3659, (1991).

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected.

Antigen binding domain

This describes the part of an antibody which comprises the area which specifically binds to and is complementary to part or all of an antigen. Where an antigen is large, an antibody may only bind to a particular part of the antigen, which part is termed an epitope. An antibody binding domain may be provided by one or more antibody variable domains. Preferably, an antigen binding domain comprises an antibody light chain variable region (VL) and an antibody heavy chain variable region (VH).

Specific

This refers to the situation in which one member of a specific binding pair will not show any significant binding to molecules other than its specific binding partner. The term is also applicable where eg an antigen binding domain is specific for a particular epitope which is carried by a number of antigens, in which case the specific binding member carrying the antigen binding domain will be able to bind to the various antigens carrying the epitope.

Functionally equivalent variant form

This refers to a molecule (the variant) which although having structural differences to another molecule (the parent) retains some significant homology and also at least some of the biological function of the parent molecule, e.g. the ability to bind a particular antigen or epitope. Variants may be in the form of fragments, derivatives or mutants. A variant, derivative or mutant may be obtained by modification of the parent molecule by the addition, deletion, substitution or insertion of one or more amino acids, or by the linkage of another molecule. These changes may be made at the nucleotide or protein level. For example, the encoded polypeptide may be a Fab fragment which is then linked to an Fc tail from another source. Alternatively, a marker such as an enzyme, flourescein, etc, may be linked.

SUMMARY OF THE INVENTION

The present invention generally provides a specific binding member (comprising a polypeptide) which comprises a human antibody antigen binding domain which is specific for human CEA.

In one aspect, the binding domain has a dissociation constant for human CEA which is less than $1.0 \times 10^{-8}$M, preferably less than $5.0 \times 10^{-9}$M.

A specific binding member comprising a human antibody antigen binding domain specific for human carcinoembryonic antigen wherein the binding domain has a dissociation constant for human carcinoembryonic antigen which is less than $1.0 \times 10^{-8}$M may comprise a binding domain comprising a pairing of VH and VL domains selected from:

i) the VH domain of CEA6, the amino acid sequence of which is shown in FIG. 1(a)(SEQ ID NO: 1), and the VL domain of CEA6, the amino acid sequence for which is shown in FIG. 1(b)(SEQ ID NO: 2);

ii) the VH domain of CEA6, the amino acid sequence of which is shown in FIG. 1(a)(SEQ ID NO: 1), and a VL domain selected from T06D4, T06D8 and T06D12, the amino acid sequences of which are shown in FIG. 4(SEQ ID NOS:3–5, respectively);

iii) the VL domain of CEA6, the amino acid sequence of which is shown in FIG. 1(b)(SEQ ID NO: 2), and a VH domain selected from T06D10, HBA11, HBB11 and HBB6, the amino acid sequences of which are shown in FIG. 2(SEQ ID NOS:6–9, respectively); and iv) that of T06D11, i.e. the VH domain of T06D10, the amino acid sequence of which is shown in FIG. 2(SEQ ID NO: 6), and the VL domain of T06D12, the amino acid sequence of which is shown in FIG. 4(SEQ ID NO: 5).

In another aspect, the specific binding member does not or does not significantly bind to or cross-react with human liver cells, for example a human liver cell line. There may be low cross-reactive binding with human liver cells provided it is not significant compared with the binding to human CEA. Thus, the specific binding member may be substantially non-crossreactive with human liver cells. Likewise, it may not bind or significantly bind other normal tissues or cells such as vascular endothelium, muscle, neutrophils, erythrocytes or lymphocytes. The lack of reactivity with normal lymphocytes and neutrophils is indicative that there is not a high level of crossreactivity with NCA.

A specific binding member comprising a human antibody antigen binding domain specific for human carcinoembryonic antigen, wherein the binding domain is substantially non-cross-reactive with human liver cells may comprise a pairing of VH and VL domains selected from:

i) the VH domain of CEA6, the amino acid sequence of which is shown in FIG. 1(*a*) (SEQ ID NO: 1), and a VL domain selected from T06D4 and T06D12, the amino acid sequences of which are shown in FIG. 4(SEQ ID NOS:3 & 5);

ii) the VL domain of CEA6, the amino acid sequence of which is shown in FIG. 1(*b*)(SEQ ID NO: 2), and the VH domain of T06D10, the amino acid sequence of which is shown in FIG. 2 (SEQ ID NO: 6); and iii) that of T06D11, i.e. the VH domain of T06D10, the amino acid sequence of which is shown in FIG. 2(SEQ ID NO: 6), and the VL domain of T06D12, the amino acid sequence of which is shown in FIG. 4(SEQ ID NO: 5).

The specific binding member may bind cell-associated CEA or soluble CEA. It may bind preferentially to cell-associated CEA.

A specific binding members comprising a human antibody antigen binding domain specific for human carcinoembryonic antigen, wherein the binding domain binds to cell-associated human carcinoembryonic antigen preferentially over soluble human carcinoembryonic antigen may comprise a pairing of VH and VL domains selected from:

i) the VH domain of CEA6, the amino acid sequence of which is shown in FIG. 1(*a*)(SEQ ID NO: 1), and the VL domain of CEA6, the amino acid sequence for which is shown in FIG. 1(*b*)(SEQ ID NO: 2);

ii) the VH domain of CEA6, the amino acid sequence of which is shown in FIG. 1(*a*)(SEQ ID NO: 1), and a VL domain selected from T06D4 and T06D12, the amino acid sequences of which are shown in FIG. 4(SEQ ID NOS: 3 & 5);

iii) the VL domain of CEA6, the amino acid sequence of which is shown in FIG. 1(*b*)(SEQ ID NO: 2), and a VH domain selected from T06D10 and HBB11, the amino acid sequences of which are shown in FIG. 2(SEQ ID NOS: 6 & 8); and iv) that of T06D11, i.e. the VH domain of T06D10, the amino acid sequence of which is shown in FIG. 2(SEQ ID NO: 6), and the VL domain of T06D12, the amino acid sequence of which is shown in FIG. 4(SEQ ID NO: 5).

A specific binding member according to a further aspect of the present invention is specific for a carbohydrate epitope of human CEA. Examples include specific binding members comprising the VH and VL pairing of any of CEA1, CEA2, CEA3, CEA4 and CEA5, the amino acid sequences of the VH domains of which are shown in FIG. 1(*a*) (SEQ ID NO: 10–14, respectively) and the amino acid sequences of the VL domains of which are shown in FIG. 1(*b*) (SEQ ID NO: 15 (CEA1–3), 16 (CEA5 & 5), and 2 (CEA6 & 7).

In a further aspect the present invention provides a specific binding member comprising a human antibody antigen binding domain which specifically binds, preferably the A3-B3 extracellular domain of human CEA. Such a specific binding member may comprise a pairing of VH and VL domains selected from:

i) the VH domain of CEA6, the amino acid sequence of which is shown in FIG. 1(*a*)(SEQ ID NO: 1), and the VL domain of CEA6, the amino acid sequence for which is shown in FIG. 1(*b*)(SEQ ID NO: 2);

ii) the VH domain of CEA6, the amino acid sequence of which is shown in FIG. 1(*a*)(SEQ ID NO: 1), and a VL domain selected from T06D4, T06D8 and T06D12, the amino acid sequences of which are shown in FIG. 4(SEQ ID NO: 3–5, respectively);

iii) the VL domain of CEA6, the amino acid sequence of which is shown in FIG. 1 (*b*) (SEQ ID NO: 2), and a VH domain selected from HBA11, HBB11 and HBB6, the amino acid sequences of which are shown in FIG. 2(SEQ ID NO: 7–9, respectively);

iv) that of T06D11, i.e. the VH domain of T06D10, the amino acid sequence of which is shown in FIG. 2(SEQ ID NO: 6), and the VL domain of T06D12, the amino acid sequence of which is shown in FIG. 4(SEQ ID NO: 5); and v) the VH domain of CEA6, the amino acid sequence of which is shown in FIG. 1(*a*)(SEQ ID NO: 1), and a VL domain selected from LOB1C(SEQ ID NO: 17), LOE17 and LOSC2(SEQ ID NOS: 18 & 17, respectively), the amino acid sequences of which are shown in FIG. 3.

The specific binding member may be in the form of an antibody fragment such as single chain Fv (scFv). Other types of antibody fragments may also be utilised such as Fab, Fab', F(ab')2, Fabc, Facb or a diabody (G. Winter and C. Milstein Nature 349, 293–299,1991; WO94/13804). The specific binding member may be in the form of a whole antibody. The whole antibody may be in any of the forms of the antibody isotypes eg IgG, IgA, IgD, IgE and IgM and any of the forms of the isotype subclasses eg IgG1 or IgG4.

The specific binding member may also be in the form of an engineered antibody e.g. a bispecific antibody molecule (or a fragment such as F(ab')2) which has one antigen binding arm (i.e. specific domain) against CEA and another arm against a different specificity, or a bivalent or multivalent molecule.

In addition to antibody sequences, the specific binding member may comprise other amino acids, e.g. forming a peptide or polypeptide, or to impart to the molecule another functional characteristic in addition to ability to bind antigen. For example, the specific binding member may comprise a label, an enzyme or a fragment thereof and so on.

The binding domain may comprise part or all of a VH domain encoded by a germ line segment or a re-arranged gene segment. The binding domain may comprise part or all of a VL kappa domain or a VL lambda domain.

The binding domain may comprise a VH1, VH3 or VH4 gene sequence of one of the following germ lines: the DP71 germ line; the DP47 germ line; the DP67 germ line; the DP32 germ line; the DP10 germ line or the DP14 germ line; or a re-arranged form thereof. The 'DP' nomenclature is described in Tomlinson I. M. et al, (1992) J. Mol. Biol. 227: 776–798.

The binding domain may comprise a V11, V13 or Vk1 gene sequence of one of the following germ lines: the germ line DPL5; the DPL2 germ line; the germ line DPL16; the germ line L12a; or a re-arranged form thereof.

The binding domain may comprise part or all of a VH domain having any amino acid sequence shown in FIG. 1 (*a*) (SEQ ID NOS: 1, 10–14, & 19) or a functionally equivalent variant form of the said amino acid sequence.

In particular, the binding domain may comprise one or more CDR (complementarity determining region) with an amino acid sequence identified in FIG. 1 (*a*) as a CDR1, CDR2 or CDR3. In a preferred embodiment, the binding domain comprises a CDR3 sequence shown in FIG. 1(*a*). Functionally equivalent variant forms of the CDRs are encompassed by the present invention, in particular variants which differ from the CDR sequences shown by addition, deletion, substitution or insertion of one or more amino acids and which retain ability to bind CEA and optionally one or more of the preferred characteristics for specific binding members of the present invention as disclosed herein. Particularly preferred variant sequences of CEA6 VH are shown in FIG. 2(SEQ ID NO: 6–9). In a preferred embodiment of the present invention a specific binding member includes a CDR3 sequence shown in FIG. 2 (or a functionally equivalent variant form thereof). The specific binding member may comprise all or part of the framework regions shown flanking and between the CDRs in FIG. 2, or different framework regions including modified versions of those shown. If either of the CDR3 sequences of "HBA11" and "HBB11" (FIG. 2) is employed (for example), the specific binding member may comprise an arginine (R) residue in the position shown (FIG. 2) in whatever framework region is employed.

The binding domain may comprise part or all of a VL domain having any amino acid sequence shown in FIG. 1 (b) (SEQ ID NOS: 2, 15 & 16) or a functionally equivalent variant form of the said amino acid sequence.

In particular, the binding domain may comprise one or more CDR (complementarity determining region) with an amino acid sequence identified in FIG. 1 (b) as a CDR1, CDR2 or CDR3. In a preferred embodiment, the binding domain comprises a CDR3 sequence shown in FIG. 1(b). Functionally equivalent variant forms of the CDRs are encompassed by the present invention, in particular variants which differ from the CDR sequences shown by addition, deletion, substitution or insertion of one or more amino acids and which retain ability to bind CEA and optionally one or more of the preferred characteristics for specific binding members of the present invention as disclosed herein. Particularly preferred variant sequences of CEA6 VL are shown in FIG. 3 (SEQ ID NOS: 17 & 18) and FIG. 4(SEQ ID NO: 3–5). In a preferred embodiment of the present invention a specific binding member includes a CDR3 sequence shown in FIG. 3 or FIG. 4 (or a functionally equivalent variant form thereof). The specific binding member may comprise all or part of the framework regions shown flanking and between the CDRs in FIG. 3 or FIG. 4, or different framework regions including modified versions of those shown. Preferred framework modifications are shown in FIG. 4 and these modified framework regions may or may not be used (but may be preferred for use) with one or more of the CDR sequences of "T06D4", "T06D8" or "T06D12" shown in FIG. 4.

So-called "CDR-grafting" in which one or more CDR sequences of a first antibody is placed within a framework of sequences not of that antibody, e.g. of another antibody is disclosed in EP-B-0239400, which has an equivalent US patent.

A specific binding member according to the invention may be one which competes with any specific binding member which binds CEA and comprises part of all of any of the sequences shown in FIG. 1 (a) (SEQ ID NOS: 1, 10–14, & 19), FIG. 1 (b) (SEQ ID NOS: 2, 15 & 16), FIG. 2(SEQ ID NOS: 6–9), FIG. 3(SEQ ID NOS: 17 & 18) and FIG. 4(SEQ ID NOS: 3–5) for binding to CEA. For example, such a specific binding member may compete with TO6D11 or CEA6 for binding to the A3-B3 domain of CEA, or compete with CEA1 for binding to a carbohydrate epitope of CEA. Competition between binding members may be assayed easily in vitro, for example by tagging a specific reporter molecule to one binding member which can be detected in the presence of other untagged binding member (s), to enable identification of specific binding members which bind the same epitope or an overlapping epitope.

Specific binding members according to the invention may be provided in isolated and/or purified form.

The present invention provides the use of a specific binding member as above to use as a diagnostic reagent for forms of human cancer e.g. adenocarcinoma of colon, lung or breast.

The specific binding member for CEA may be used as an imaging agent which may be used to specifically demonstrate the presence and location of CEA-expressing tumours. The present invention provides a method of determining the presence of a CEA-expressing cell or tumour, the method comprising contacting cells with a specific binding member as provided and determining the binding of the specific binding member to the cells. The method may be performed in vivo, or in vitro on a test sample of cells removed from the body.

The present invention provides a method comprising causing or allowing binding of a specific binding member as as provided herein to human CEA. Such binding may take place in vitro or in vivo. If the binding is in vivo, the method may comprise administration of the specific binding member to a mammal, one or more individuals. As demonstrated experimentally herein, specific binding members according to the invention bind human CEA on xenografts in mice, providing a useful experimental model for study for research and development purposes of the specific binding members and their properties.

The reactivities of antibodies on a cell sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, eg via a peptide bond or non-covalently. Linkage via a peptide bond may be as a result of recombinant expression of a gene fusion encoding antibody and reporter molecule.

One favoured mode is by covalent linkage of each antibody with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The mode of determining binding is not a feature of the present invention and those skilled in the art are able to choose a suitable mode according to their preference and general knowledge.

The signals generated by individual antibody-reporter conjugates may be used to derive quantifiable absolute or relative data of the relevant antibody binding in cell samples (normal and test). In addition, a general nuclear stain such as propidium iodide may be used to enumerate the total cell population in a sample, allowing the provision of quantitative ratios of individual cell populations relative to the total cells. When a radionucleotide such as $^{125}$I, $^{111}$In or $^{99m}$Tc is attached to an antibody, if that antibody localises preferentially in tumour rather than normal tissues, the presence of radiolabel in tumour tissue can be detected and quantitated using a gamma camera. The quality of the tumour image obtained is directly correlated to the signal:noise ratio. A review of cancer imaging with CEA antibodies is provided by Goldenberg D. M. ibid.

Experimental use of $^{125}$I and $^{99m}$Tc is exemplified herein.

The present invention also provides for the use of a specific binding member as above to use as a therapeutic reagent, for example when coupled, bound or engineered as a fusion protein to possess an effector function. A specific binding member according to the present invention may be used to target a toxin, radioactivity, T-cells, killer cells or other molecules to a tumour expressing CEA.

Accordingly, further aspects of the invention provide methods of treatment comprising administration of a specific binding member as provided, pharmaceutical compositions comprising such a specific binding member, and use of such a specific binding member in the manufacture of a medicament for administration, for example in a method of making a medicament or pharmaceutical composition comprising formulating the specific binding member with a pharmaceutically acceptable excipient.

In accordance with the present invention, compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, eg decisions on dosage etc, is within the responsibility of general practitioners and other medical doctors. Appropriate doses of antibody are well known in the art; see Ledermann J. A. et al. (1991) Int J. Cancer 47: 659–664; Bagshawe K. D. et al. (1991) Antibody, Immunoconjugates and Radiopharmaceuticals 4: 915–922.

A composition may be administered alone or in combination with other treatments, either simultaneously or sequentially dependent upon the condition to be treated.

Pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, anti-oxidants and/or other additives may be included, as required.

A specific binding member according to the present invention may be made by expression from encoding nucleic acid. Nucleic acid encoding any specific binding member as provided itself forms an aspect of the present invention, as does a method of production of the specific binding member which method comprises expression from encoding nucleic acid therefor. Expression may conveniently be achieved by culturing under appropriate conditions recombinant host cells containing the nucleic acid.

The nucleic acid may encode any of the amino acid sequences shown in FIG. 1a and FIG. 1(b), or any functionally equivalent form. The nucleotide sequences employed may be any of those shown in FIG. 1(a) (SEQ ID NOS: 19–26) or FIG. 1(b) (SEQ ID NOS: 27–29), or may be a variant, allele or derivative thereof. Changes may be made at the nucleotide level by addition, substitution, deletion or insertion of one or more nucleotides, which changes may or may not be reflected at the amino acid level, dependent on the degeneracy of the genetic code.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells and many others. A common, preferred bacterial host is *E. coli*.

The expression of antibodies and antibody fragments in prokaryotic cells such as *E. coli* is well established in the art. For a review, see for example Plückthun, A. Bio/Technology 9: 545–551 (1991). Expression in eukaryotic cells in culture is also available to those skilled in the art as an option for production of a specific binding member, see for recent reviews, for example Reff, M. E. (1993) Curr. Opinion Biotech. 4: 573–576; Trill J. J. et al. (1995) Curr. Opinion Biotech 6: 553–560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, *Molecular Cloning: a Laboratory Manual:* 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Short Protocols in Molecular Biology*, Second Edition, Ausubel et al. eds., John Wiley & Sons, 1992. The disclosures of Sambrook et al. and Ausubel et al. are incorporated herein by reference.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

Following production of a specific binding member it may be used for example in any of the manners disclosed herein, such as in the formulation of a composition such as a pharmaceutical, or a diagnostic product, such as a kit comprising in addition to the specific binding member one or more reagents for determining binding of the member to cells, as discussed.

Further aspects of the invention and embodiments will be apparent to those skilled in the art. In order that the present invention is fully understood, the following examples are provided by way of exemplification only and not by way of limitation. Reference is made to the following figures:

BRIEF DESCRIPTION OF THE DRAWINGS

FIG. 1 shows nucleotide and amino acid sequences of (FIG. 1a) the VH genes (SEQ ID NOS: 1, 10–14 & 19–24) and (FIG. 1b) the VL genes (SEQ ID NOS: 2, 15 & 16, 27–29) of antibodies specific for CEA.

FIG. 1(a): Sequence alignment of CEA-specific scFvs derived from an unimmunised human library. The top panel of the figure shows the amino acid sequences of the VH genes of clones CEA1->7 inclusive (SEQ ID NOS: 14–14, 1 & 19, respectively); the bottom panel shows the nucleotide sequences of the same clones (SEQ ID NOS: 20–26, respectively). CDR=complementarity determining region.

FIG. 1(b): Sequence alignment of CEA-specific scFvs derived from an unimmunised human library. The top panel of the figure shows the amino acid sequences of the VL genes of clones CEA1->7 inclusive (SEQ ID NOS: 2, 15 & 16); the bottom panel shows the nucleotide sequences of the same clones. Identical sequences between clones (SEQ ID NOS: 27–29) are indicated by dots.

FIG. 2 shows the sequences (SEQ ID NOS: 6–9) of clones derived from CEA6 by mutagenesis of VH CDR3. Aligned amino acid sequences of the VH genes of CEA6 and four clones derived from mutagenesis of the heavy chain CDR3. Identical sequences between clones are indicated by dots.

FIG. 3 shows the sequences (SEQ ID NOS: 17 & 18) of clones derived from CEA6 by mutagenesis of VL CDR3. Aligned amino acid sequences of the VL genes of CEA6 and three clones derived from mutagenesis of the heavy chain CDR3. Identical sequences between clones are indicated by dots.

FIG. 4 shows aligned amino acid sequences of the VL gene of CEA6 and those of three clones derived from light chain shuffling (SEQ ID NOS: 3–5). Identical sequences between clones are indicated by dots.

The most homologous germline gene of each clone is:

| | |
|---|---|
| CEA6 | L12a |
| TO6D4 | DPK9 |
| TO6D8 | DPK9 |
| TO6D12 | Hu102 |

FIG. 5 shows flow cytometry analysis of CEA6 and a selection of CEA6-derived clones on CEA-expressing HeLa cells. The top panel (FIG. 5a) shows background binding of the detecting antibody 9E10 (in the absence of added scFv) to the CEA-expressing cells. All CEA-specific clones demonstrate an approximate 10-fold shift in the number of fluorescent cells (x axis), hence demonstrating anti-CEA scFv binding to these cells. (FIG. 5a—negative control; FIG. 5b—T06D4; FIG. 5c—T06D12; FIG. 5d—HBB11; FIG. 5e—T06D11; FIG. 5f—T06D10; FIG. 5g—CEA6)

Figure 6:
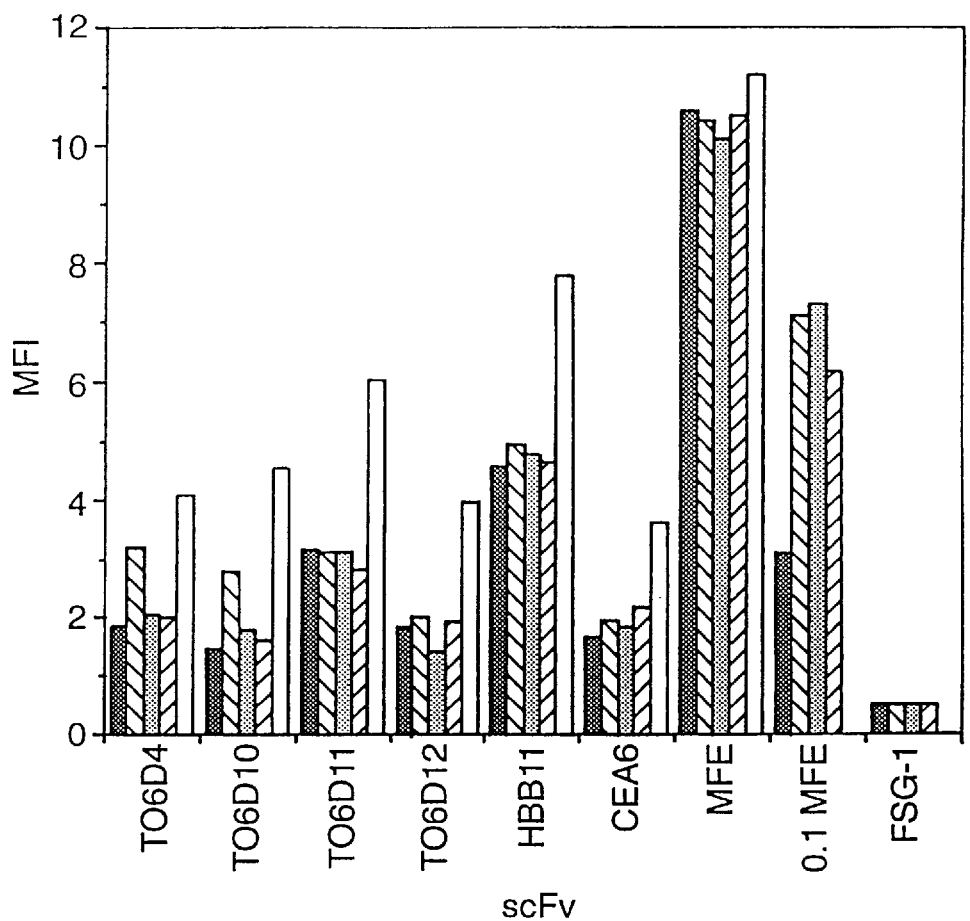

FIG. 6 shows flow cytometry analysis of CEA6 and a selection of CEA6-derived clones on CEA-expressing HeLa cells, measured in the presence of free CEA at concentrations from 0.01 to 1 µg/ml. The figure shows that free CEA is unable to compete anti-CEA scFvs off the CEA-expressing HeLa cells. In contrast, a control antibody (MFE) is competed off the cells at a concentration of 1 µg/ml free CEA. FSG1=negative control. MFI=mean fluorescence intensity.

FIG. 7 shows flow cytometry analysis of CEA6 and a selection of CEA6-derived clones on CEA-negative Chang human liver cells. The top graph (FIG. 7a) demonstrates that a component of CEA6 is binding to the liver cells, whereas (FIG. 7b) TO6D4, (FIG. 7c) TO6D12, (FIG. 7e) TO6D 11, (FIG. 7f) TO6D10 and (FIG. 7g) FSG1 (an unrelated non-CEA specific scFv—negative control) do not bind in the same way. HBB11 (FIG. 7d) shows some cross-reactivity to the liver cells, as demonstrated by the broader peak of fluorescent cells.

FIG. 8 shows cloning sites in the vector pUC119MCH. The vector is based upon pUC 119 and carries the following features: CAT leader sequence (hybrid geneIII-pelB leader); unique NcoI and SfiI 5' cloning sites; unique NotI 3' cloning site; myc tag (for detection with 9E10); single cysteine residue for site-specific labelling; hexahistidine tag for IMAC purification.

FIG. 9 shows tissue to blood ratios (for various tissues) of $^{99m}$Technetium-labelled CEA6 scFv in a mouse xenograft model of human colon adenocarcinoma. Filled bars are values at 3 hours post-injection, and shaded bars are values at 24 hours post injection. After 24 hours, the ratio of incorporated radioactivity in the tumour relative to that in the blood is approximately 3.0.

Figure 10:
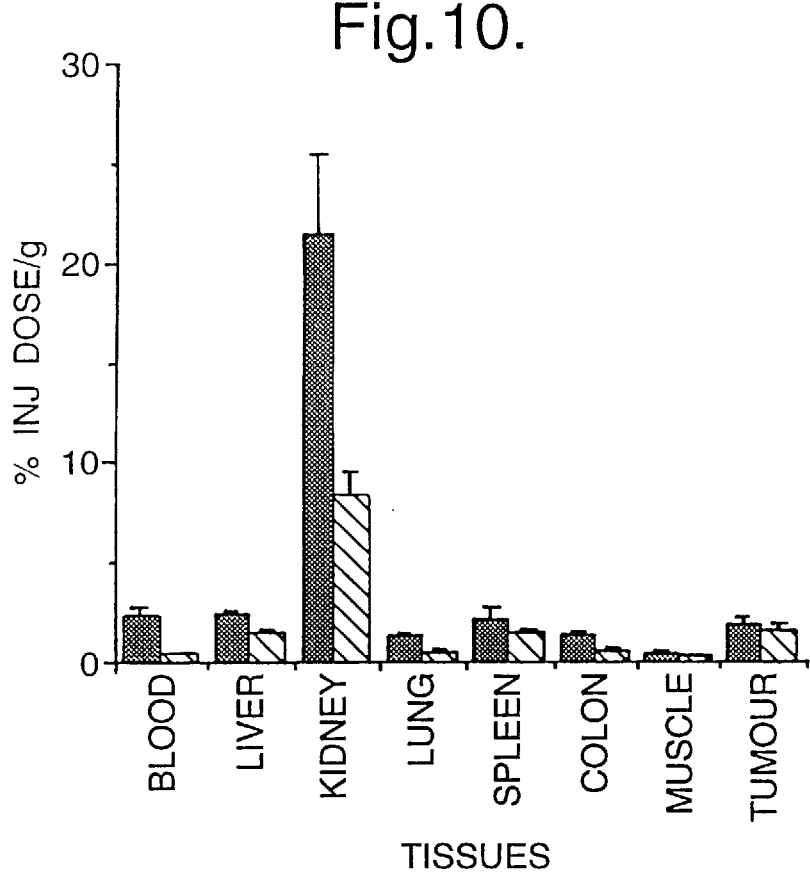

FIG. 10 shows biodistribution (various tissues) of $^{99m}$Technetium-labelled CEA6 at 3 and 24 hours post-injection in the mouse xenograft model of human colon adenocarcinoma. Filled bars are values at 3 hours post-injection, and shaded bars are values at 24 hours post injection. After 24 hours, between 7 and 8% of the injected dose is found to specifically localise to the tumour.

FIG. 11 shows the cloning sites in the vector pUC119EHIS. The vector is based on pUC119 and carries the following features: unique cloning sites; SfiI, PstI, XhoI, NotI; E tag for detection with ant-E tag antibodies (Pharmacia); hexahistidine tag for IMAC purification.

FIG. 12: FIG. 12(a) shows the nucleotide sequences of a number of VH gene segments (SEQ ID NOS: 25, 44–47); FIG. 12(b) shows the nucleotide sequences of a number of VL gene segments (SEQ ID NOS: 29, 48–52).

Figure 13:
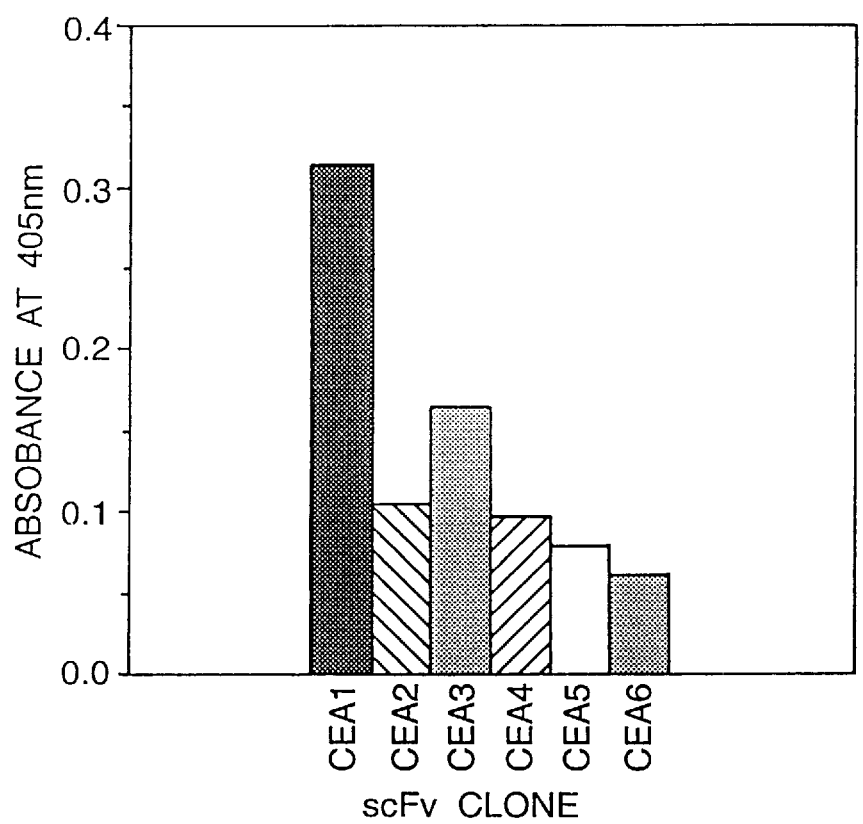

FIG. 13 shows the results of ELISA to assess whether CEA1, CEA2, CEA3, CEA4, CEA5 and CEA6 recognise K1 PSA ($OD_{450}$nm v CEA clone no.).

Figure 14:
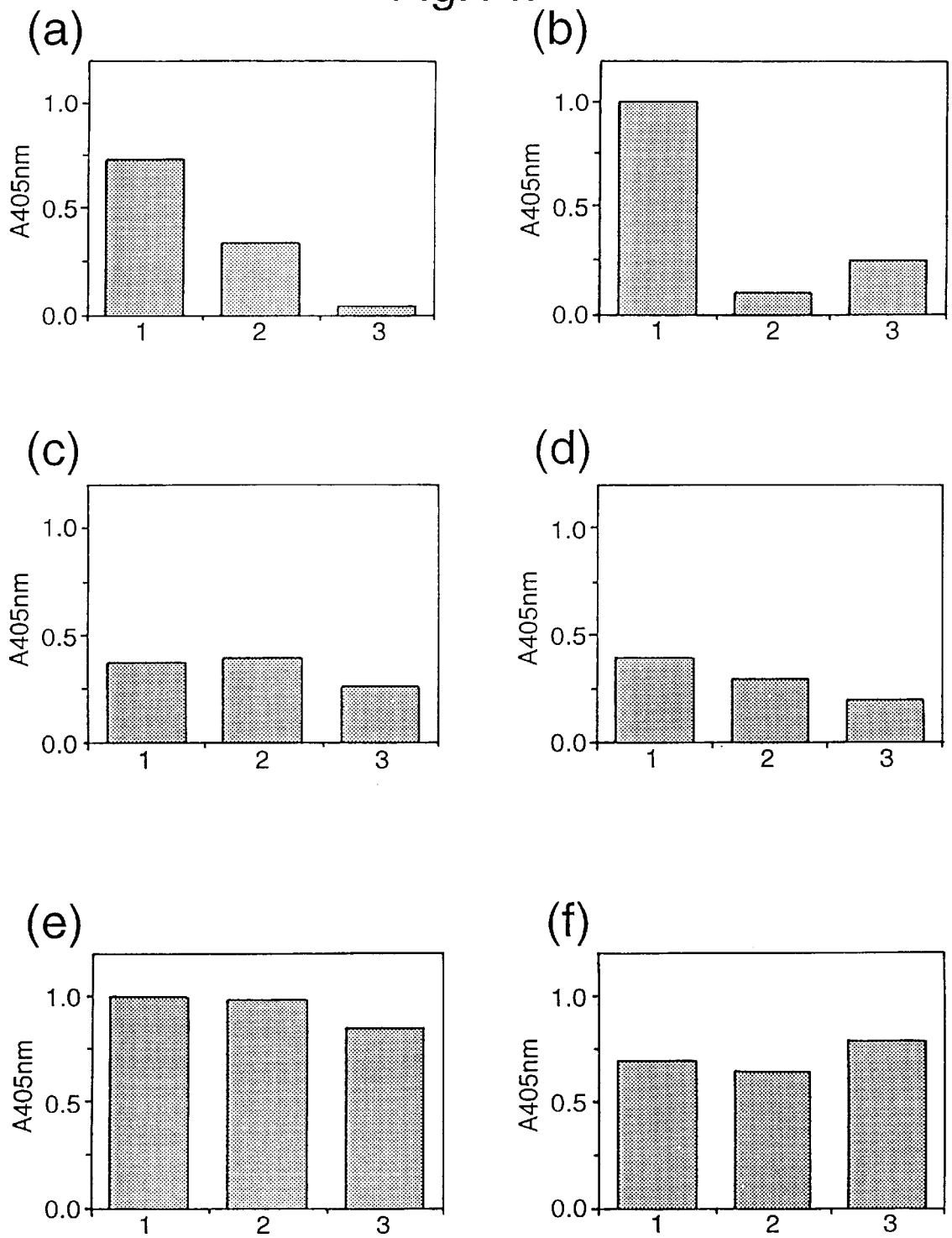

FIG. 14 shows the effect of preincubation with K1 or CA polysialic acid (PSA) on the ability of clones CEA1, CEA2, CEA3, CEA4, CEA5 and CEA6 to bind to immobilised CEA by ELISA. 1=signal on native CEA; 2=signal when scFv is pre-incubated with K; 3=signal when scFv is pre-incubated with CA. (FIG. 14a—CEA1; FIG. 14b—CEA2; FIG. 14c—CEA3; FIG. 14d—CEA4; FIG. 14e—CEA5' FIG. 14f—CEA6.)

All documents mentioned herein are incorporated by reference.

DETAILED DESCRIPTION OF THE DRAWINGS

List of examples

Example 1—Isolation of antibodies specific for CEA.

Example 2—Affinity determination for scFv fragments binding to CEA.

Example 3—Demonstration of binding of antibodies specific for CEA to cell-associated CEA.

Example 4—Demonstration of alteration of specificity of anti-CEA antibodies for a human liver cell line.

Example 5—Epitope mapping of antibodies specific for CEA.

Example 6—In vivo localisation of antibodies specific for CEA to human colon adenocarcinoma xenografts.

Example 7—Further examination of the domain recognition of CEA6 and T06D11.

Example 8—Analysis of the binding specificities of CEA1, CEA2, CEA3, CEA4 and CEA5.

Example 9—Immunocytochemistry of CEA1, CEA2, CEA3, CEA4, CEA5, CEA6 and affinity matured versions of CEA6.

Example 10—Localisation of $I^{125}$—labelled anti-CEA antibodies to human colon adenocarcinoma.

EXAMPLE 1

ISOLATION AND CHARACTERISATION OF ANTIBODIES BINDING TO CEA

1. Identification and characterisation of antibodies to human CEA by selection of an unimmunised phage antibody repertoire.

Antibody repertoire

The following antibody repertoire was used:

Large single chain Fv library derived from lymphoid tissues including tonsil, bone marrow and peripheral blood lymphocytes.

Polyadenylated RNA was prepared from the B-cells of various lymphoid tissues of 43 non-immunised donors using the "Quickprep mRNA Kit" (Pharmacia). First-strand cDNA was synthesized from mRNA using a "First-strand cDNA synthesis" kit (Pharmacia) using random hexamers to prime synthesis. V-genes were amplified using family-specific primers for VH, Vk and Vl genes as previously described (Marks et al. (1991) J. Mol. Biol. 222: 581–597) and subsequently recombined together with the (Gly4, Ser)3 scFv linker by PCR assembly. The VH-linker-VL antibody constructs were cloned into the Sfi I and Not I sites of the phagemid vector, pCANTAB 6. Ligation, electroporation and plating out of the cells was as described previously (Marks et al, supra). The library was made ca. 1000x larger than that described previously by bulking up the amounts of vector and insert used and by performing multiple electroporations. This generated a scFv repertoire that was calculated to have ca. $6.0 \times 10^9$ individual recombinants which by Bst NI fingerprinting were shown to be extremely diverse.

a. Induction of phage antibody library

The phage antibody repertoire above was selected for antibodies to CEA. The repertoire was treated as follows in order to rescue phagemid particles. 500 ml prewarmed (37° C.) 2YTAG (2YT media supplemented with 100 μg/ml ampicillin and 2% glucose) in a 2 1 conical flask was inoculated with approximately $3 \times 10^{10}$ cells from a glycerol stock (−70° C.) culture of the library. The culture was grown at 37° C. with good aeration until the OD600nm reached 0.7 (approximately 2 hours). M13K07 helper phage (Stratagene) was added to the culture to a multiplicity of infection (moi) of approximately 10 (assuming that an OD600nm of 1 is equivalent to $5 \times 10^8$ cells per ml of culture). The culture was incubated stationary at 37° C. for 15 minutes followed by 45 minutes with light aeration (200 rpm) at the same temperature. The culture was centrifuged and the supernatant drained from the cell pellet. The cells were resuspended in 500 ml 2YTAK (2YT media supplemented with 100 μg/ml ampicillin and 50 μg/ml kanamycin), and the culture incubated overnight at 30° C. with good aeration (300 rpm). Phage particles were purified and concentrated by three polyethylene glycol (PEG) precipitations (Sambrook, J., Fritsch, E. F., & Maniatis, T. (1990). Molecular Cloning—A Laboratory Manual. Cold Spring Harbour, New York) and resuspended in PBS to $10^{12}$ transducing units (tu)/ml (ampicillin resistant clones).

b. Panning of phage antibody library on CEA

Phage induced from the repertoire were panned on CEA. A 75mm—12mm immuno tube (Nunc; Maxisorp) was coated with 1 ml of recombinant human CEA (20ug/ml, Genzyme) in PBS overnight at 37 ° C. After washing 3 times with PBS, the tube was filled with 3%MPBS (3% 'Marvel' skimmed milk powder, lx PBS) and incubated for 2 hours at 37° C. for blocking. The wash was repeated, phagemid particles ($10^{13}$ tu) in 1 ml of 3% MPBS were added and the tube incubated stationary at 37° C. for 1 hour. The tube was washed 20 times with PBST (0.1%), then 20 times with PBS. Bound phage particles were eluted from the tube by adding 1 ml of 100 mM-triethylamine, and incubating the tube stationary at room temperature for 10 minutes. The eluted material was immediately neutralised by pipetting into a tube containing 0.5 ml 1M-Tris.HCl (pH7.4). Phage were stored at 4° C. 0.75 ml of the eluted phage were used to infect 10 ml of logarithmically growing E. coli TG1 (Gibson, T. J. (1984). PhD thesis. University of Cambridge, UK.). Infected cells were grown for 1 hour at 37° C. with light aeration in 2YT broth, and then plated on 2YTAG medium in 243mm×243mm dishes (Nunc). Plates were incubated overnight at 30° C. Colonies were scraped off the plates into 10 ml of 2YT broth and 15% (v/v) glycerol added for storage at −70° C.

Glycerol stock cultures from the first round of panning the repertoire on CEA were rescued using helper phage to derive phagemid particles for the second round of panning. 250 μl of glycerol stock was used to inoculate 50 ml 2YTAG broth, and incubated in a 250 mL conical flask at 37° C. with good aeration until the OD600 nM reached 0.7 (approximately 2 hours). M13K07 helper phage (moi=10) was added to the culture which was then incubated stationary at 37° C. for 15 minutes followed by 45 minutes with light aeration (200 rpm) at the same temperature. The culture was centrifuged and the supernatant drained from the cell pellet. The cells were resuspended in 50 ml prewarmed 2YTAK, and the culture incubated overnight at 30° C. with good aeration. Phage particles were purified and concentrated by PEG precipitation (Sambrook et al., 1990) and resuspended in PBS to $10^{13}$ tu/ml.

Phage induced from the first round of panning the repertoire was selected a second time as described above. The process of phage growth and panning was repeated over a third and a fourth round of selection.

c. Growth of single selected clones for immunoassay

Individual colonies from the third and fourth round selections were used to inoculate 100 μl 2YTAG into individual wells of 96 well tissue culture plates (Corning). Plates were incubated at 30° C. overnight with moderate shaking (200 rpm). Glycerol to 15% was added to each well and these master plates stored at −70° C. until ready for analysis.

d. ELISA to identify anti-CEA scFv

Clones specific for CEA were identified by ELISA, using scFv displayed on phage or soluble scFv.

i. Phage ELISA

Cells from the master plates were used to inoculate fresh 96 well tissue culture plates containing 100 μl 2YTAG per well. These plates were incubated at 37° C. for 6–8 hours or until the cells in the wells were growing logarithmically (OD600 0.2–1.0). M13K07 was added to each well to an moi of 10 and incubated stationary for 15 min then 45 min with gentle shaking (100 rpm), both at 37° C. The plates were centrifuged at 2000 rpm for 10 min and the supernatant removed. Each cell pellet was resuspended in 100 μl 2YTAK and incubated at 30° C. overnight.

Each plate was centrifuged at 2000 rpm and the 100 μl supernatant from each well recovered and blocked in 20 μl 18%M6PBS (18% skimmed milk powder, 6×PBS), stationary at room temperature for 1 hour. Meanwhile, flexible microtitre plates which had been blocked overnight stationary at 37° C. with either 100 μl 0.5 μg/ml CEA in PBS or 100 μl PBS alone (giving an uncoated control plate), were washed 3 times in PBS and blocked for 2 h stationary at room temperature in 3MPBS. These plates were then washed three times with PBS and 50 μl preblocked phage added to each well of both the CEA-coated or uncoated plate. The plates were incubated stationary at 37° C. for 1 h after which the phage were poured off. The plates were washed by incubating for 2 min in PBST three times followed by incubating for 2 min in PBS three times, all at room temperature.

To each well of both the CEA-coated and the uncoated plate, 50 μl of a 1 in 10 000 dilution of sheep anti-fd antibody (Pharmacia) in 3MPBS was added and the plates incubated at 37° C. stationary for 1 h. Each plate was washed as described above and 50 μl of a 1 in 5 000 dilution donkey anti-sheep alkaline phosphatase conjugate (Sigma) in 3MPBS added and incubated stationary at 37° C. for 1 h. Plates were washed as described as above followed by two rinses in 0.9% NaCl. Alkaline phosphatase activity was visualised using either the chromagenic substrate pNPP (Sigma) or the Ampak system (Dako). The absorbance signal generated by each clone was assessed by measuring the optical density at either 405 nm (PNPP) or 492 nm (Ampak) using a microtitre plate reader. Clones were chosen for further analysis if the ELISA signal generated on the CEA-coated plate was at least double that on the uncoated plate.

ii. Soluble ELISA

Cells from the master plates were used to inoculate fresh 96 well tissue culture plates containing 100 μl 2YTAG per well. These plates were incubated at 30° C. for 8 hours then centrifuged at 2000 rpm for 10 min and the supernatant removed. Each cell pellet was resuspended in 100 μl 2YTA containing 10 mM IPTG and incubated at 30° C. overnight.

Each plate was centrifuged at 2000 rpm and the 100 μl supernatant from each cell recovered and blocked in 20 μl 18%M6PBS stationary at room temperature for 1 hour. Meanwhile, flexible microtitre plates which had been blocked overnight stationary at 37° C. with either 100 μl 0.5 μg/ml CEA in PBS or 100 μl PBS alone, were washed 3 times in PBS and blocked for 2 h stationary at 37° C. in 3MPBS. These plates were then washed three times with PBS and 50 μl preblocked soluble scFv added to each well of both the CEA-coated or uncoated plate. The plates were incubated stationary at 37° C. for 1 h after which the scFv solutions were poured off. The plates were washed by incubating for 2 min in PBST three times followed by incubating for 2 min in PBS three times, all at room temperature.

To each well of both the CEA-coated and the uncoated plate, 100 μl of a 1 in 200 dilution of the anti-myc tag murine antibody 9E10 (Munro, S. & Pelham, H. R. B. (1986)Cell 46, 291–300) in 3MPBS was added and the plates incubated at 37° C. stationary for 1 h. Each plate was washed as described above and 100 μl of a 1 in 5000 dilution goat anti-mouse alkaline phosphatase conjugate (Pierce) in 3MPBS added and incubated stationary at 37° C. for 1 h. Plates were washed as described above followed by two rinses in 0.9% NaCl. Alkaline phosphatase activity was visualised using the chromagenic substrate pNPP (Sigma). The absorbance signal generated by each clone was assessed by measuring the optical density at 405 nm (PNPP) using a microtitre plate reader. Clones were chosen for further analysis if the ELISA signal generated on the CEA-coated plate was at least double that on the uncoated plate.

iii. Specificity ELISA

Clones identified as binding CEA rather than an uncoated well, as described above, were further analysed for specificity. Specificity ELISA's were carried out using scFv either displayed on phage or in solution as described above, except that 5 ml of media in 50 ml Falcon tubes were inoculated with each clone and grown to generate the phage or soluble scFv used in the ELISA. Microtitre plate wells were coated with 100 μl of either 0.5 μg/ml CEA, 10 μg/ml bovine serum albumin (BSA), 10 μg/ml ovalbumin, 10 μ/ml lysozyme, 10 μg/ml keyhole limpet haemocyanin (KLH) or PBS (the uncoated well). After preblocking both the phage (or soluble scFv) and the microtitre plates, 50 μl blocked phage (or soluble scFv) from each clone was added to a well coated with either CEA, BSA, ovalbumin, lysozyme, KLH, or an uncoated well. As above, alkaline phosphatase activity was visualised using the chromagenic substrate pNPP (Sigma). Clones were considered to be specific for CEA if the ELISA signal generated in the CEA coated well was at least five-fold greater than the signal on any of the test antigens or an uncoated well.

e. Sequencing of CEA-Specific ScFv Antibodies

The nucleotide sequences of the CEA specific antibodies were determined by first using vector-specific primers to amplify the inserted DNA from each clone. Cells from an individual colony on a 2YTAG agar plate were used as the template for a polymerase chain reaction (PCR) amplification of the inserted DNA using the primers pUC19reverse (SEQ ID NO: 35) and fdtetseq (SEQ ID NO: 30) (Table 1). Amplification conditions consisted of 30 cycles of 94° C. for 1 min, 55° C. for 1 min and 72° C. for 2 min, followed by 10 min at 72° C. The PCR products were purified using a PCR Clean-up Kit (Promega) in to a final volume of 50 μl H20. Between 2 and 5 μl of each insert preparation was used as the template for sequencing using the Taq Dye-terminator cycle sequencing system (Applied Biosystems). The primers mycseq10 (SEQ ID NO: 32) and PCR-L-Link (SEQ ID NO: 33) were used to sequence the light chain of each clone and PCR-H-Link (SEQ ID NO: 34) and pUC19reverse (SEQ ID NO: 35) to sequence the heavy chain (Table 1).

f. Sequence of the Initial CEA-Specific ScFv Antibodies

Seven different CEA specific antibodies were isolated from the selections. Each clone name and its heavy and light chain germline is given below. The complete sequence of each VH and VL domain gene is given in FIG. 1(*a*) (SEQ ID NOS: 20–26) and (*b*) (SEQ ID NO: 27–29).

| CLONE | VH GERMLINE | | VL GERMLINE | |
|-------|-------------|------|-------------|--------|
| CEA1  | VH4         | DP71 | VLambda1    | DPL5/2 |
| CEA2  | VH3         | DP47 | VLambda1    | DPL5/2 |
| CEA3  | VH3         | DP47 | VLambda1    | DPL5/2 |

-continued

| CLONE | VH GERMLINE | | VL GERMLINE | |
| --- | --- | --- | --- | --- |
| CEA4 | VH3 | DP67 | VLambda3 | DPL16 |
| CEA5 | VH3 | DP32 | VLambda3 | DPL16 |
| CEA6 | VH1 | DP10 | VKappa1 | L12a |
| CEA7 | VH1 | DP10 | VKappa1 | L12a |

2. Affinity Maturation of the Initial CEA-Specific ScFv Antibodies a. CDR3 'Spiking' of the CEA-Specific ScFv Antibody CEA6 i. Construction of VH CDR3 'spiked' repertoire

A 63 mer mutagenic oligonucleotide primer, CEA6HCDOP; (SEQ ID NO: 38), was first synthesized (see Table 1). This primer allowed spiking of 7 residues of the CEA6 VH CDR3 using a parsimonious mutagenesis strategy (Ballint and Larrick (1993) Gene 137: 109–118. The CEA6 heavy chain was amplified by PCR using the primers LMB3; (SEQ ID NO: 31)and CEA6HCDOP; (SEQ ID NO: 38). Amplification conditions consisted of 25 cycles of 94° C. for 1 min, 55° C. for 1 min and 72° C. for 1 min, followed by 10 min at 72° C. The PCR product was separated through a 1% agarose-TAE gel, the band representing the amplified VH excised, and eluted from the agarose gel using the Geneclean Kit (Bio 101).

The parental CEA6 light chain was amplified by PCR using the primers fdtetseq and CEA6JH (Table 1; (SEQ ID NOS: 30 & 36, respectively)). Amplification conditions consisted of 25 cycles of 94° C. for 1 min, 55° C. for 1 min and 72° C. for 1 min, followed by 10 min at 72° C. The PCR product was separated through a 1% agarose-TAE gel, the band representing the amplified VL excised, and eluted from the agarose gel using the Geneclean Kit (Bio 101).

Approximately 50 ng amplified 'spiked' CEA6 heavy chain and 50 ng of amplified parental CEA6 light chain were combined. This was used in an assembly amplification after the addition of reaction buffer to 1X, dNTP's to 200 nM and 5 units Taq polymerase. Amplification conditions consisted of 7 cycles of 94° C. for 1 min, 65° C. for 4 min. Five µl of each assembly was used as the template in a 'pull-through' amplification with the primers fdtetseq and LMB3. Amplification conditions consisted of 25 cycles of 94° C. for 1 min, 55° C. for 2 min and 72° C. for 1 min, followed by 10 min at 72° C.

The pull-through amplification product was separated through 1% agarose-TAE and the band representing the pull-through 'spiked' VH-VL excised and eluted using the Geneclean Kit. This was digested with the restriction endonucleases Sfi I and Not I (NEB) and ligated (Amersham ligation system) into the phagemid vector pCantab 6, previously digested with Sfi I and Not I. The ligation product was used to transform electrocompetent TG1 cells, plated out on 2YTAG plates and incubated overnight at 30° C. Approximately $1.1 \times 10^7$ individual clones were generated from this VH CDR3 'spiking' of the CEA6 VH CDR3.

ii. Selection of CEA6 VH CDR3-spiked repertoire

The CEA6 VH CDR3-spiked repertoire was selected for CEA-specific antibodies. Phagemid particles were recovered from the repertoire as described earlier for the initial library. Recovered phage were preblocked for 1 h in a final volume of 100 µl 3MPBS. Approximately $10^{11}$ tu phage were used in the first round selection and between $10^9$ and $10^{10}$ for subsequent selections. For the first round selections, biotinylated CEA to a final concentration of 10 nM was added to the preblocked phage and incubated stationary at 37° C. for 1 h.

For each selection, 100 µl Dynabeads suspension (Dynal) was separated on a magnet and the beads recovered and preblocked for 2 h in 1 ml 3MPBS. The beads were recovered on a magnet and resuspended in the phagemid/biotinylated CEA mixture and incubated at room temperature for 15 min while being turned end-over-end. The beads were captured on a magnet and washed three times with PBST followed by three washes in PBS. After each wash, the beads were captured on a magnet and resuspended in the next wash. Finally, half of the beads were resuspended in 10 µl 50 mM DTT (the other half of the beads stored at 4° C. as a back-up) and incubated at room temperature for 5 min. The whole bead suspension was then used to infect 5 ml logarithmically-growing TG1 cells. This was incubated at 37° C., stationary for 15 min then with moderate shaking for 45 min, plated on 2YTAG plates and incubated overnight at 30° C.

Colonies were scraped off the plates into 10 ml of 2YT broth and 15% (v/v) glycerol added for storage at −70° C.

iii. Identification of CEA-Specific ScFv Antibodies from the CEA6 VH-Spiked Repertoire ScFv antibodies specific to CEA were identified by both phage and soluble ELISA, and sequenced, as described earlier. Four new CEA-specific scFv antibodies were identified. All had the CEA6 light chain sequence (L12a), described earlier and changes in one or more of the 7 targeted spiked residues of the VH. The sequences are given in FIG. 2 (SEQ ID NO: 6–9).

iv. Construction of CEA6 VL/VH CDR3-'spiked' repertoire

A 65 mer mutagenic oligonucleotide primer, CEA6LCDOP (SEQ ID NO: 39), was first synthesized (see Table 1). This primer allowed spiking of 4 residues of the CEA6 VL CDR3 using a parsimonious mutagenesis strategy (Ballint and Larrick, supra). The CEA6 light chain was amplified by PCR using the primers CEA6JH (SEQ ID NO: 36) and CEA6LCDOP (SEQ ID NO: 39). Amplification conditions consisted of 25 cycles of 94° C. for 1 min, 55° C. for 1 min and 72° C. for 1 min, followed by 10 min at 72° C. The PCR product was separated through a 1% agarose-TAE gel, the band representing the amplified VL excised, and eluted from the agarose gel using the Geneclean Kit (Bio 101).

A population of CEA6-derived heavy chains from the 10 nM biotin-CEA selection described above was amplified by PCR using the primers PCRHLINK and LMB3 (Table 1; SEQ ID NO: 34 & 31, respectively). Amplification conditions consisted of 25 cycles of 94° C. for 1 min, 55° C. for 1 min and 72° C. for 1 min, followed by 10 min at 72° C. The PCR product was separated through a 1% agarose-TAE gel, the band representing the amplified VH population excised, and eluted from the agarose gel using the Geneclean Kit (Bio 101).

Approximately 50 ng amplified 'spiked' CEA6 light chain and 50 ng of the amplified parental CEA6 heavy chain population were combined. This was used in an assembly amplification after the addition of reaction buffer to 1X, dNTP's to 200 nM and 5 units Taq polymerase. Amplification conditions consisted of 7 cycles of 94° C. for 1 min, 65° C. for 4 min. Five µl of each assembly was used as the template in a 'pull-through' amplification with the primers fdtetseq and LMB3. Amplification conditions consisted of 25 cycles of 94° C. for 1 min, 55° C. for 2 min and 72° C. for 1 min, followed by 10 min at 72° C.

The pull-through amplification product was separated through 1% agarose-TAE and the band representing the pull-through 'spiked' VH-VL excised and eluted using the Geneclean Kit. This was digested with the restriction endonucleases Sfi I and Not I (NEB) and ligated (Amersham ligation system) into the phagemid vector pCantab 6, previously digested with Sfi I and Not I. The ligation product was used to transform electrocompetent TG1 cells, plated out on 2YTAG plates and incubated overnight at 30° C. Approximately 6×10$^6$ individual clones were generated from this VL CDR3 'spiking' of the CEA6 VL CDR3.

v. Selection of CEA6 VL/VH CDR3-spiked repertoire

The CEA6 VL/VH CDR3-spiked repertoire was selected for CEA-specific antibodies. Phagemid particles were recovered from the repertoire as described earlier for the initial library. Recovered phage were preblocked for 1 h in a final volume of 100 μl 3MPBS. Approximately 10$^{11}$ tu phage were used in the first round selection and between 10$^9$ and 10$^{10}$ for subsequent selections. For the first round selections, biotinylated CEA to a final concentration of 10 nM was added to the preblocked phage and incubated stationary at 37° C. for 1 h.

For each selection, 100 μl Dynabeads suspension (Dynal) was separated on a magnet and the beads recovered and preblocked for 2 h in 1 ml 3MPBS. The beads were recovered on a magnet and resuspended in the phagemid/biotinylated CEA mixture and incubated at room temperature for 15 min while being turned end-over-end. The beads were captured on a magnet and washed three times with PBST followed by two washes in PBS. Selection for clones with a longer off rate than that of CEA6 was then carried out. Beads were washed in PBS containing CEA at a concentration of 50 nM. At various time points (15', 30', 1 hour, 3 hours and 18 hours) the phage captured on the magnetic beads were separated on a magnet and the wash solution was replaced. Finally, half of the beads were resuspended in 10 μl 50 mM DTT (the other half of the beads stored at 4° C. as a back-up) and incubated at room temperature for 5 min. The whole bead suspension was then used to infect 5 ml logarithmically-growing TG1 cells. This was incubated at 37° C., stationary for 15 min then with moderate shaking for 45 min, plated on 2YTAG plates and incubated overnight at 30° C.

vi. Identification of CEA-Specific ScFv Antibodies from the CEA6 VH/VL-Spiked Repertoire ScFv antibodies specific to CEA were identified by both phage and soluble ELISA, and sequenced, as described earlier. Three new CEA-specific scFv antibodies were identified. All three had the CEA6 heavy chain sequence (DP10), described earlier and changes in the 4 targeted spiked residues of the VL. The sequences are given in FIG. 3 (SEQ ID NOS: 17 & 18).

b. Light Chain Shuffling of the CEA-Specific ScFv Antibody CEA6 i. Construction of Repertoire

The population of CEA6 VH CDR3-spiked clones described above was recombined with the complete repertoire of light chains derived from the PBL and tonsil-derived scFv repertoires. The CEA6 VH CDR3-spiked heavy chains were amplified by PCR using the primers PCRHLINK (Table 1; SEQ ID NO: 34) and LMB3 (SEQ ID NO: 31). Amplification conditions consisted of 25 cycles of 94° C. for 1 min, 55° C. for 1 min and 72° C. for 1 min, followed by 10 min at 72° C. The PCR product was separated through a 1% agarose-TAE gel, the band representing the amplified VH excised, and eluted from the agarose gel using the Geneclean Kit (Bio 101).

The tonsil light chains were amplified by PCR using the primers fdtetseq and PCRLLINK (Table 1; SEQ ID NOS: 30 & 33, respectively). Amplification conditions consisted of 25 cycles of 94° C. for 1 min, 55° C. for 1 min and 72° C. for 1 min, followed by 10 min at 72° C. The PCR product was separated through a 1% agarose-TAE gel, the band representing the amplified VL excised, and eluted from the agarose gel using the Geneclean Kit (Bio 101).

Approximately 50 ng amplified CEA6 VH CDR3-spiked heavy chains and 50 ng of amplified tonsil-derived light chains were combined. This was used in an assembly amplification after the addition of reaction buffer to 1X, dNTP's to 200 nM and 5 units Taq polymerase. Amplification conditions consisted of 7 cycles of 94° C. for 1 min, 60° C. for 1 min and 72° C. for 1 min 30 s, followed by 10 min at 72° C. 10 μl of each assembly was used as the template in a 'pull-through' amplification with the primers fdtetseq and LMB3 (SEQ ID NOS: 30 & 31, respectively) Amplification conditions consisted of 25 cycles of 94° C. for 1 min, 60° C. for 1 min and 72° C. for 1 min 30 s, followed by 10 min at 72° C.

The pull-through amplification product was separated through 1% agarose-TAE and the band representing the pull-through VH-VL excised and eluted using the Geneclean Kit. This was digested with the restriction endonucleases Sfi I and Not I (NEB) and ligated (Amersham ligation system) into the phagemid vector pCantab 6, previously digested with Sfi 1 and Not I. The ligation product was used to transform electrocompetent TG1 cells, plated out on 2YTAG plates and incubated overnight at 30° C. Approximately 3×10$^7$ individual clones were generated from the light chain-shuffle of the CEA6 VH CDR3-spiked heavy chains with the tonsil-derived light chains.

ii. Selection of Light Chain Shuffle Repertoire

The light chain-shuffle repertoire was selected for CEA-specific antibodies with longer off rates than CEA6 exactly as described above for the CEA6 VH/VL CDR3-spiked repertoire.

iii. Identification of CEA-Specific ScFv Antibodies from the Light Chain Shuffle Repertoire ScFv antibodies specific to CEA were identified by both phage and soluble ELISA, and sequenced, as described earlier. Three new CEA-specific scFv antibodies were identified. All three had the CEA6 heavy chain sequence (DP10), described earlier. The sequences are summarised below and the complete sequence of each VL domain gene is given in FIG. 4 (SEQ ID NOS: 3–5).

| CLONE | VH GERMLINE | VL ISOTYPE |
| --- | --- | --- |
| TO6D4 | DP10 (CEA6) | VKappa |
| TO6D8 | DP10 (CEA6) | VKappa |
| TO6D12 | DP10 (CEA6) | VKappa |

3. Building higher affinity anti-CEA antibodies

Recombining heavy chains derived from high affinity anti-CEA scFv with light chains derived from anti-CEA scFv showing improved off-rate and reduced human liver cross-reactivity.

Antibodies derived by spiking CDR3 of the scFv antibody CEA6 (section 2b) bind CEA with high affinity. To improve the chance of obtaining higher affinity antibodies it was decided to combine VHs derived from high affinity anti-CEA scFvs with VLs derived from scFv clones with longer off rates and with reduced human liver cross-reactivity. 10 The heavy chain from clone TO6D10 was amplified by PCR using the primers LMB3 and PCR-H-Link (Table 1; SEQ ID NOS: 31 & 34, respectively). Amplification conditions consisted of 25 cycles of 94° C. for 1 min, 55° C. for 1 min and 72° C. for 1 min, followed by 10 min at 72° C. The PCR product was separated through a 1% agarose-TAE gel, the band representing the amplified VH excised, and eluted from the agarose gel using the Geneclean Kit (Bio 101).

Light chains were separately amplified by PCR from the anti CEA-specific clonesTO6D8 and TO6D12 using the primers fdtetseq1 and PCRLLink (Table 1). The same PCR conditions were used as described for theVH amplification. Each VL PCR product was then separately purified through a 1% agarose-TAE gel as described above.

Approximately 50 ng amplified heavy chain and 50 ng of either of the amplified light chains were combined. These were used in assembly amplifications after the addition of reaction buffer, dNTP's to 200 nM and 5 units Taq polymerase. Amplification conditions consisted of 7 cycles of 94° C. for 1 min, 55° C. for 1 min and 72° C. for 2 mins, followed by 10 min at 72° C. 5 µl of assembly was used as the template in a 50 ul 'pull-through' amplification with the primers fdtetseq and LMB3. Amplification conditions consisted of 25 cycles of 94° C. for 1 min, 55° C. for 1 min and 72° C. for 2 mins, followed by 10 min at 72° C.

The pull-through amplification products were separated through 1% agarose-TAE and the bands representing the pull-through VH-VL's excised and eluted using the Geneclean Kit. These were digested with the restriction endonucleases Sfi I and Not I (NEB) and ligated into the phagemid vector pCantab 6, previously digested with Sfi 1 and Not I, using the Amersham ligation system. The ligation products were used to transform electrocompetent TG1 cells, plated out on 2YTAG plates and incubated overnight at 30° C.

c. Identification of recombined clones T06D9 and T06D11.

Clones which possessed the TO6D10 heavy chain in combination with either the TO6D8 light chain (giving clone TO6D9) or the TO6D12 light chain (giving clone TO6D11) were identified by sequencing.

EXAMPLE 2

AFFINITY DETERMINATION FOR SCFV FRAGMENTS BINDING TO CEA

Affinities of all anti-CEA scFv's were determined by surface plasmon resonance, derived from the CEA6 parental clone while affinities of CEA1-5 were measured by binding inhibition ELISA.

a. Affinity determination by suface plasmon resonance

The off-rates for binding to CEA of the scFv fragments described in example 1 were determined using desialylated CEA coupled to the sensor chip. 100 µg of CEA was resuspended in 0.1M sodium acetate buffer pH4.0 and desialylated using 1.375 mU sialidase (Sigma). This was incubated for 4 hours at 37° C. with occasional shaking. The desialylated CEA was then oxidised using 1 unit of galactose oxidase per 500µg of CEA in 10 mM phosphate buffer pH7.0. This was incubated for 2 hours at 36° C. and desalted into 10 mM sodium acetate buffer pH4.0 using a Centricon column. The CEA was then immobilised onto the sensor chip using the aldehyde group. 15 µl EDC/NHS coupling agent (Pierce) was passed over the chip at a flow rate of 5 µl/min. 35 µl of 5 mM hydrazine in water was then passed over the chip, followed by 35 µl of ethanolamine. 4 µl of 60 µg/ml treated CEA was passed over the chip at a flow rate of 2 µl/min followed by 40 µl 0.1M sodium cyanoborohydride in 0.1M acetate buffer pH4.0 at a flow rate of 5 µl/min. Approximately 1500RU (resoname units) of CEA was bound using this method. 5000RU and 800RU CEA chips were made using this procedure. Off-rates were calculated using the Bia-Evaluation software (Pharmacia). Saturation of the chip with purified scFv was demonstrated for each sample before off-rate calculations were performed. On-rates were also calculated using the Bia-Evaluation software and the assumption that scFv preparations were 100% active. Results are shown in Table 2.

b. Affinity measurement by inhibition ELISA

The affinities of CEA 1->5 inclusive could not be evaluated by surface plasmon resonance because these scFvs recognise carbohydrate structures removed by desialylation of CEA. Therefore their affinities were measured by binding inhibition ELISA.

Soluble scFv ELISAs were carried out as described in example 1. A dilution series of the scFv preparations in PBS was made to assess the point at which a signal of approximately 0.2 OD units came up on ELISA overnight. This concentration of scFv was then pre-incubated overnight at 4° C. with native CEA at concentrations ranging from 2 nM to 0.1 nM. The resultant data were plotted as a Klotz plot (y axis=Maximal absorbance/(Maximal absorbance-absorbance at CEA conc. n) x axis=1/CEA conc. n). The gradient of the plot was taken to be the affinity. The results are shown in Table 3.

EXAMPLE 3

DEMONSTRATION OF THE BINDING OF ANTI-CEA ANTIBODIES TO CELL-ASSOCIATED CEA.

a. CEA-expressed on the suface of HeLa cells.

For these experiments metal affinity chromotography (IMAC) purified scFv was used throughout; this was prepared as follows. Colonies were inoculated into 50 ml of 2 TY containing 2% glucose and 100 µg/ml ampicillin (2TY/G/A) and incubated overnight at 30° C. The overnight culture was then added to 500 ml of 2TY/G/A and grown at 30° C. in a shaking incubator for 1 hour. Cells were pelleted at 8 K for 10 minutes, resuspended in 500 ml 2TY containing 1 mM IPTG and 100 µg/ml ampicillin and grown at 22° C. overnight. Perplasmic preparations were made by pelleting the cells at 8 K for 10 minutes in a precooled rotor (4° C.). Pellets were resuspended in 25 ml ice-cold 50 mM Tris-HCl pH8, 20% w/v sucrose, 1 mM EDTA and incubated on ice for 15 minutes. ScFv was then purified from the periplasmic preparation by IMAC using NTA-Agarose (Qiagen) according to the manufacturer's instructions.

$1 \times 10^5$ HeLa cells expressing CEA were incubated for 1 hour at room temperature with 5mg of IMAC-purified anti-CEA scFv or 5 µg of control scFv specific for human foetal haemoglobin (FSG-1), made up to 100 µl in PBS/0.5% w/v BSA (PBS/BSA). Cells were washed once in 10 ml PBS/BSA and incubated with a mouse anti-myc antibody (9E10) at 25 µg/ml in 100 ml PBS/BSA for 1 hour. Cells were washed in 10ml PBSBSA and incubated with a 100 µl of a 1:200 dilution of FITC-conjugated anti-mouse antibody (Sigma) in PBS/BSA. After a final wash in 10 ml PBS/BSA, cell fluorescence was measured by flow cytometry using a Coulter-EPISXL-MCL flow cytometer. $1 \times 10^3$ fluorescence events were measured using the FL1 channel (emission below 550 nM) and were plotted on a log scale against number of cells.

The results for a selection of the off-rate matured anti-CEA scFv's are shown in FIG. 5.

b. Anti-CEA scFv's preferentially bind to cell-associated CEA, rather than soluble CEA.

Flow cytometry analysis was carried out as above expect that soluble CEA was added to the HeLa cells expressing CEA before addition of the scFv. A range of concentrations from 10 ng/ml up to 1 μg/ml was added to the cells (FIG. 6). At none of the concentrations tested did the soluble CEA inhibit binding of scFv to the cells. Addition of soluble CEA was able to inhibit the binding of an unrelated monoclonal antibody of similar affinity to the cells. This suggests that the anti-CEA scFv's preferentially bind cell-associated CEA over soluble CEA.

EXAMPLE 4

DEMONSTRATION OF ALTERATION OF SPECIFICITY OF AFFINITY MATURED ANTI-CEA ANTIBODIES FOR A HUMAN LIVER CELL LINE.

Flow cytometry was carried out exactly as described in Example 3 part a, except that $1 \times 10^5$ Chang human liver cells were incubated with the IMAC-purified anti-CEA scFv's or control scFv. $1 \times 10^3$ fluorescence events were measured using the FL1 channel (emission below 550 nm) and plotted on a log scale against number of cells. The results are shown in FIG. 7.

It can be seen from FIG. 7 that CEA6 is partially cross-reactive with the human liver cell line. HBA11 and HBB11 also give some cross-reactivity, whereas clones which were isolated by selections from the light chain shuffled repertoire have no observable cross-reactivity to the liver cell line in this assay. Thus it has been demonstrated that the selection protocol adopted has enriched for anti-CEA antibodies which have reduced cross-reactivity for human liver.

EXAMPLE 5

EPITOPE MAPPING OF ANTIBODIES SPECIFIC FOR CEA.

a. Expression of full length CEA or CEA epitopes N, A1-B1, A2-B2, A3-B3.

CEA is comprised of an NH2 terminal domain (Domain N) of 108 amino acid residues followed by three highly homologous internal domains (A1-B1, A2-B2, A3-B3) of 178 residues each. The 23 residue C-terminal domain (Domain M) has been shown to be removed post-translationally and replaced with a glycophospholipid moiety that anchors CEA in the cell membrane. cDNA of full length CEA or epitopes N, A1-B1, A2-B2 or A3-B3 as fusion proteins with bacterial CMP-KDO synthetase (CKS) were provided by Dr J. Shively (Hass et al (1991) Cancer Res. 51: 1876–1882).

XL1-Blue cells containing the CKS-CEA genes were cultured as follows. Cultures of 2 ml of 2 TY containing 50 μg/ml ampicillin were inoculated with a single colony. Cultures were incubated for approximately 3 to 4 hours at 37° C. and IPTG was added to a final concentration of 1 mM. Growth was continued for an additional 5 hours, then the cells were pelleted and frozen at −70° C. Cell pellets were resuspended in 3 ml of 10 mM Tris, 1 mM EDTA, pH 10.0. Lysozyme (6 mg) was added and the samples were placed on ice for 15 minutes. 0.3 ml of 20% Triton X-100 were added and the suspension mixed. An additional 3ml of 10 mM Tris, 1 mM EDTA, pH 10.0, were added. The Triton-insoluble fraction was pelleted by centrifugation and resuspended in 6 ml of 8M urea. The urea-soluble material was then dialysed against PBS (0.15M NaCl, 0.02M sodium phosphate, pH 7.2) to yield soluble protein.

b. Epitope mapping of anti-CEA scFv's derived from CEA6

The soluble domains were coated onto ELISA plates at a concentration of 1 μg/ml at 37° C. overnight. Soluble anti-CEA scFv was purified using metal affinity chromatography (IMAC) as described in Example 3 part a. ELISA's were carried out as described in Example 1, except that purified scFv was used at a concentration of approximately 1 μg/ml. All CEA6-derived clones bound preferentially to the A3-B3 domain.

Thus it has been demonstrated that although the specificity for human liver cells has been altered by the affinity maturation procedure this has not altered the broad epitope on CEA recognised by all of the affinity matured clones.

c. Epitope mapping of CEA1, CEA2, CEA3, CEA4 and CEA5

These clones were tested by soluble ELISA for binding to desialiated CEA (prepared as described in Example 2). Treated or untreated CEA was coated onto an ELISA plate at 0.5 μg/ml and the ELISA then carried out as described in Example 1. CEA1, CEA2, CEA3, CEA4 and CEA5 all gave no detectable signal above background (0.1 OD units after 2 hours development) on the desialylated CEA whereas the signals on native CEA were all >0.4 OD units after 2 hours. This demonstrates that this set of clones recognises carbohydrate epitopes on native CEA which can be removed by sialidase treatment. None of the set of clones bound to the expressed CEA epitopes N, A1-B1, A2-B2 or A3-B3 in ELISA's. Since proteins expressed in *E. coli* are not glycosylated, this result confirms the observations with desialylated CEA.

EXAMPLE 6

LOCALISATION OF ANTIBODIES SPECIFIC FOR CEA TO HUMAN COLON ADENOCARCINOMA.

It has been shown in a mouse xenograft model of human colon adenocarcinoma that radiolabelled mouse anti-CEA mAb's localise to the tumour (Pedley, et al. (1991) Int. J. Cancer 47: 597–602). A study was set up to establish whether the anti-CEA scFv antibodies described here are capable to successfully localising to the tumour in such a model.

a. Subcloning of scFv into a cysteine-tagged vector to allow radiolabelling

ScFv inserts of all the anti-CEA antibodies were generated by PCR using the primers LMB3 and ftdseq (SEQ ID NOS: 31 & 30, respectively). Amplification conditions consisted of 25 cycles of 94° C. for 1 min, 55° C. for 1 min and 72° C. for 1 min, followed by 10 min at 72° C. The PCR products were separated through a 1% agarose-TAE gel, the band representing the amplified scFv excised, and eluted from the agarose gel using the Geneclean Kit (Bio 101). The product was digested with the restriction endonucleases Sfi I and Not I (NEB) and ligated (Amersham ligation system) into Sfi I and Not I digested cysteine tagged vector pUC119MCH (FIG. 8). The ligation product was used to transform electrocompetent TG1 cells, plated out on 2TYAG plates and incubated overnight at 30° C. Colonies were picked and the scFv sequenced to check the insert had been correctly incorporated into the pUC119MCH vector.

b. Technetium-99m labelling of IMAC purified scFv.

Anti-CEA scFv's were purified by IMAC, as described in Example 3. These were then radiolabelled with technetium-99m as described in Pak et al (1992), Nucl. Med. Biol. 19; 699–677.

c. Animal model.

Human LS 174T xenografts were established in nude mice by subcutaneous passaging from the human colon adenocarcinoma cell line LS 174T. Groups of 4 mice were taken for each time point. The mice were injected through the tail vein with 20 μg of technetium-99m labelled CEA6 scFv at a specific activity of 3 mCi/mg. Mice were killed either 3 or 24 hours after injection and the biodistribution and tissue:blood ratios of the antibody were measured.

The results obtained for CEA6 scFv are shown in FIG. 9 and FIG. 10. The tumour: blood was calculated to be 3, the tumour: liver was 1.2 and the tumour: normal colon was 3.6 at 24 hours post injection. Thus it has been demonstrated that the anti-CEA scFv CEA6 localises to a human xenografted adenocarcinoma in a nude mouse model of the disease.

EXAMPLE 7

FURTHER EXAMINATION OF THE DOMAIN RECOGNITION OF CEA6 AND TO6D11.

a. Coupling scFv's to a BiaCore chip via the tenninal cysteine residues

Monomer preparations of CEA6 or TO6D11 made in the pUC119MCH vector and hence possessing a terminal cysteine residue were coupled to a CM5 chip (Pharmacia) using a ligand thiol immobilisation method as follows. 50 μl of 50 mM 1-ethyl-3-(3-dimethylamino-propyl) cardodiimide-HCl (EDC) reagent (Pharmacia) and 50 μl of 200 mM N-Hydroxysuccinimide (NHS) reagent (Pharmacia) were mixed and passed over the chip at a flow rate of 5 μl/min. 20 μl of 80 mM 2-(2-pyridinyldithio) ethaneaminehydrochloride (PDEA) activation solution was then passed over the chip at the same flow rate. The PDEA solution was made freshly by dissolving 4.5 mg of PDEA (Sigma) in 250μl of 0.1M borate buffer pH 8.5. 20 μl of an approximately 100 μg/ml solution of purified monomeric scFv was made up to 50 ml with PBS and 50 μl of 50 mM sodium formate pH4 was added to the scFv and 50 μl of this passed over the chip, again at 5 μl/min. 50 mM 1-cysteine-1M NaCl deactivating solution was prepared by dissolving 1.5 mg 1-cysteine and 14 mg NaCl in 250 μl 0.1M sodium formate buffer pH 4.3 and 20 μl of this was injected over the chip at 5 μl/min. This procedure resulted in the immobilisation of 375 Resonance Units (RU's) of TO6D11, and 354 RU's of CEA6 monomer being coupled to this chip. A control chip consisting of a known N-domain reactive scFv was also prepared by the same procedure.

b. Preparation of purified CEA domains.

50 ml cultures of the CEA domains cloned into the pUC119EHIS vector (FIG. 11) were grown overnight at 30° C. in 2 TY containing 2% glucose and 100 μg/ml ampicillin (2TYGA). These cultures were used to inoculate 500 ml of 2 TYGA and were grown at 30° C. for a further hour. Cells were pelleted by centrifugation at 5 K for 10 min and resuspended in 2 TY with 1 mM IPTG and 100 mg/ml ampicillin which had been prewarmed to 30° C. Induction was carried out with shaking for 3 hours at 30° C. and the cells then pelleted as before. Pellets were resuspended in 10 ml of 1×TES (0.2M Tris-HCl, 0.5mM EDTA, 0.5M sucrose) and 15 ml of 0.2×TES then added. Cells were left on ice for 30 min and cell debris then pelleted at 10 K for 30 min at 4° C. in a SS34 rotor. The supernatant was transferred to a 50 ml falcon tube and 25 μl of $MgCl_2$ added. 2 ml Ni-NTA agarose (Quiagen) which had been washed in phosphate buffer was added to the supernatant and rotated at 4° C. for 1 hour. The Ni-NTA agarose was then pelleted by spinning in a bench-top centrifuge at 600 rpm for 2 min and the agarose pellet washed in twice in 20 ml phosphate buffer (300 mM NaCl, 50 mM sodium phosphate pH8), followed by one wash in phosphate buffer containing 10 mM imidazole. The agarose slurry was the transferred to a column and the CEA domains eluted from the column by addition of two aliquots of 1 ml of 300 mM imidazole in phosphate buffer.

c. Binding of CEA domain preparations to the scFv immobilised on the BiaCore chip.

70 μl of each of the four CEA domain preparations (A1-B1, A2-B2, A3-B3 and N) were passed over the scFv-coupled chips at a flow rate of 5 μl/min. After injection of each domain the chip was regenerated by an injection of 10 ml of 10 mM HCl. For the CEA6 and TO6D11 scFv-coupled chips domains A1-B1, A2-B2 and A3-B3 all resulted in around 100 RU's binding to the surfaces. No binding was observed for the N domain on CEA6 or TO6D11 scFv coated chips. $K_{off}$ for the domains were calculated for both CEA6 and TO6D11 scFv coated chips (Table 4) and A3-B3 was found to have the longest off rate, suggesting this domain is the one which 30 is preferentially recognised by CEA6 and TO6D11. Domain A1-B1, A2-B2 and A3-B3 do contain elements which are common to all three domains, which may account for some cross-reactivity of the CEA6 and TO6D11 scFv's with all these domains. This demonstrates that the overall broad domain recognition characteristics of CEA6 have not been altered in the affinity maturation of this antibody to TO6D11.

As a control a chip with a coupled scFv which has been shown to recognise the N domain of CEA was also tested by passing the different domains across the chip. This scFv gave 54 RU's of binding of the N domain preparation and no detectable binding of the other domains to the scFv, demonstrating the activity of the N domain preparation and reaffirming the specificity of this scFv.

EXAMPLE 8

ANALYSIS OF THE BINDING SPECIFICITIES OF CEA1, CEA2, CEA3, CEA4, AND CEA5.

As described in Example 5c CEA1, CEA2, CEA3, CEA4 and CEA5 did not give any detectable ELISA signal when tested for binding to the desialylated portion of CEA, suggesting the clones were recognising the sialic acid residues of CEA. The specificities of these clones was investigated further as follows.

a. Testing CEA1, CEA2, CEA3, CEA4 and CEA5for binding to polysialic acid (PSA) by ELISA.

Biotinylated K1 polysialic acid, a version of PSA which is a polymer of on average approximately 200 monomers of sialic acid, was provided by Dr R Waibel. The K1 version of PSA was purified from the K1strain of E. coli. E. coli K1 possesses a membranous CMP-NeuAc; poly-α-2-8 sialosyl sialyltransferase complex catalyses the synthesis of long linear PSA (K1) chains.

The PSA was coated onto a streptavidin-coated plate (Pierce, Reacti-Bind) at 10 μg/ml at room temperature for 1 hour. The plate was blocked in 3%MPBS for 1 hour at room temperature and 100 μl of monomer preparations of CEA1, CEA2, CEA3, CEA4, CEA5 and CEA6, as a control, in 3%MPBS then added to each well at approximately 100 μg/ml. The plate was left at room temperature for 1 hour, then washed three times in PBST, followed by three times in PBS. Detection of bound scFv was with 1:200 diluted anti-myc tag antibody (9E10) (Munro and Pelham, 1986) for 1 hour at 37° C. The plate was washed as before and the assay developed with 1:5000 diluted alkaline phosphatase conjugated goat anti-mouse IgG (Pierce) at 37° C. for 1 hour. Plates were washed as before, rinsed in 0.9% NaCl and the chromatogenic substrate pNPP (Sigma) was added. The absorbance was measured at 405 nm.

Clones CEA1, CEA2, CEA3, CEA4 and CEA5 all gave a signal on the PSA K1 polymer, whereas CEA6 gave no detectable signal (FIG. 13). These results suggest that CEA1, CEA2, CEA3, CEA4 and CEA5 all recognise free K1 PSA and hence that sialic acid plays a role in their recognition of CEA.

b. Inhibition of binding of CEA1, CEA2, CEA3, CEA4 and CEAS to CEA by free K1. or free colonic acid (CA)

Excess free PSA K1 and free PSA CA (at approximately 1 µM) were preincubated with 100 µl of the scFv monomer preparations (at approximately 100 µg/ml) and the scFv's then used to detect native CEA by ELISA as described in Example 1d(ii). CA is a polymer of sialic acid with an average of approximately 16 sialic acid residues per chain. The signal on native CEA was inhibited to varying extents in the cases of CEA1, CEA2, CEA3, CEA4 and CEA5 for both K1 and CA. Binding of CEA6 to native CEA was not inhibited by the presence of K1 or CA PSA (FIG. 14). A summary of the degree of inhibition of scFv binding to CEA by K1 and CA is shown in Table 5. That the binding of CEA1, CEA2, CEA3, CEA4, and to a lower level CEA5, to CEA was inhibited by the free PSA molecules provides further evidence for the observation that these clones have an element of sialic acid binding specificity in their recognition for CEA.

EXAMPLE 9

IMMUNOCYTOCHEMISTRYOF CEA1, CEA2, CEA3, CEA4, CEA5 AND CEA6 ON NORMAL COLONIC MUCOSA AND COLORECTAL TUMOURS.

Purified monomer preparations of the clones were used to detect CEA expressed in paraffin-embedded formalin-fixed sections from different tissue sources (BioMedix). Sections were de-waxed in Histoclear, then washed twice with 100% ethanol, once with 70% ethanol, rehydrated in distilled water (all 5 min each) and rinsed in PBST. Endogenous alkaline phosphatase activity was then blocked by incubation with 20% acetic acid for 15 min, rinsed with PBST, then blocked for 1 hour in 1%BSA in PBS (PBSB). After rinsing, monomeric scFv fractions diluted in PBSB were applied and incubated in a humidified atmosphere overnight at 4° C. Slides were rinsed three times with PBST (2 min each), then incubated with 1:100 diluted 9E10 in PBSB for 1 hour at room temperature. After rinsing as before, alkaline phosphatase conjugated goat anti-mouse IgG (1:100 diluted in PBS/10% foetal calf serum) was added and the incubation continued for 1 hour. Bound antibody was detected with Fast Red (Sigma) substrate, and the section was counterstained with haematoxylin and mounted.

CEA 1, CEA2, CEA3, CEA4 and CEA5 gave weak staining of normal colonic crypt epithelium and heterogeneous staining of the normal surface epithelium. These five clones gave variable positive staining of moderate to well differentiated adenocarcinomas. Staining in the moderately differentiated tumours was localised to the basal surfaces of glands and at the lumenal aspect. staining in the more well differentiated tumours was confined to the mucin-producing goblet cells. These clones did not give a "classical" anti-CEA staining pattern, which may be explained by their reactivity with carbohydrate elements on CEA which may not be present at all stages in the life cycle of the CEA molecule.

CEA6 gave intense staining of the normal surface epithelium and goblet cells and crypt epithelium were also reactive. Staining of adenocarcinoma by CEA6 gave uniform intense positivity of moderate to well differentiated tumours, but more heterogeneous staining of poorly differentiated carcinomas.

EXAMPLE 10

LOCALISATION OF $I^{125}$-LABELLED ANTI-CEA ANTIBODIES TO HUMAN COLON ADENOCARCINOMA.

Example 6 describes data on the localisation of technetium-99m labelled CEA6 scFv to tumours in a nude mouse xenografted with human colon adenocarcinoma. These experiments have been repeated using $I^{125}$-labelled CEA6 scFv, along with TO6D11 scFv, in the same animal model.

a. Labelling of monomeric preparations of scFv with $I^{125}$.

Labelling of the scFv's with $I^{125}$ was achieved using the "Iodogen Method" first described by Fraker and Speck (1978) Biochem. Biophysc. Res. Commun 80; 849–857. Iodinated scFv preparations were passed down a CEA column to purify the active CEA-binding fraction of the preparation. Between 70–90% of the labelled protein was retained by a CEA-sepharose column (loaned by Dr David Read, Dept Clinical Oncology Royal Free Hospital, London), demonstrating that the majority of iodinated scFv retained its binding capacity for CEA.

b. Animal model.

Human LS174T xenografts were established in nude mice by subcutaneous passaging from the human colon adenocarcinoma cell line LS 174T. Groups of four mice were taken for each time point. The mice were injected through the tail vein with 100 ml of approximately 10 µg of $I^{125}$-labelled scFv's at a specific activity of 1 mCi/mg. Mice were killed at 3, 24 or 48 hours after injection and the tissue:blood ratios of the antibodies measured by gamma counting.

The results obtained for CEA6, the related clone TO6D11 are shown in Table 6. Iodine adds preferentially to tyrosine residues in the protein and hence addition of the iodine isotope to the four tyrosine residues present in the CDR3 of the VH of CEA6 and T06D11 may have disrupted the binding capabilities of these scFv's for CEA. Since both scFv's retained their abilities to bind CEA both on a CEA column and in the tumour it was evident that the presence of $I^{125}$ did not disrupt the scFv-CEA binding interaction, and hence labelling of the scFv with $I^{125}$ is a viable labelling protocol for any clinical applications of the scFv. CEA6 gave a tumour:blood of 22.5:1 24 hours post-injection of the mice with the labelled scFv, and this value fell to 3.1:1 48 hours post-injection. T06D1 1 did not localise to the tumour as effectively as CEA6, giving a tumour:blood of 5.8:1 24 hours post-injection, but the T06D11 which did target the tumour was retained there longer than the targeted CEA6; at 48 hours post-injection the tumour:blood for T06D11 was 6.6:1.

TABLE 1

Oligonucleotide primers used in the identification and characterisation of CEA antibodies.

FDTSEQ
5' GTCGTCTTTCCAGACGTTAGT-3'

LMB3
5' CAGGAAACAGCTATGAC-3'

MYCSEQ10
5' CTCTTCTGAGATGAGTTTTTG-3'

PCR-L-LINK
5' GGCGGAGGTGGCTCTGGCGGT-3'

PCR-H-LINK
5' ACGGCCAGAGCCACCTCCGCC-3' pUC19REVERSE
5' AGCGGATAACAATTTCACACAGG-3'

CEA6JH
5' TACTACATGGACGTCTGG-3'

CEA6LCNOT
5' GTGATGGTGATGATGATGTGCGGCCGGACGTTTGATCTCCAGCTTGGTCCC-3'

CEA6HCDOP
5' GACGTCCATGTAGTAGTAGTAADNMYYABHABHABNABHABNTCCCGCACAGTAATACACGGC-3'

CEA6LCDOP
5' GATCTCCAGCTTGGTCCCTCCGCCGAAAGTGAGCGGABHABHABHABHTTGTTGGCAGTAATAAGT-3'

B = T,G or C;   H = T,C or A;   M = C or A;   Y = T or C.

TABLE 2

$K_{Off}$ and $K_{On}$ determination of anti-CEA scFvs by surface plasmon resonance.

| Clone | $K_{off}$ (s$^{-1}$) | $K_{on}$ (M$^{-1}$s$^{-1}$) | DISSOCIATION CONSTANT ($K_{off}/K_{On}$) (M) |
|---|---|---|---|
| CEA6 | $6.0 \times 10^{-3}$ | $9.0 \times 10^{5}$ | $7.0 \times 10^{-9}$ |
| TO6D4 | $4.0 \times 10^{-3}$ | $4.0 \times 10^{5}$ | $1.0 \times 10^{-8}$ |
| TO6D8 | $2.3 \times 10^{-3}$ | $4.0 \times 10^{5}$ | $6.0 \times 10^{-9}$ |
| TO6D10 | $1.4 \times 10^{-3}$ | $1.0 \times 10^{6}$ | $1.0 \times 10^{-9}$ |
| TO6D12 | $3.3 \times 10^{-3}$ | $9.0 \times 10^{5}$ | $3.0 \times 10^{-9}$ |
| TO6D11 | $9.0 \times 10^{-4}$ | $1.5 \times 10^{6}$ | $6.0 \times 10^{-10}$ |
| HBB11 | $2.0 \times 10^{-3}$ | $1.5 \times 10^{6}$ | $1.0 \times 10^{-9}$ |
| HBA11 | $5.5 \times 10^{-3}$ | $9.0 \times 10^{5}$ | $6.0 \times 10^{-9}$ |
| HBB6 | $5.7 \times 10^{-3}$ | $9.0 \times 10^{5}$ | $6.0 \times 10^{-9}$ |

TABLE 3

Affinities of anti-CEA scFvs measured by binding inhibition ELISA

| Clone | DISSOCIATION CONSTANT (M) |
|---|---|
| CEA1 | $1.0 \times 10^{-6}$ |
| CEA2 | $5.0 \times 10^{-7}$ |
| CEA3 | $5.0 \times 10^{-7}$ |
| CEA4 | $1.0 \times 10^{-7}$ |
| CEA5 | $1.0 \times 10^{-8}$ |
| CEA6 | $7.0 \times 10^{-9}$ |

TABLE 4

Relative levels of binding and off rates of purified CEA domains passed across TO6D11 or CEA6 scFv's coupled BiaCore surfaces.

| | CEA domains | | | | |
|---|---|---|---|---|---|
| | Desial CEA | A1–B1 | A2–B2 | A3–B3 | N |
| TO6D11 375 RU chip | | | | | |
| RU bound | >1000 | 167 | 112 | 100 | 9 |
| $K_{off}(s^{-1})$ | $9 \times 10^{-3}$ | $7 \times 10^{-2}$ | $7 \times 10^{-2}$ | $4 \times 10^{-2}$ | — |
| CEA6 394 RU chip | | | | | |
| RU bound | >1000 | 115 | 130 | 150 | 30 |
| $K_{off}(s^{-1})$ | $9 \times 10^{-3}$ | $8 \times 10^{-2}$ | $8 \times 10^{-2}$ | $4 \times 10^{-2}$ | — |

Too few RU's of N domain remained on the TO6D11 and CEA6 chips to calculate a $K_{off}$.

TABLE 5

% inhibition of the binding of CEA1, CEA2, CEA3, CEA4, CEA5 and CEA6 to CEA by free K1 and CA PSA.

| | Inhibition of native CEA binding (%) | |
|---|---|---|
| Clone | K1 | CA |
| CEA1 | 53 | 94 |
| CEA2 | 90 | 75 |
| CEA3 | 0 | 29 |
| CEA4 | 25 | 48 |
| CEA5 | 2 | 15 |
| CEA6 | 7 | 0 |

TABLE 6

Average tissue: blood ratios of CEA6, TO6D11 and Colin scFv's in the mouse model of human colon adenocarcinoma.

|  | CEA6 hr pi | | | TO6D11 hr pi | | |
|---|---|---|---|---|---|---|
|  | 3 | 24 | 48 | 3 | 24 | 48 |
| Blood | 1 | 1 | 1 | 1 | 1 | 1 |
| Liver | 0.4 | 0.9 | 0.8 | 0.5 | 0.8 | 0.6 |
| Kidney | 1.3 | 5.5 | 4.1 | 1.8 | 5.9 | 6.7 |
| Lung | 0.6 | 1.1 | 0.7 | 0.7 | 1.1 | 0.7 |
| Spleen | 0.6 | 0.7 | 0.6 | 0.5 | 0.6 | 0.9 |
| Colon | 0.4 | 0.5 | 0.4 | 0.4 | 0.4 | 0.6 |
| Muscle | 0.2 | 0.4 | 0.4 | 0.3 | 0.3 | 0.3 |
| Bone | 0.3 | 0.5 | 0.7 | 0.3 | 0.4 | 0.5 |
| Tumour | 0.9 | 22.5 | 3.1 | 1.0 | 5.8 | 6.6 | hr pi = Hours post-injection

---

We claim:

1. An isolated specific binding member comprising a human antibody antigen binding domain specific for human carcinoembryonic antigen wherein the binding domain has a dissociation constant for human carcinoembryonic antigen which is less than $1.0 \times 10^{-8}$M.

2. A specific binding member according to claim 1 wherein the binding domain has a dissociation constant for human carcinoembryonic antigen which is less than $5.0 \times 10^{-9}$M.

3. A specific binding member according to claim 1 wherein the human antibody antigen binding domain comprises a VH domain and a VL domain, the VH and VL domains being selected from the group consisting of the following pairings:

(i) the VH domain of CEA6, the amino acid sequence of which is shown in FIG. 1(a) (SEQ ID NO: 1), and the VL domain of CEA6, the amino acid sequence for which is shown in FIG. 1(b) (SEQ ID NO: 2);

(ii) the VH domain of CEA6, the amino acid sequence of which is shown in FIG. 1(a) (SEQ ID NO: 1), and a VL domain selected from the group consisting of T06D4, T06D8 and T06D12, the amino acid sequences of which are shown in FIG. 4 (SEQ ID NOS: 3–5, respectively);

(iii) the VL domain of CEA6, the amino acid sequence of which is shown in FIG. 1(b) (SEQ ID NO: 2), and a VH domain selected from the group consisting of T06D10, HBA11, HBB11 and HBB6, the amino acid sequences of which are shown in FIG. 2 (SEQ ID NOS: 6–9, respectively); and (iv) that of T06D11, i.e. the VH domain of T06D10, the amino acid sequence of which is shown in FIG. 2 (SEQ ID NO: 6), and the VL domain of T06D12, the amino acid sequence of which is shown in FIG. 4 (SEQ ID NO: 5).

4. An isolated specific binding member comprising a human antibody antigen binding domain specific for human carcinoembryonic antigen, wherein the binding domain is substantially non-cross-reactive with human liver cells.

5. A specific binding member according to claim 4 wherein the human antibody antigen binding domain comprises a VH domain and a VL domain, the VH and VL domains being selected from the group consisting of the following pairings:

(i) the VH domain of CEA6, the amino acid sequence of which is shown in FIG. 1(a) (SEQ ID NO: 1), and a VL domain selected from the group consisting of T06D4 and T06D12, the amino acid sequences of which are shown in FIG. 4 (SEQ ID NOS: 3 & 5);

(ii) the VL domain of CEA6, the amino acid sequence of which is shown in FIG. 1(b) (SEQ ID NO: 2), and the VH domain of T06D10, the amino acid sequence of which is shown in FIG. 2 (SEQ ID NO: 6); and (iii) that of T06D11, i.e. the VH domain of T06D10, the amino acid sequence of which is shown in FIG. 2 (SEQ ID NO: 6), and the VL domain of T06D12, the amino acid sequence of which is shown in FIG. 4 (SEQ ID NO: 5).

6. A specific binding member according to claim 4 which does not significantly bind one or more of vascular endothelium, muscle, neutrophils, erythrocytes and lymphocytes.

7. An isolated specific binding member comprising a human antibody antigen binding domain which binds to the A3-B3 extracellular domain of human carcinoembryonic antigen.

8. A specific binding member according to claim 7 wherein the human antibody antigen binding domain comprises a VH domain and a VL domain, the VH and VL domains being selected from the group consisting of the following pairings:

(i) the VH domain of CEA6, the amino acid sequence of which is shown in FIG. 1(a) (SEQ ID NO: 1), and the VL domain of CEA6, the amino acid sequence for which is shown in FIG. 1(b) (SEQ ID NO: 2);

(ii) the VH domain of CEA6, the amino acid sequence of which is shown in FIG. 1(a) (SEQ ID NO: 1), and a VL domain selected from the group consisting of T06D4, T06D8 and T06D12, the amino acid sequences of which are shown in FIG. 4 (SEQ ID NOS: 3–5, respectively);

(iii) the VL domain of CEA6, the amino acid sequence of which is shown in FIG. 1(b) (SEQ ID NO: 2), and a VH domain selected from the group consisting of HBA11, HBB11 and HBB6, the amino acid sequences of which are shown in FIG. 2 (SEQ ID NOS: 7–9, respectively);

(iv) that of T06D11, i.e. the VH domain of T06D10, the amino acid sequence of which is shown in FIG. 2 (SEQ ID NO: 6), and the VL domain of T06D12, the amino acid sequence of which is shown in FIG. 4 (SEQ ID NO: 5); and (v) the VH domain of CEA6, the amino acid sequence of which is shown in FIG. 1(a) (SEQ ID NO: 1), and a VL domain selected from the group consisting of LOB1C (SEQ ID NO: 17), LOE17 (SEQ ID NO: 18) and LOSC2 (SEQ ID NO: 19), the amino acid sequences of which are shown in FIG. 3.

9. An isolated specific binding member comprising a human antibody antigen binding domain specific for human carcinoembryonic antigen, wherein the binding domain binds to cell-associated human carcinoembryonic antigen preferentially over soluble human carcinoembryonic antigen.

10. A specific binding member according to claim 9 wherein the human antibody antigen binding domain comprises a VH domain and a VL domain, the VH and VL domains being selected from the group consisting of the following pairings:

(i) the VH domain of CEA6, the amino acid sequence of which is shown in FIG. 1(a) (SEQ ID NO: 1), and the VL domain of CEA6, the amino acid sequence for which is shown in FIG. 1(b) (SEQ ID NO: 2);

(ii) the VH domain of CEA6, the amino acid sequence of which is shown in FIG. 1(a) (SEQ ID NO: 1), and a VL domain selected from the group consisting of T06D4 and T06D12, the amino acid sequences of which are shown in FIG. 4 (SEQ ID NOS: 3 & 5);

(iii) the VL domain of CEA6, the amino acid sequence of which is shown in FIG. 1(b) (SEQ ID NO: 2), and a VH domain selected from the group consisting of TO6D10 and HBB11, the amino acid sequences of which are shown in FIG. 2 (SEQ ID NOS: 6 & 8); and (iv) that of TO6D11, i.e. the VH domain of TO6D10, the amino acid sequence of which is shown in FIG. 2 (SEQ ID NO: 6), and the VL domain of TO6D12, the amino acid sequence of which is shown in FIG. 4 (SEQ ID NO: 5).

11. An isolated specific binding member comprising a human antibody antigen binding domain specific for human carcinoembryonic antigen, wherein the binding domain is specific for a carbohydrate epitope of human carcinoembryonic antigen.

12. A specific binding member according to claim 11 wherein the human antibody antigen binding domain is selected from the group consisting of the antibody antigen binding domains of CEA1, CEA2, CEA3, CEA4 and CEA5, the amino acid sequences of the VH domains of which are shown in FIG. 1(a) (SEQ ID NOS: 10–14, respectively) and the amino acid sequences of the VL domains of which are shown in FIG. 1(b) (SEQ ID NOS: 15(CEA1, CEA2, & CEA3) 16 (CEA4 & CEA5), and 2 (CEA6 & CEA7)).

13. An isolated specific binding member comprising a human antibody antigen binding domain specific for human carcinoembryonic antigen.

14. A specific binding member according to claim 13 wherein said human antibody antigen binding domain comprises a VH1, VH3 or VH4 region encoded by a gene sequence selected from the group consisting of the following germ lines: the DP71 germ line; the DP47 germ line; the DP67 germ line; the DP32 germ line; the DP10 germ line and the DP14 germ line; and a re-arranged form thereof.

15. A specific binding member according to claim 13 wherein said human antibody antigen binding domain comprises a V11, V13 or Vk1 region encoded by a gene sequence selected from the group consisting of the following germ lines: the germ line DPL5; the DPL2 germ line; the germ line DPL16; the germ line L12a; and a re-arranged form thereof.

16. A specific binding member according to claim 13 wherein said human antibody antigen binding domain comprises a VH domain having any of the amino acid sequences shown in FIG. 1 (a) (SEQ ID NOS: 1, 10–14, & 19).

17. A specific binding member according to claim 13 wherein said human antibody antigen binding domain comprises one or more complementarity determining region (CDR) with an amino acid sequence identified in FIG. 1 (a) (SEQ ID NOS: 1, 10–14, & 19)as a CDR1, CDR2 or CDR3 sequence.

18. A specific binding member according to claim 17 wherein said human antibody antigen binding domain comprises a CDR3 sequence shown in FIG. 1(a) (SEQ ID NOS: 1, 10–14, & 19).

19. A specific binding member according to claim 13 wherein said human antibody antigen binding domain comprises a VH domain having any of the amino acid sequences shown in FIG. 2 (SEQ ID NOS: 6–9) as a variant of CEA6.

20. A specific binding member according to claim 13 wherein said human antibody antigen binding domain comprises a CDR3 sequence shown in FIG. 2 (SEQ ID NO: 6–9) as a variant of CDR3 of CEA6.

21. A specific binding member according to claim 13 wherein said human antibody antigen binding domain comprises a VL domain having any of the amino acid sequences shown in FIG. 1 (b) (SEQ ID NO: 2, 15 & 16).

22. A specific binding member according to claim 13 wherein said human antibody antigen binding domain comprises one or more complementarity determining region (CDR) with an amino acid sequence identified in FIG. 1 (b) (SEQ ID NOS: 2, 15 & 16) as a CDR1, CDR2 or CDR3 sequence.

23. A specific binding member according to claim 13 wherein said human antibody antigen binding domain comprises a VL domain having any of the amino acid sequences shown in FIG. 3 (SEQ ID NOS: 17 & 18 ) as a variant of CEA6.

24. A specific binding member according to claim 13 wherein said human antibody antigen binding domain comprises a CDR3 sequence shown in FIG. 3 (SEQ ID NOS: 17 & 18) as a variant of CDR3 of CEA6.

25. A specific binding member according to claim 13 wherein said human antibody antigen binding domain comprises a VL domain having any of the amino acid sequences shown in FIG. 4 (SEQ ID NOS: 3–5) as a variant of CEA6.

26. A specific binding member according to claim 13 wherein said human antibody antigen binding domain comprises one or more complementarity determining region (CDR) with an amino acid sequence identified in FIG. 4 (SEQ ID NOS: 3–5 and 53) as a CDR1, CDR2 or CDR3 sequence variant of a CEA6 CDR.

27. A specific binding member according to claim 13 which is a single chain Fv (scFv) molecule.

28. A specific binding member according to claim 13 which comprises one or more amino acids in addition to those forming said human antibody antigen binding domain.

29. A specific binding member according to claim 13 which comprises a label or reporter molecule.

30. A specific binding member according to claim 29 wherein the label is radioactive iodine.

31. An isolated specific binding member comprising a human antibody antigen binding domain which competes with a specific binding member that comprises an antigen binding domain comprising the VH domain of TO06D10, the amino acid sequence of which is shown in FIG. 2 (SEQ ID NO: 6), and the VL domain of T06D12, the amino acid sequence of which is shown in FIG. 4(SEQ ID NO: 5), for binding to human carcinoembryonic antigen.

32. An islated specific binding member comprising a human antibody antigen binding domain which competes with a specific binding member that comprises an antigen binding domain comprising the VH domain of CEA1, the amino acid sequence of which is shown in FIG. 1(a) (SEQ ID NO: 16) and the VL domain of CEA1, the amino acid sequence of which is shown in FIG. 1(b) (SEQ ID NO: 15), for binding to human carcinoembryonic antigen.

\* \* \* \* \*

SEQUENCE LISTING ( 1 ) GENERAL INFORMATION:

( i i i ) NUMBER OF SEQUENCES: 53

( 2 ) INFORMATION FOR SEQ ID NO:1:

( i ) SEQUENCE CHARACTERISTICS:
        ( A ) LENGTH: 123 amino acids
        ( B ) TYPE: amino acid
        ( D ) TOPOLOGY: linear ( x i ) SEQUENCE DESCRIPTION: SEQ ID NO:1:

```
Gln  Val  Gln  Leu  Val  Gln  Ser  Gly  Ala  Glu  Val  Lys  Lys  Pro  Gly  Ser
 1                   5                        10                       15

Ser  Val  Lys  Val  Ser  Cys  Lys  Ala  Ser  Gly  Gly  Thr  Phe  Ser  Asn  Ser
               20                       25                       30

Pro  Ile  Asn  Trp  Leu  Arg  Gln  Ala  Pro  Gly  Gln  Gly  Leu  Glu  Trp  Met
          35                            40                       45

Gly  Ser  Ile  Ile  Pro  Ser  Phe  Gly  Thr  Ala  Asn  Tyr  Ala  Gln  Lys  Phe
     50                       55                       60

Gln  Gly  Arg  Leu  Thr  Ile  Thr  Ala  Asp  Glu  Ser  Thr  Ser  Thr  Ala  Tyr
65                       70                       75                       80

Met  Glu  Leu  Ser  Ser  Leu  Arg  Ser  Glu  Asp  Thr  Ala  Val  Tyr  Tyr  Cys
                    85                       90                       95

Ala  Gly  Arg  Ser  His  Asn  Tyr  Glu  Leu  Tyr  Tyr  Tyr  Tyr  Met  Asp  Val
               100                      105                      110

Trp  Gly  Gln  Gly  Thr  Met  Val  Thr  Val  Ser  Ser
               115                      120
```

( 2 ) INFORMATION FOR SEQ ID NO:2:

( i ) SEQUENCE CHARACTERISTICS:
        ( A ) LENGTH: 108 amino acids
        ( B ) TYPE: amino acid
        ( D ) TOPOLOGY: linear ( x i ) SEQUENCE DESCRIPTION: SEQ ID NO:2:

```
Asp  Ile  Gln  Met  Thr  Gln  Ser  Pro  Ser  Ser  Leu  Ser  Ala  Ser  Ile  Gly
```

|   |   | 1 |   |   |   | 5 |   |   |   |   | 10 |   |   |   |   | 15 |
|---|---|---|---|---|---|---|---|---|---|---|---|---|---|---|---|---|

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Ser Gly Thr Asp Phe Thr Leu Thr Ile Ser Ser Leu Gln Pro
65                      70                  75                      80

Asp Asp Phe Ala Thr Tyr Tyr Cys Gln Gln Tyr Ser Asn Tyr Pro Leu
                85                  90                  95

Thr Phe Gly Gly Gly Thr Lys Leu Glu Ile Lys Arg
            100                 105

(2) INFORMATION FOR SEQ ID NO:3:

(i) SEQUENCE CHARACTERISTICS:
        (A) LENGTH: 108 amino acids
        (B) TYPE: amino acid
        (D) TOPOLOGY: linear (xi) SEQUENCE DESCRIPTION: SEQ ID NO:3:

Asp Ile Val Met Thr Gln Ser Pro Ser Thr Leu Ser Ala Ser Val Gly
1                       5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Val Gly Val Pro Ser Arg Phe Ser Gly
    50                  55                  60

Ser Gly Ser Gly Thr Asp Phe Thr Leu Thr Ile Ser Ser Leu Gln Pro
65                      70                  75                      80

Glu Asp Phe Ala Thr Tyr Tyr Cys Gln Gln Ser Tyr Ser Thr Pro Trp
                85                  90                  95

Thr Phe Gly Gln Gly Thr Lys Leu Glu Ile Lys Arg
            100                 105

(2) INFORMATION FOR SEQ ID NO:4:

(i) SEQUENCE CHARACTERISTICS:
        (A) LENGTH: 108 amino acids
        (B) TYPE: amino acid
        (D) TOPOLOGY: linear (xi) SEQUENCE DESCRIPTION: SEQ ID NO:4:

Asp Ile Val Met Thr Gln Ser Pro Ser Thr Leu Ser Ala Ser Val Gly
1                       5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                      70                  75                      80

Glu Asp Phe Ala Thr Tyr Tyr Cys Gln Gln Ser Tyr Ser Thr Pro Trp
                85                  90                  95

Thr Phe Gly Gln Gly Thr Lys Leu Glu Ile Lys Arg ( 2 ) INFORMATION FOR SEQ ID NO:5:

( i ) SEQUENCE CHARACTERISTICS:
        ( A ) LENGTH: 108 amino acids
        ( B ) TYPE: amino acid
        ( D ) TOPOLOGY: linear ( x i ) SEQUENCE DESCRIPTION: SEQ ID NO:5:

```
Asp Ile Val Met Thr Gln Ser Pro Ser Thr Leu Ser Ala Ser Val Gly
 1               5                  10                  15
Asp Arg Val Thr Ile Thr Cys Arg Ala Ser Gln Gly Ile Ser Ser Trp
                20                  25                  30
Leu Ala Trp Tyr Gln Gln Lys Pro Gly Lys Ala Pro Lys Leu Leu Ile
             35                  40                  45
Tyr Lys Ala Ser Ser Leu Ala Ser Gly Ala Pro Ser Arg Phe Ser Gly
     50                  55                  60
Ser Gly Ser Gly Thr Asp Phe Thr Leu Thr Ile Ser Ser Leu Gln Pro
65                  70                  75                  80
Asp Asp Phe Ala Thr Tyr Tyr Cys Gln Gln Tyr Ser Asn Tyr Pro Leu
                 85                  90                  95
Thr Phe Gly Gly Gly Thr Lys Leu Glu Ile Lys Arg
                100                 105
```

( 2 ) INFORMATION FOR SEQ ID NO:6:

( i ) SEQUENCE CHARACTERISTICS:
        ( A ) LENGTH: 123 amino acids
        ( B ) TYPE: amino acid
        ( D ) TOPOLOGY: linear ( x i ) SEQUENCE DESCRIPTION: SEQ ID NO:6:

```
Gln Val Gln Leu Val Gln Ser Gly Ala Glu Val Lys Lys Pro Gly Ser
 1               5                  10                  15
Ser Val Lys Val Ser Cys Lys Ala Ser Gly Gly Thr Phe Ser Asn Ser
                20                  25                  30
Pro Ile Asn Trp Leu Arg Gln Ala Pro Gly Gln Gly Leu Glu Trp Met
             35                  40                  45
Gly Ser Ile Ile Pro Ser Phe Gly Thr Ala Asn Tyr Ala Gln Lys Phe
     50                  55                  60
Gln Gly Arg Leu Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                 85                  90                  95
Ala Gly Cys Ser His Asn Tyr Glu Leu Tyr Tyr Tyr Tyr Met Asp Val
                100                 105                 110
Trp Gly Gln Gly Thr Met Val Thr Val Ser Ser
            115                 120
```

( 2 ) INFORMATION FOR SEQ ID NO:7:

( i ) SEQUENCE CHARACTERISTICS:
        ( A ) LENGTH: 123 amino acids
        ( B ) TYPE: amino acid
        ( D ) TOPOLOGY: linear ( x i ) SEQUENCE DESCRIPTION: SEQ ID NO:7:

```
Gln Val Gln Leu Val Gln Ser Gly Ala Glu Val Lys Lys Pro Gly Ser
 1               5                  10                  15
```

```
Ser  Val  Lys  Val  Ser  Cys  Lys  Ala  Ser  Gly  Gly  Thr  Phe  Ser  Asn  Ser
               20                       25                          30

Pro  Ile  Asn  Trp  Leu  Arg  Gln  Ala  Pro  Gly  Gln  Gly  Leu  Glu  Trp  Met
               35                       40                          45

Gly  Ser  Ile  Ile  Pro  Ser  Phe  Gly  Thr  Ala  Asn  Tyr  Ala  Gln  Lys  Phe
     50                        55                       60

Gln  Gly  Arg  Leu  Thr  Ile  Thr  Ala  Asp  Glu  Ser  Thr  Ser  Thr  Ala  Tyr
65                        70                      75                          80

Met  Glu  Leu  Ser  Ser  Leu  Arg  Ser  Glu  Asp  Thr  Ala  Val  Tyr  Tyr  Cys
               85                       90                          95

Ala  Gly  Ala  Asn  Ser  Cys  Asn  Arg  Ser  Tyr  Tyr  Tyr  Tyr  Met  Asp  Val
               100                      105                         110

Arg  Gly  Gln  Gly  Thr  Met  Val  Thr  Val  Ser  Ser
               115                      120
```

( 2 ) INFORMATION FOR SEQ ID NO:8:

( i ) SEQUENCE CHARACTERISTICS:
    ( A ) LENGTH: 123 amino acids
    ( B ) TYPE: amino acid
    ( D ) TOPOLOGY: linear ( x i ) SEQUENCE DESCRIPTION: SEQ ID NO:8:

```
Gln  Val  Gln  Leu  Val  Gln  Ser  Gly  Ala  Glu  Val  Lys  Lys  Pro  Gly  Ser
1                    5                       10                          15

Ser  Val  Lys  Val  Ser  Cys  Lys  Ala  Ser  Gly  Gly  Thr  Phe  Ser  Asn  Ser
               20                       25                          30

Pro  Ile  Asn  Trp  Leu  Arg  Gln  Ala  Pro  Gly  Gln  Gly  Leu  Glu  Trp  Met
               35                       40                          45

Gly  Ser  Ile  Ile  Pro  Ser  Phe  Gly  Thr  Ala  Asn  Tyr  Ala  Gln  Lys  Phe
     50                        55                       60

Gln  Gly  Arg  Leu  Thr  Ile  Thr  Ala  Asp  Glu  Ser  Thr  Ser  Thr  Ala  Tyr
65                        70                      75                          80

Met  Glu  Leu  Ser  Ser  Leu  Arg  Ser  Glu  Asp  Thr  Ala  Val  Tyr  Tyr  Cys
               85                       90                          95

Ala  Arg  His  Asn  His  Asn  Tyr  Glu  Leu  Tyr  Tyr  Tyr  Tyr  Met  Asp  Val
               100                      105                         110

Trp  Gly  Gln  Gly  Thr  Met  Val  Thr  Val  Ser  Ser
               115                      120
```

( 2 ) INFORMATION FOR SEQ ID NO:9:

( i ) SEQUENCE CHARACTERISTICS:
    ( A ) LENGTH: 123 amino acids
    ( B ) TYPE: amino acid
    ( D ) TOPOLOGY: linear ( x i ) SEQUENCE DESCRIPTION: SEQ ID NO:9:

```
Gln  Val  Gln  Leu  Val  Gln  Ser  Gly  Ala  Glu  Val  Lys  Lys  Pro  Gly  Ser
1                    5                       10                          15

Ser  Val  Lys  Val  Ser  Cys  Lys  Ala  Ser  Gly  Gly  Thr  Phe  Ser  Asn  Ser
               20                       25                          30

Pro  Ile  Asn  Trp  Leu  Arg  Gln  Ala  Pro  Gly  Gln  Gly  Leu  Glu  Trp  Met
               35                       40                          45

Gly  Ser  Ile  Ile  Pro  Ser  Phe  Gly  Thr  Ala  Asn  Tyr  Ala  Gln  Lys  Phe
     50                        55                       60

Gln  Gly  Arg  Leu  Thr  Ile  Thr  Ala  Asp  Glu  Ser  Thr  Ser  Thr  Ala  Tyr
65                        70                      75                          80
```

Met Glu Leu Ser Ser Leu Arg Ser Glu Asp Thr Ala Val Tyr Tyr Cys
                    85                  90                  95

Ala Gly Arg Ser His Thr Tyr Glu Leu Tyr Tyr Tyr Tyr Met Asp Val
            100             105             110

Trp Gly Gln Gly Thr Met Val Thr Val Ser Ser
            115             120

(2) INFORMATION FOR SEQ ID NO:10:

(i) SEQUENCE CHARACTERISTICS:
        (A) LENGTH: 119 amino acids
        (B) TYPE: amino acid
        (D) TOPOLOGY: linear (xi) SEQUENCE DESCRIPTION: SEQ ID NO:10:

Gln Val Gln Leu Gln Gln Ser Gly Pro Gly Leu Val Lys Pro Ser Glu
1               5               10              15

Thr Leu Ser Leu Thr Cys Thr Val Ser Gly Asp Ser Ile Ser Ser Tyr
            20              25              30

Tyr Trp Ser Trp Ile Arg Gln Pro Pro Gly Lys Gly Leu Glu Trp Ile
            35              40              45

Gly Tyr Ile His Tyr Ser Gly Ser Thr Asn Ser Asn Pro Ser Leu Lys
    50              55              60

Ser Arg Val Thr Ile Ser Gly Asp Thr Ser Lys Lys Arg Phe Ser Leu
65              70              75              80

Lys Leu Ser Ser Val Thr Ala Ala Asp Thr Ala Val Tyr Tyr Cys Ala
                85              90              95

Ala Ser Gly Ala Tyr Asp Asn Tyr Gly Ile Asp Val Trp Gly Lys Gly
            100             105             110

Thr Leu Val Thr Val Ser Ser
            115

(2) INFORMATION FOR SEQ ID NO: 11:

(i) SEQUENCE CHARACTERISTICS:
        (A) LENGTH: 118 amino acids
        (B) TYPE: amino acid
        (D) TOPOLOGY: linear (xi) SEQUENCE DESCRIPTION: SEQ ID NO: 11:

Gln Val Gln Leu Val Gln Ser Gly Gly Gly Leu Val Gln Pro Gly Gly
1               5               10              15

Ser Leu Arg Leu Ser Cys Ala Ala Ser Gly Phe Ser Val Ser Ser Asn
            20              25              30

Tyr Met Ser Trp Val Arg Gln Ser Pro Gly Lys Gly Leu Glu Tyr Val
            35              40              45

Ser Ala Ile Ser Ser Asn Gly Gly Ser Thr Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Ser Ser Pro Arg Ala Glu Asp Thr Ala Val Tyr Tyr Cys
                85              90              95

Ala Arg Phe Ile Asn Pro Tyr Gly Met Asp Val Trp Gly Gln Gly Thr
            100             105             110

Leu Val Thr Val Ser Ser
            115

(2) INFORMATION FOR SEQ ID NO: 12:

(i) SEQUENCE CHARACTERISTICS:
    (A) LENGTH: 118 amino acids
    (B) TYPE: amino acid
    (D) TOPOLOGY: linear (xi) SEQUENCE DESCRIPTION: SEQ ID NO: 12:

```
Glu Val His Leu Val Glu Ser Gly Arg Ala Leu Val Gln Pro Gly Gly
 1               5                  10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ala Leu Val Arg Gly Val Ile Lys Asp Trp Gly Gln Gly Thr
            100                 105                 110
Leu Val Thr Val Ser Ser
            115
```

(2) INFORMATION FOR SEQ ID NO:13:

(i) SEQUENCE CHARACTERISTICS:
        (A) LENGTH: 118 amino acids
        (B) TYPE: amino acid
        (D) TOPOLOGY: linear (xi) SEQUENCE DESCRIPTION: SEQ ID NO:13:

```
Gln Val Gln Leu Gln Gln Ser Gly Pro Gly Arg Val Lys Pro Ser Glu
 1               5                  10                  15
Thr Leu Ser Leu Thr Cys Thr Val Ser Gly Tyr Ser Val Ser Val Ser
            20                  25                  30
Tyr Tyr Trp Gly Trp Ile Arg Gln Ser Pro Gly Thr Gly Leu Glu Trp
        35                  40                  45
Ile Gly Ser Ile Ser His Ser Gly Ser Thr Tyr Tyr Asn Pro Ser Leu
    50                  55                  60
Lys Ser Arg Val Thr Ile Ser Gly Asp Ala Ser Lys Asn Gln Phe Phe
65                  70                  75                  80
Leu Arg Leu Thr Ser Val Thr Ala Ala Asp Thr Ala Val Tyr Tyr Cys
                85                  90                  95
Ala Arg Ser Glu Pro Thr Ala Asn Phe Asp Ser Trp Gly Arg Gly Thr
            100                 105                 110
Leu Val Thr Val Ser Ser
            115
```

(2) INFORMATION FOR SEQ ID NO:14:

(i) SEQUENCE CHARACTERISTICS:
        (A) LENGTH: 116 amino acids
        (B) TYPE: amino acid
        (D) TOPOLOGY: linear (xi) SEQUENCE DESCRIPTION: SEQ ID NO:14:

```
Glu Val Gln Leu Val Glu Ser Gly Gly Gly Val Val Arg Pro Gly Gly
 1               5                  10                  15
Ser Leu Arg Leu Ser Cys Ala Ala Ser Gly Phe Thr Phe Asp Asp Tyr
            20                  25                  30
```

Gly Met Ser Trp Val Arg Gln Ala Pro Gly Lys Gly Leu Glu Trp Val
          35                    40                      45

Ser Gly Ile Asn Trp Asn Gly Gly Ser Thr Gly Tyr Ala Asp Ser Val
    50                      55                  60

Lys Gly Arg Phe Thr Ile Ser Arg Asp Asn Ala Lys Asn Ser Leu Tyr
65                      70                  75                  80

Leu Gln Met Asn Ser Leu Arg Ala Glu Asp Thr Ala Val Tyr Tyr Cys
                85                      90                  95

Ala Arg Arg Arg Tyr Ala Leu Asp Tyr Trp Gly Gln Gly Thr Leu Val
            100                 105                 110

Thr Val Ser Arg
            115

( 2 ) INFORMATION FOR SEQ ID NO:15:

( i ) SEQUENCE CHARACTERISTICS:
        ( A ) LENGTH: 111 amino acids
        ( B ) TYPE: amino acid
        ( D ) TOPOLOGY: linear ( x i ) SEQUENCE DESCRIPTION: SEQ ID NO:15:

Gln Ser Val Leu Thr Gln Pro Pro Ser Val Ala Pro Pro Gly Gln
1               5                   10                  15

Lys Val Thr Ile Ser Cys Ser Gly Ser Thr Pro Asn Ile Gly Asn Asn
            20                  25                  30

Tyr Val Ser Trp Tyr Gln Gln His Pro Gly Lys Ala Pro Lys Leu Met
            35                  40                  45

Ile Tyr Asp Val Ser Lys Arg Pro Ser Gly Val Pro Asp Arg Phe Ser
        50                  55                  60

Gly Ser Lys Ser Gly Asn Ser Ala Ser Leu Asp Ile Ser Gly Leu Gln
65                  70                  75                  80

Ser Glu Asp Glu Ala Asp Tyr Tyr Cys Ala Ala Trp Asp Asp Ser Leu
                85                  90                  95

Ser Glu Phe Leu Phe Gly Thr Gly Thr Lys Leu Glu Ile Lys Arg
            100                 105                 110

( 2 ) INFORMATION FOR SEQ ID NO:16:

( i ) SEQUENCE CHARACTERISTICS:
        ( A ) LENGTH: 109 amino acids
        ( B ) TYPE: amino acid
        ( D ) TOPOLOGY: linear ( x i ) SEQUENCE DESCRIPTION: SEQ ID NO:16:

Ser Ser Glu Leu Thr Gln Asp Pro Ala Val Ser Val Pro Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Pro Pro Val Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Glu Ile Lys Arg
            100                 105

( 2 ) INFORMATION FOR SEQ ID NO:17:

( i ) SEQUENCE CHARACTERISTICS:
        ( A ) LENGTH: 108 amino acids
        ( B ) TYPE: amino acid
        ( D ) TOPOLOGY: linear ( x i ) SEQUENCE DESCRIPTION: SEQ ID NO:17:

```
Asp Ile Gln Met Thr Gln Ser Pro Ser Thr Leu Ser Ala Ser Ile Gly
 1               5                  10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
            35                  40                  45

Tyr Lys Ala Ser Ser Leu Ala Ser Gly Ala Pro Ser Arg Phe Ser Gly
        50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Ser Tyr Ser Thr Pro Leu
                85                  90                  95

Thr Phe Gly Gly Gly Thr Lys Leu Glu Ile Lys Arg
                100                 105
```

( 2 ) INFORMATION FOR SEQ ID NO:18:

( i ) SEQUENCE CHARACTERISTICS:
        ( A ) LENGTH: 108 amino acids
        ( B ) TYPE: amino acid
        ( D ) TOPOLOGY: linear ( x i ) SEQUENCE DESCRIPTION: SEQ ID NO:18:

```
Asp Ile Gln Met Thr Gln Ser Pro Ser Thr Leu Ser Ala Ser Ile Gly
 1               5                  10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
            35                  40                  45

Tyr Lys Ala Ser Ser Leu Ala Ser Gly Ala Pro Ser Arg Phe Ser Gly
        50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Asp Asn Gly Pro Leu
                85                  90                  95

Thr Phe Gly Gly Gly Thr Lys Leu Glu Ile Lys Arg
                100                 105
```

( 2 ) INFORMATION FOR SEQ ID NO:19:

( i ) SEQUENCE CHARACTERISTICS:
        ( A ) LENGTH: 120 amino acids
        ( B ) TYPE: amino acid
        ( D ) TOPOLOGY: linear ( x i ) SEQUENCE DESCRIPTION: SEQ ID NO:19:

```
Gln Val Thr Leu Gln Gln Ser Gly Ala Glu Val Lys Lys Pro Gly Pro
 1               5                  10                  15

Ser Val Lys Val Ser Cys Lys Ala Ser Gly Tyr Thr Phe Thr Ala Tyr
            20                  25                  30

Gly Phe Asn Trp Val Arg Gln Ala Pro Gly Gln Gly Leu Glu Trp Met
```

|  |  | 35 |  |  |  | 40 |  |  |  | 45 |  |  |
|---|---|---|---|---|---|---|---|---|---|---|---|---|
| Trp | Ile 50 | Ser | Ala | Tyr | Ser | Gly 55 | Asn | Thr | Lys | Tyr | Ala 60 | Gln | Lys | Phe | Gln |
| Gly 65 | Arg | Val | Thr | Met | Thr 70 | Thr | Asp | Thr | Ser | Thr 75 | Ser | Thr | Ala | Tyr | Met 80 |
| Glu | Leu | Arg | Ser | Leu 85 | Arg | Ser | Glu | Asp | Thr 90 | Ala | Val | Tyr | Tyr | Cys 95 | Ala |
| Gly | Arg | Arg | Gly 100 | Gly | Phe | Arg | Phe | Arg 105 | Pro | Met | Asp | Val | Trp 110 | Gly | Gln |
| Gly | Thr | Met 115 | Val | Thr | Val | Ser | Ser 120 | | | | | | | | |

( 2 ) INFORMATION FOR SEQ ID NO:20:

( i ) SEQUENCE CHARACTERISTICS:
  ( A ) LENGTH: 357 base pairs
  ( B ) TYPE: nucleic acid
  ( C ) STRANDEDNESS: double
  ( D ) TOPOLOGY: linear ( x i ) SEQUENCE DESCRIPTION: SEQ ID NO:20:

| CAGGTACAGC | TGCAGCAGTC | AGGCCCAGGA | CTGGTGAAGC | CTTCGGAGAC | CCTGTCCCTC | 60 |
|---|---|---|---|---|---|---|
| ACCTGCACTG | TCTCTGGTGA | CTCCATCAGT | AGTTACTACT | GGAGCTGGAT | CCGGCAACCC | 120 |
| CCAGGGAAGG | GACTGGAGTG | GATTGGGTAT | ATCCATTACA | GTGGGAGCAC | CAACTCCAAC | 180 |
| CCCTCCCTCA | AGAGTCGAGT | CACCATATCA | GGAGACACGT | CCAAGAAGCG | GTTCTCCCTG | 240 |
| AAGCTGAGCT | CTGTGACCGC | CGCGGACACG | GCCGTGTATT | ACTGTGCGGC | GTCGGGTGCC | 300 |
| TACGATAATT | ACGGTATAGA | CGTCTGGGGC | AAAGGCACCC | TGGTCACCGT | CTCGAGT | 357 |

( 2 ) INFORMATION FOR SEQ ID NO:21:

( i ) SEQUENCE CHARACTERISTICS:
  ( A ) LENGTH: 354 base pairs
  ( B ) TYPE: nucleic acid
  ( C ) STRANDEDNESS: double
  ( D ) TOPOLOGY: linear ( x i ) SEQUENCE DESCRIPTION: SEQ ID NO:21:

| CAGGTTCAGC | TGGTGCAGTC | TGGGGGAGGC | TTGGTCCAGC | CTGGGGGGTC | CCTGAGACTC | 60 |
|---|---|---|---|---|---|---|
| TCCTGTGCAG | CCTCTGGATT | CAGCGTCAGT | AGCAATTACA | TGAGCTGGGT | CCGCCAGTCT | 120 |
| CCAGGGAAGG | GACTGGAATA | TGTTTCAGCT | ATTAGTAGTA | ATGGGGTAG | CACATACTAC | 180 |
| GCAGACTCCG | TGAAGGGCAG | ATTCACCATC | TCCAGAGACA | ATTCCAAGAA | CACGCTGTAT | 240 |
| CTTCAAATGA | GCAGTCCGAG | AGCTGAGGAC | ACGGCTGTGT | ATTACTGTGC | GAGATTTATA | 300 |
| AATCCCTACG | GTATGGACGT | CTGGGGCCAG | GGCACCCTGG | TCACCGTCTC | CTCA | 354 |

( 2 ) INFORMATION FOR SEQ ID NO:22:

( i ) SEQUENCE CHARACTERISTICS:
  ( A ) LENGTH: 354 base pairs
  ( B ) TYPE: nucleic acid
  ( C ) STRANDEDNESS: double
  ( D ) TOPOLOGY: linear ( x i ) SEQUENCE DESCRIPTION: SEQ ID NO:22:

| GAGGTACACC | TGGTGGAGTC | TGGGAGAGCC | TTGGTACAGC | CTGGGGGGTC | CCTGAGACTC | 60 |
|---|---|---|---|---|---|---|
| TCCTGTGCAG | CCTCTGGATT | CACCTTTAGC | AGCTATGCCA | TGAGCTGGGT | CCGCCAGGCT | 120 |
| CCAGGGAAGG | GGCTGGAGTG | GGTCTCAGCT | ATTAGTGGTA | GTGGTGGTAG | CACATACTAC | 180 |

| GCAGACTCCG | TGAAGGGCCG | GTTCACCATC | TCCAGAGACA | ATTCCAAGAA | CACGCTGTAT | 240 |
| GCAGACTCCG | TGAAGGGCCG | GTTCACCATC | TCCAGAGACA | ATTCCAAGAA | CACGCTGTAT | 240 |

CTGCAAATGA ACAGCCTGAG AGCCGAGGAC ACGGCTGTGT ATTACTGTGC GAGAGCTTTG 300

GTTCGGGGAG TTATAAAGGA CTGGGGCCAG GGAACCCTGG TCACCGTCTC CTCA 354

( 2 ) INFORMATION FOR SEQ ID NO:23:

( i ) SEQUENCE CHARACTERISTICS:
          ( A ) LENGTH: 354 base pairs
          ( B ) TYPE: nucleic acid
          ( C ) STRANDEDNESS: double
          ( D ) TOPOLOGY: linear ( x i ) SEQUENCE DESCRIPTION: SEQ ID NO:23:

CAGGTACAGC TGCAGCAGTC AGGCCCAGGA CGGGTGAAGC CTTCGGAGAC GCTGTCCCTC 60

ACCTGCACTG TCTCTGGTTA CTCCGTCAGT GTGAGTTACT ACTGGGGCTG GATCCGGCAG 120

TCCCCAGGGA CGGGGCTGGA GTGGATTGGG AGTATCTCTC ATAGTGGGAG CACCTACTAC 180

AACCCGTCCC TCAAGAGTCG AGTCACCATA TCAGGAGACG CATCCAAGAA CCAGTTTTTC 240

CTGAGGCTGA CTTCTGTGAC CGCCGCGGAC ACGGCCGTTT ATTACTGTGC GAGATCTGAG 300

CCTACCGCCA ACTTTGATTC TTGGGGCAGG GGCACCCTGG TCACCGTCTC GAGT 354

( 2 ) INFORMATION FOR SEQ ID NO:24:

( i ) SEQUENCE CHARACTERISTICS:
          ( A ) LENGTH: 348 base pairs
          ( B ) TYPE: nucleic acid
          ( C ) STRANDEDNESS: double
          ( D ) TOPOLOGY: linear ( x i ) SEQUENCE DESCRIPTION: SEQ ID NO:24:

GAGGTGCAGC TGGTGGAGTC TGGGGGAGGT GTGGTACGGC CTGGGGGGTC CCTGAGGCTC 60

TCCTGTGCAG CCTCTGGATT CACCTTTGAT GATTATGGCA TGAGCTGGGT CCGCCAAGCT 120

CCAGGGAAGG GGCTGGAGTG GGTCTCTGGT ATTAATTGGA ATGGTGGTAG CACAGGTTAT 180

GCAGACTCTG TGAAGGGCCG ATTCACCATC TCCAGAGACA ACGCCAAGAA CTCCCTGTAT 240

CTTCAAATGA ACAGTCTGAG AGCCGAGGAC ACAGCCGTGT ATTACTGTGC AAGAAGGCGG 300

TATGCGTTGG ATTATTGGGG CCAAGGTACC CTGGTCACCG TGTCGAGA 348

( 2 ) INFORMATION FOR SEQ ID NO:25:

( i ) SEQUENCE CHARACTERISTICS:
          ( A ) LENGTH: 369 base pairs
          ( B ) TYPE: nucleic acid
          ( C ) STRANDEDNESS: double
          ( D ) TOPOLOGY: linear ( x i ) SEQUENCE DESCRIPTION: SEQ ID NO:25:

CAGGTTCAGC TGGTTCAGTC TGGGGCTGAG GTGAAGAAGC CTGGGTCCTC GGTGAAGGTC 60

TCCTGCAAGG CTTCTGGAGG CACCTTCAGC AACTCTCCTA TCAACTGGCT GCGACAGGCC 120

CCCGGACAAG GGCTTGAGTG GATGGGAAGT ATCATCCCTT CCTTTGGTAC AGCAAACTAC 180

GCTCAGAAGT TCCAGGGCAG ACTCACGATT ACCGCGGACG AATCCACGAG CACAGCCTAC 240

ATGGAGCTGA GCAGCCTGAG ATCTGAGGAC ACGGCCGTGT ATTACTGTGC GGGACGGAGC 300

CACAACTACG AACTCTACTA CTACTACATG GACGTCTGGG GCCAGGGGAC AATGGTCACC 360

GTCTCGAGT 369

( 2 ) INFORMATION FOR SEQ ID NO:26:

(i) SEQUENCE CHARACTERISTICS:
    (A) LENGTH: 360 base pairs
    (B) TYPE: nucleic acid
    (C) STRANDEDNESS: double
    (D) TOPOLOGY: linear (xi) SEQUENCE DESCRIPTION: SEQ ID NO:26:

| | | | | | | |
|---|---|---|---|---|---|---|
| CAGGTTACCC | TGCAGCAGTC | TGGGGCTGAG | GTGAAGAAGC | CTGGGCCCTC | GGTGAAGGTC | 60 |
| TCCTGCAAGG | CTTCTGGATA | TACCTTCACC | GCCTATGGTT | TCAACTGGGT | GCGACAGGCC | 120 |
| CCCGGACAAG | GGCTTGAGTG | GATGTGGATC | AGCGCTTACA | GTGGTAACAC | AAAGTACGCT | 180 |
| CAGAAGTTCC | AGGGCAGAGT | CACGATGACC | ACAGACACAT | CCACGAGCAC | AGCCTACATG | 240 |
| GAGCTGAGGA | GCCTGAGATC | TGAGGACACG | GCCGTGTATT | ACTGTGCGGG | ACGGAGAGGC | 300 |
| GGCTTCCGAT | TCCGACCGAT | GGACGTCTGG | GGCCAGGGGA | CAATGGTCAC | CGTCTCGAGC | 360 |

(2) INFORMATION FOR SEQ ID NO:27:

(i) SEQUENCE CHARACTERISTICS:
    (A) LENGTH: 333 base pairs
    (B) TYPE: nucleic acid
    (C) STRANDEDNESS: double
    (D) TOPOLOGY: linear (xi) SEQUENCE DESCRIPTION: SEQ ID NO:27:

| | | | | | | |
|---|---|---|---|---|---|---|
| CAGTCTGTGT | TGACGCAGCC | GCCCTCAGTG | TCTGCGCCCC | CAGGACAGAA | GGTCACCATT | 60 |
| TCCTGCTCTG | GAAGCACCCC | CAACATTGGG | AATAATTATG | TCTCCTGGTA | CCAACAGCAC | 120 |
| CCAGGCAAAG | CCCCCAAACT | CATGATTTAT | GATGTCAGTA | AGCGGCCCTC | AGGGGTCCCT | 180 |
| GACCGATTCT | CTGGCTCCAA | GTCTGGCAAC | TCAGCCTCCC | TGGACATCAG | TGGGCTCCAG | 240 |
| TCTGAGGATG | AGGCTGATTA | TTACTGTGCA | GCATGGGATG | ACAGCCTGAG | TGAATTTCTC | 300 |
| TTCGGAACTG | GGACCAAGCT | GGAGATCAAA | CGT | | | 333 |

(2) INFORMATION FOR SEQ ID NO:28:

(i) SEQUENCE CHARACTERISTICS:
    (A) LENGTH: 327 base pairs
    (B) TYPE: nucleic acid
    (C) STRANDEDNESS: double
    (D) TOPOLOGY: linear (xi) SEQUENCE DESCRIPTION: SEQ ID NO:28:

| | | | | | | |
|---|---|---|---|---|---|---|
| TCGTCTGAGC | TGACTCAGGA | CCCTGCTGTG | TCTGTGCCCT | TGGGACAGAC | AGTCAGGATC | 60 |
| ACATGCCAAG | GAGACAGCCT | CAGAAGCTAT | TATGCAAGCT | GGTACCAGCA | GAAGCCAGGA | 120 |
| CAGCCCCCTG | TACTTGTCAT | CTATGGTAAA | AACAACCGGC | CCTCAGGGAT | CCCAGACCGA | 180 |
| TTCTCTGGCT | CCAGCTCAGG | AAACACAGCT | TCCTTGACCA | TCACTGGGGC | TCAGGCGGAA | 240 |
| GATGAGGCTG | ACTATTACTG | TAACTCCCGG | GACAGCAGTG | GTAACCATGT | GGTATTCGGC | 300 |
| GGAGGGACCA | AGCTGGAGAT | CAAACGT | | | | 327 |

(2) INFORMATION FOR SEQ ID NO:29:

(i) SEQUENCE CHARACTERISTICS:
    (A) LENGTH: 324 base pairs
    (B) TYPE: nucleic acid
    (C) STRANDEDNESS: double
    (D) TOPOLOGY: linear (xi) SEQUENCE DESCRIPTION: SEQ ID NO:29:

| | | | | | | |
|---|---|---|---|---|---|---|
| GACATCCAGA | TGACCCAGTC | TCCTTCCACC | CTGTCTGCAT | CTATTGGAGA | CAGAGTCACC | 60 |
| ATCACCTGCC | GGGCCAGTGA | GGGTATTTAT | CACTGGTTGG | CCTGGTATCA | GCAGAAGCCA | 120 |

```
GGGAAAGCCC  CTAAACTCCT  GATCTATAAG  GCCTCTAGTT  TAGCCAGTGG  GGCCCCATCA    180

AGGTTCAGCG  GCAGTGGATC  TGGGACAGAT  TTCACTCTCA  CCATCAGCAG  CCTGCAGCCT    240

GATGATTTTG  CAACTTATTA  CTGCCAACAA  TATAGTAATT  ATCCGCTCAC  TTTCGGCGGA    300

GGGACCAAGC  TGGAGATCAA  ACGT                                              324
```

( 2 ) INFORMATION FOR SEQ ID NO:30:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

```
GTCGTCTTTC  CAGACGTTAG  T                                                  21
```

( 2 ) INFORMATION FOR SEQ ID NO:31:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

```
CAGGAAACAG  CTATGAC                                                        17
```

( 2 ) INFORMATION FOR SEQ ID NO:32:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

```
CTCTTCTGAG  ATGAGTTTTT  G                                                  21
```

( 2 ) INFORMATION FOR SEQ ID NO:33:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

```
GGCGGAGGTG  GCTCTGGCGG  T                                                  21
```

( 2 ) INFORMATION FOR SEQ ID NO:34:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

```
ACGGCCAGAG  CCACCTCCGC  C                                                  21
```

( 2 ) INFORMATION FOR SEQ ID NO:35:

( i ) SEQUENCE CHARACTERISTICS:
        ( A ) LENGTH: 23 base pairs
        ( B ) TYPE: nucleic acid ( C ) STRANDEDNESS: single
            ( D ) TOPOLOGY: linear ( x i ) SEQUENCE DESCRIPTION: SEQ ID NO:35:

AGCGGATAAC AATTTCACAC AGG                                                                                           2 3

( 2 ) INFORMATION FOR SEQ ID NO:36:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:36:

TACTACATGG ACGTCTGG                                                                                                 1 8

( 2 ) INFORMATION FOR SEQ ID NO:37:

( i ) SEQUENCE CHARACTERISTICS:
            ( A ) LENGTH: 51 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:37:

GTGATGGTGA TGATGATGTG CGGCCGGACG TTTGATCTCC AGCTTGGTCC C                                                             5 1

( 2 ) INFORMATION FOR SEQ ID NO:38:

( i ) SEQUENCE CHARACTERISTICS:
            ( A ) LENGTH: 63 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:38:

GACGTCCATG TAGTAGTAGT AADNMYYABH ABHABNABHA BNTCCGCAC AGTAATACAC                                                     6 0

GGC                                                                                                                 6 3

( 2 ) INFORMATION FOR SEQ ID NO:39:

( i ) SEQUENCE CHARACTERISTICS:
            ( A ) LENGTH: 66 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:39:

GATCTCCAGC TTGGTCCCTC CGCCGAAAGT GAGCGGABHA BHABHABHTT GTTGGCAGTA                                                    6 0

ATAAGT                                                                                                              6 6

( 2 ) INFORMATION FOR SEQ ID NO:40:

( i ) SEQUENCE CHARACTERISTICS:
            ( A ) LENGTH: 216 base pairs
            ( B ) TYPE: nucleic acid
            ( C ) STRANDEDNESS: double
            ( D ) TOPOLOGY: circular ( i x ) FEATURE:
            ( A ) NAME/KEY: CDS
            ( B ) LOCATION: 34..204

( x i ) SEQUENCE DESCRIPTION: SEQ ID NO:40:

ATGCTTCTAG ACAATTGTGA GGAGGTTTAT CTT GTG AAA AAA TTA TTA TTC GCA                                                     5 4
                                    Val Lys Lys Leu Leu Phe Ala

```
                                                  1                    5
ATT  CCT  TTA  GTT  GTT  CCT  TTC  TAT  GCG  GCC  CAG  CCG  GCC  ATG  GCC  CAG      102
Ile  Pro  Leu  Val  Val  Pro  Phe  Tyr  Ala  Ala  Gln  Pro  Ala  Met  Ala  Gln
          10                      15                      20

GTG  CAG  CTG  CAG  GTC  GGC  CTC  GAG  ATC  AAA  CGG  GCG  GCC  GCA  GAA  CAA      150
Val  Gln  Leu  Gln  Val  Gly  Leu  Glu  Ile  Lys  Arg  Ala  Ala  Ala  Glu  Gln
          25                      30                      35

AAA  CTC  ATC  TCA  GAA  GAG  GAT  CTG  AAT  GGG  GCC  TGT  CAT  CAC  CAT  CAT      198
Lys  Leu  Ile  Ser  Glu  Glu  Asp  Leu  Asn  Gly  Ala  Cys  His  His  His  His
40                       45                      50                       55

CAC  CAT  TAATAAGAAT  TC                                                              216
His  His
```

( 2 ) INFORMATION FOR SEQ ID NO:41:

( i ) SEQUENCE CHARACTERISTICS:
        ( A ) LENGTH: 57 amino acids
        ( B ) TYPE: amino acid
        ( D ) TOPOLOGY: linear ( i i ) MOLECULE TYPE: protein ( x i ) SEQUENCE DESCRIPTION: SEQ ID NO:41:

```
Val  Lys  Lys  Leu  Leu  Phe  Ala  Ile  Pro  Leu  Val  Val  Pro  Phe  Tyr  Ala
 1              5                        10                      15

Ala  Gln  Pro  Ala  Met  Ala  Gln  Val  Gln  Leu  Gln  Val  Gly  Leu  Glu  Ile
               20                      25                      30

Lys  Arg  Ala  Ala  Ala  Glu  Gln  Lys  Leu  Ile  Ser  Glu  Glu  Asp  Leu  Asn
          35                      40                      45

Gly  Ala  Cys  His  His  His  His  His  His
          50                      55
```

( 2 ) INFORMATION FOR SEQ ID NO:42:

( i ) SEQUENCE CHARACTERISTICS:
        ( A ) LENGTH: 141 base pairs
        ( B ) TYPE: nucleic acid
        ( C ) STRANDEDNESS: double
        ( D ) TOPOLOGY: circular ( i x ) FEATURE:
        ( A ) NAME/KEY: CDS
        ( B ) LOCATION: 1..129

( x i ) SEQUENCE DESCRIPTION: SEQ ID NO:42:

```
GCG  GCC  CAG  CCG  GCC  ATG  GCC  CAG  GTG  CAG  CTG  CAG  GTC  GGC  CTC  GAG      48
Ala  Ala  Gln  Pro  Ala  Met  Ala  Gln  Val  Gln  Leu  Gln  Val  Gly  Leu  Glu
 1              5                        10                      15

ATC  AAA  CGG  GCG  GCC  GCA  GGT  GCG  CCG  GTG  CCG  TAT  CCG  GAT  CCG  CTG      96
Ile  Lys  Arg  Ala  Ala  Ala  Gly  Ala  Pro  Val  Pro  Tyr  Pro  Asp  Pro  Leu
          20                      25                      30

GAA  CCG  CGT  GCC  GCA  CAT  CAC  CAT  CAT  CAC  CAT  TAATAAGAAT  TC              141
Glu  Pro  Arg  Ala  Ala  His  His  His  His  His  His
          35                      40
```

( 2 ) INFORMATION FOR SEQ ID NO:43:

( i ) SEQUENCE CHARACTERISTICS:
        ( A ) LENGTH: 43 amino acids
        ( B ) TYPE: amino acid
        ( D ) TOPOLOGY: linear ( i i ) MOLECULE TYPE: protein ( x i ) SEQUENCE DESCRIPTION: SEQ ID NO:43:

```
Ala Ala Gln Pro Ala Met Ala Gln Val Gln Leu Gln Val Gly Leu Glu
 1               5                   10                  15

Ile Lys Arg Ala Ala Ala Gly Ala Pro Val Pro Tyr Pro Asp Pro Leu
            20                  25                  30

Glu Pro Arg Ala Ala His His His His His His
            35                  40
```

( 2 ) INFORMATION FOR SEQ ID NO:44:

( i ) SEQUENCE CHARACTERISTICS:
        ( A ) LENGTH: 369 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:44:

```
CAGGTTCAGC TGGTTCAGTC TGGGGCTGAG GTGAAGAAGC CTGGGTCCTC GGTGAAGGTC      60
TCCTGCAAGG CTTCTGGAGG CACCTTCAGC AACTCTCCTA TCAACTGGCT GCGACAGGCC     120
CCCGGACAAG GGCTTGAGTG GATGGGAAGT ATCATCCCTT CCTTTGGTAC AGCAAACTAC     180
GCTCAGAAGT TCCAGGGCAG ACTCACGATT ACCGCGGACG AATCCACGAG CACAGCCTAC     240
ATGGAGCTGA GCAGCCTGAG ATCTGAGGAC ACGGCCGTGT ATTACTGTGC GGGATGTTCT     300
CATAATTATG AGCTTTACTA CTACTACATG GACGTCTGGG GCCAGGGGAC AATGGTCACC     360
GTCTCGAGT                                                            369
```

( 2 ) INFORMATION FOR SEQ ID NO:45:

( i ) SEQUENCE CHARACTERISTICS:
        ( A ) LENGTH: 369 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:45:

```
CAGGTTCAGC TGGTTCAGTC TGGGGCTGAG GTGAAGAAGC CTGGGTCCTC GGTGAAGGTC      60
TCCTGCAAGG CTTCTGGAGG CACCTTCAGC AACTCTCCTA TCAACTGGCT GCGACAGGCC     120
CCCGGACAAG GGCTTGAGTG GATGGGAAGT ATCATCCCTT CCTTTGGTAC AGCAAACTAC     180
GCTCAGAAGT TCCAGGGCAG ACTCACGATT ACCGCGGACG AATCCACGAG CACAGCCTAC     240
ATGGAGCTGA GCAGCCTGAG ATCTGAGGAC ACGGCCGTGT ATTACTGTGC GGGAGCTAAT     300
TCTTGTAATA GGTCTTACTA CTACTACATG GACGTCCGGG GCCAGGGGAC AATGGTCACC     360
GTCTCGAGT                                                            369
```

( 2 ) INFORMATION FOR SEQ ID NO:46:

( i ) SEQUENCE CHARACTERISTICS:
        ( A ) LENGTH: 369 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:46:

```
CAGGTTCAGC TGGTTCAGTC TGGGGCTGAG GTGAAGAAGC CTGGGTCCTC GGTGAAGGTC      60
TCCTGCAAGG CTTCTGGAGG CACCTTCAGC AACTCTCCTA TCAACTGGCT GCGACAGGCC     120
CCCGGACAAG GGCTTGAGTG GATGGGAAGT ATCATCCCTT CCTTTGGTAC AGCAAACTAC     180
GCTCAGAAGT TCCAGGGCAG ACTCACGATT ACCGCGGACG AATCCACGAG CACAGCCTAC     240
ATGGAGCTGA GCAGCCTGAG ATCTGAGGAC ACGGCCGTGT ATTACTGTGC GAGACATAAT     300
```

| | | | | | |
|---|---|---|---|---|---|
| CATAATTATG | AGCTTTACTA | CTACTACATG | GACGTCTGGG | GCCAGGGGAC | AATGGTCACC | 360 |
| GTCTCGAGT | | | | | | 369 |

( 2 ) INFORMATION FOR SEQ ID NO:47:

( i ) SEQUENCE CHARACTERISTICS:
        ( A ) LENGTH: 369 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:47:

| | | | | | |
|---|---|---|---|---|---|
| CAGGTTCAGC | TGGTTCAGTC | TGGGGCTGAG | GTGAAGAAGC | CTGGGTCCTC | GGTGAAGGTC | 60 |
| TCCTGCAAGG | CTTCTGGAGG | CACCTTCAGC | AACTCTCCTA | TCAACTGGCT | GCGACAGGCC | 120 |
| CCCGGACAAG | GGCTTGAGTG | GATGGGAAGT | ATCATCCCTT | CCTTTGGTAC | AGCAAACTAC | 180 |
| GCTCAGAAGT | TCCAGGGCAG | ACTCACGATT | ACCGCGGACG | AATCCACGAG | CACAGCCTAC | 240 |
| ATGGAGCTGA | GCAGCCTGAG | ATCTGAGGAC | ACGGCCGTGT | ATTACTGTGC | GGGACGTAGT | 300 |
| CATACTTATG | AGCTTTACTA | CTACTACATG | GACGTCTGGG | GCCAGGGGAC | AATGGTCACC | 360 |
| GTCTCGAGT | | | | | | 369 |

( 2 ) INFORMATION FOR SEQ ID NO:48:

( i ) SEQUENCE CHARACTERISTICS:
        ( A ) LENGTH: 324 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:48:

| | | | | | |
|---|---|---|---|---|---|
| GACATCGTGA | TGACCCAGTC | TCCTTCCACC | CTGTCTGCAT | CTGTAGGAGA | CAGAGTCACC | 60 |
| ATCACCTGCC | GGGCCAGTCA | GGGTATTAGT | AGCTGGTTGG | CCTGGTATCA | GCAGAAGCCA | 120 |
| GGGAAAGCCC | CTAAACTCCT | GATCTATAAG | GCCTCTAGTT | TAGCCAGTGG | GGCCCCATCA | 180 |
| AGGTTCAGCG | GCAGTGGATC | TGGGACAGAT | TTCACTCTCA | CCATCAGCAG | CCTGCAGCCT | 240 |
| GATGATTTTG | CAACTTATTA | CTGCCAACAA | TATAGTAATT | ATCCGCTCAC | TTTCGGCGGA | 300 |
| GGGACCAAGC | TGGAGATCAA | ACGT | | | | 324 |

( 2 ) INFORMATION FOR SEQ ID NO:49:

( i ) SEQUENCE CHARACTERISTICS:
        ( A ) LENGTH: 324 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:49:

| | | | | | |
|---|---|---|---|---|---|
| GACATCGTGA | TGACCCAGTC | TCCTTCCACC | CTGTCTGCAT | CTGTAGGAGA | CAGAGTCACC | 60 |
| ATCACCTGCC | GGGCCAGTCA | GGGTATTAGT | AGCTGGTTGG | CCTGGTATCA | GCAGAAGCCA | 120 |
| GGGAGAGCCC | CTAAGGTCCT | GATCTATAAG | GCCTCTACTT | TAGAAGTCGG | GGTCCCATCA | 180 |
| AGGTTCAGCG | GCAGTGGATC | TGGGACAGAT | TTCACTCTCA | CCATCAGCAG | CCTGCAACCT | 240 |
| GAAGATTTTG | CAACTTACTA | CTGCCAACAA | AGTTACAGTA | CCCCGTGGAC | TTTCGGCCAA | 300 |
| GGGACCAAGC | TGGAGATCAA | ACGT | | | | 324 |

( 2 ) INFORMATION FOR SEQ ID NO:50:

( i ) SEQUENCE CHARACTERISTICS:
        ( A ) LENGTH: 324 base pairs (B) TYPE: nucleic acid
(C) STRANDEDNESS: double
(D) TOPOLOGY: linear (xi) SEQUENCE DESCRIPTION: SEQ ID NO:50:

| | | | | | |
|---|---|---|---|---|---|
| GACATCGTGA | TGACCCAGTC | TCCTTCCACC | CTGTCTGCAT | CTGTAGGAGA | CAGAGTCACC | 60
| ATCACCTGCC | GGGCCAGTCA | GGGTATTAGT | AGCTGGTTGG | CCTGGTATCA | GCAGAAGCCA | 120
| GGGAGAGCCC | CTAAGGTCCT | GATCTATAAG | GCCTCTACTT | TAGAAAGCGG | GGTCCCATCA | 180
| AGGTTCAGCG | GCAGTGGATC | TGGGACAGAT | TTCACTCTCA | CCATCAGCAG | CCTGCAACCT | 240
| GAAGATTTTG | CAACTTACTA | CTGCCAACAA | AGTTACAGTA | CCCCGTGGAC | TTTCGGCCAA | 300
| GGGACCAAGC | TGGAGATCAA | ACGT | | | | 324

(2) INFORMATION FOR SEQ ID NO:51:

(i) SEQUENCE CHARACTERISTICS:
(A) LENGTH: 324 base pairs
(B) TYPE: nucleic acid
(C) STRANDEDNESS: double
(D) TOPOLOGY: linear (xi) SEQUENCE DESCRIPTION: SEQ ID NO:51:

GACATCCAGA TGACCCAGTC TCCTTCCACC CTGTCTGCAT CTATTGGAGA CAGAGTCACC 60
ATCACCTGCC GGGCCAGTGA GGGTATTTAT CACTGGTTGG CCTGGTATCA GCAGAAGCCA 120
GGGAAAGCCC CTAAACTCCT GATCTATAAG GCCTCTAGTT TAGCCAGTGG GGCCCCATCA 180
AGGTTCAGCG GCAGTGGATC TGGGACAGAT TTCACTCTCA CCATCAGCAG CCTGCAGCCT 240
GATGATTTTG CAACTTATTA CTGCCAACAA AGTTACAGTA CTCCGCTCAC TTTCGGCGGA 300
GGGACCAAGC TGGAGATCAA ACGT 324

(2) INFORMATION FOR SEQ ID NO:52:

(i) SEQUENCE CHARACTERISTICS:
(A) LENGTH: 324 base pairs
(B) TYPE: nucleic acid
(C) STRANDEDNESS: double
(D) TOPOLOGY: linear (xi) SEQUENCE DESCRIPTION: SEQ ID NO:52:

GACATCCAGA TGACCCAGTC TCCTTCCACC CTGTCTGCAT CTATTGGAGA CAGAGTCACC 60
ATCACCTGCC GGGCCAGTGA GGGTATTTAT CACTGGTTGG CCTGGTATCA GCAGAAGCCA 120
GGGAAAGCCC CTAAACTCCT GATCTATAAG GCCTCTAGTT TAGCCAGTGG GGCCCCATCA 180
AGGTTCAGCG GCAGTGGATC TGGGACAGAT TTCACTCTCA CCATCAGCAG CCTGCAGCCT 240
GATGATTTTG CAACTTATTA CTGCCAACAA TATGATAATG GTCCGCTCAC TTTCGGCGGA 300
GGGACCAAGC TGGAGATCAA ACGT 324

(2) INFORMATION FOR SEQ ID NO:53:

(i) SEQUENCE CHARACTERISTICS:
(A) LENGTH: 108 amino acids
(B) TYPE: amino acid
(D) TOPOLOGY: linear (xi) SEQUENCE DESCRIPTION: SEQ ID NO:53:

Asp Ile Gln Met Thr Gln Ser Pro Ser Thr Leu Ser Ala Ser Ile Gly
1               5                   10                  15

Asp Arg Val Thr Ile Thr Cys Arg Ala Ser Glu Gly Ile Tyr His Trp
            20                  25                  30

-continued

| Leu | Ala | Trp 35 | Tyr | Gln | Gln | Lys | Pro 40 | Gly | Lys | Ala | Pro | Lys 45 | Leu | Leu | Ile |
| Tyr | Lys 50 | Ala | Ser | Ser | Leu | Ala 55 | Ser | Gly | Ala | Pro | Ser 60 | Arg | Phe | Ser | Gly |
| Ser 65 | Gly | Ser | Gly | Thr | Asp 70 | Phe | Thr | Leu | Thr | Ile 75 | Ser | Ser | Leu | Gln | Pro 80 |
| Asp | Asp | Phe | Ala | Thr 85 | Tyr | Tyr | Cys | Gln | Gln 90 | Tyr | Ser | Asn | Tyr | Pro 95 | Leu |
| Thr | Phe | Gly | Gly 100 | Gly | Thr | Lys | Leu | Glu 105 | Ile | Lys | Arg | | | | |